(12) United States Patent
Stahl et al.

(10) Patent No.: US 6,472,179 B2
(45) Date of Patent: *Oct. 29, 2002

(54) RECEPTOR BASED ANTAGONISTS AND METHODS OF MAKING AND USING

(75) Inventors: Neil Stahl, Carmel; George D. Yancopoulos, Yorktown Heights, both of NY (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 09/313,942

(22) Filed: May 19, 1999

(65) Prior Publication Data

US 2002/0012962 A1 Jan. 31, 2002

Related U.S. Application Data

(60) Provisional application No. 60/101,858, filed on Sep. 25, 1998.

(51) Int. Cl.[7] .......................... C12P 21/04; C07H 21/04
(52) U.S. Cl. ................ 435/69.7; 435/320.1; 435/252.3; 435/254.2; 435/325; 435/348; 435/365; 435/361; 435/328; 435/335; 536/23.5; 536/23.4; 530/350; 530/388.22; 514/2; 424/179.1
(58) Field of Search .................. 424/179.1; 530/350, 530/388.22; 514/2; 536/23.5, 23.4; 435/335, 320.1, 325, 252.3, 348, 361, 365, 254.2, 328, 69.7

(56) References Cited

U.S. PATENT DOCUMENTS

| 5,262,522 A | 11/1993 | Gearing ...................... 530/350 |
| 5,426,048 A | 6/1995 | Gearing ...................... 435/252 |
| 5,470,952 A | 11/1995 | Stahl et al. ................. 530/350 |
| 5,510,259 A | 4/1996 | Sugamura et al. ........ 435/240.2 |
| 5,599,905 A | 2/1997 | Mosley et al. .............. 530/350 |
| 5,844,099 A | 12/1998 | Stahl et al. ................. 530/350 |
| 6,143,871 A | 11/2000 | Bonnefoy et al. .......... 530/351 |

FOREIGN PATENT DOCUMENTS

| EP | 0367566 B1 | 5/1997 | |
| WO | WO 93/10151 | 5/1993 | ........... C07K/13/00 |
| WO | WO 96/11213 | 4/1996 | |

OTHER PUBLICATIONS

The Leukocyte Antigen FactsBook, Barclay et al., editors. Academic Press, Harcourt Brace Jovanovich, Publishers, 1993, pp. 162, 166, 188, 290, 320, 322, 330, 338 and 410.*
Sato, et al., Current Opinions in Cell Biology, 1994, 6: 174–179.
Miyajima, et al., Annual Review of Immunology, 1992, 10: 295–331.
Kondo, et al., Science, 1993, 262: 1874–1877.
Hilton, et al., EMBO Journal, 1994, 13:4765–4775.
Stahl and Yancopoulos, Cell, 1993, 74: 587–590.
Bassing, et al., Journal of Biological Chemistry, 1994, 269: 14861–14864.
Kotenko, et al., Journal of Biological Chemistry, 1995, 270: 20915–20921.
Greenfeder, et al., Journal of Biological Chemistry, 1995, 270: 13757–13765.
Lebrun and Vale, Molecular Cell Biology, 1997, 17: 1682–1691.
Kennedy and Park, Journal of Clinical Immunology, 1996, 16: 134–143.
Wesche, et al., Journal of Biological Chemistry, 1997, 272: 7727–7731.
Immunobiology, The Immune System in Health and Disease, 2nd Edition, by Charles A. Janeway, Jr. And Paul Travers, published by Current Biology Lt./ Garland Publishing In., copyright 1996.

* cited by examiner

Primary Examiner—Lorraine Spector
Assistant Examiner—Eileen B. O'Hara
(74) Attorney, Agent, or Firm—Robert J. Cobert; Gail M. Kempler; Linda O. Palladino

(57) ABSTRACT

The present invention provides a fusion polypeptide capable of binding a cytokine to form a nonfunctional complex. It also provides a nucleic acid sequence encoding the fusion polypeptide and methods of making and uses for the fusion polypeptide.

25 Claims, 60 Drawing Sheets

Fig. 4A

Amino acid sequence of human gp130-Fc-His6

Sequence Range: 1 to 861

```
          10              20              30              40              50              60
           *               *               *               *               *               *
MVTLQTWVVQALFIFLTTES  TGELLDPCGYISPESPVVQL  HSNFTAVCVLKEKCMDYFHV 70              80              90             100             110             120
           *               *               *               *               *               *
NANYIVWKTNHFTIPKEQYT  IINRTASSVTFTDIASLNIQ  LTCNILTFGQLEQNVYGITI 130             140             150             160             170             180
           *               *               *               *               *               *
ISGLPPEKPKNLSCIVNEGK  KMRCEWDGGRETHLETNFTL  KSEWATHKFADCKAKRDTPT 190             200             210             220             230             240
           *               *               *               *               *               *
SCTVDYSTVYFVNIEVWVEA  ENALGKVTSDHINFDPVYKV  KPNPPHNLSVINSEELSSIL 250             260             270             280             290             300
           *               *               *               *               *               *
KLTWTNPSIKSVIILKYNIQ  YRTKDASTWSQIPPEDTAST  RSSFTVQDLKPFTEYVFRIR 310             320             330             340             350             360
           *               *               *               *               *               *
CMKEDGKGYWSDWSEEASGI  TYEDRPSKAPSFWYKIDPSH  TQGYRTVQLVWKTLPPFEAN 370             380             390             400             410             420
           *               *               *               *               *               *
GKILDYEVTLTRWKSHLQNY  TVNATKLTVNLTNDRYLATL  TVRNLVGKSDAAVLTIPACD 430             440             450             460             470             480
           *               *               *               *               *               *
FQATHPVMDLKAFPKDNMLW  VEWTTPRESVKKYILEWCVL  SDKAPCITDWQQEDGTVHRT 490             500             510             520             530             540
           *               *               *               *               *               *
YLRGNLAESKCYLITVTPVY  ADGPGSPESIKAYLKQAPPS  KGPTVRTKKVGKNEAVLEWD 550             560             570             580             590             600
           *               *               *               *               *               *
QLPVDVQNGFIRNYTIFYRT  IIGNETAVNVDSSHTEYTLS  SLTSDTLYMVRMAAYTDEGG 610             620             630             640             650             660
           *               *               *  †           †  *               *               *
KDGPEFTFTTPKFAQGEIES  GEPKSCDKTHTCPPCPAPEL  LGGPSVFLFPPKPKDTLMIS 670             680             690             700             710             720
           *               *               *               *               *               *
RTPEVTCVVVDVSHEDPEVK  FNWYVDGVEVHNAKTKPREE  QYNSTYRVVSVLTVLHQDWL 730             740             750             760             770             780
           *               *               *               *               *               *
```

Fig. 4B

NGKEYKCKVSNKALPAPIEK TISKAKGQPREPQVYTLPPS RDELTKNQVSLTCLVKGFYP

```
     790          800          810          820          830          840
      *            *            *            *            *            *
```
SDIAVEWESNGQPENNYKTT PPVLDSDGSFFLYSKLTVDK SRWQQGNVFSCSVMHEALHN

```
     850          860
      *            *
```
HYTQKSLSLSPGKHHHHHH.

Fig.5.

The amino acid sequence of human IL-6Rα-Fc

Sequence Range: 1 to 594

```
      10           20           30           40           50           60
      *            *            *            *            *            *
```
MVAVGCALLAALLAAPGAAL APRRCPAQEVARGVLTSLPG DSVTLTCPGVEPEDNATVHW

```
      70           80           90          100          110          120
       *            *            *            *            *            *
```
VLRKPAAGSHPSRWAGMGRR LLLRSVQLHDSGNYSCYRAG RPAGTVHLLVDVPPEEPQLS

```
     130          140          150          160          170          180
      *            *            *            *            *            *
```
CFRKSPLSNVVCEWGPRSTP SLTTKAVLLVRKFQNSPAED FQEPCQYSQESQKFSCQLAV

```
     190          200          210          220          230          240
      *            *            *            *            *            *
```
PEGDSSFYIVSMCVASSVGS KFSKTQTFQGCGILQPDPPA NITVTAVARNPRWLSVTWQD

```
     250          260          270          280          290          300
      *            *            *            *            *            *
```
PHSWNSSFYRLRFELRYRAE RSKTFTTWMVKDLQHHCVIH DAWSGLRHVVQLRAQEEFGQ

```
     310          320          330          340          350          360
      *            *            *            *            *            *
```
GEWSEWSPEAMGTPWTESRS PPAENEVSTPMQALTTNKDD DNILFRDSANATSLPVQDAG

```
     370          380          390          400          410          420
      *†           †*            *            *            *            *
```
EPKSCDKTHTCPPCPAPELL GGPSVFLFPPKPKDTLMISR TPEVTCVVVDVSHEDPEVKF

```
     430          440          450          460          470          480
      *            *            *            *            *            *
```
NWYVDGVEVHNAKTKPREEQ YNSTYRVVSVLTVLHQDWLN GKEYKCKVSNKALPAPIEKT

```
     490          500          510          520          530          540
      *            *            *            *            *            *
```
ISKAKGQPREPQVYTLPPSR DELTKNQVSLTCLVKGFYPS DIAVEWESNGQPENNYKTTP

```
     550          560          570          580          590
      *            *            *            *            *
```
PVLDSDGSFFLYSKLTVDKS RWQQGNVFSCSVMHEALHNH YTQKSLSLSPGK.

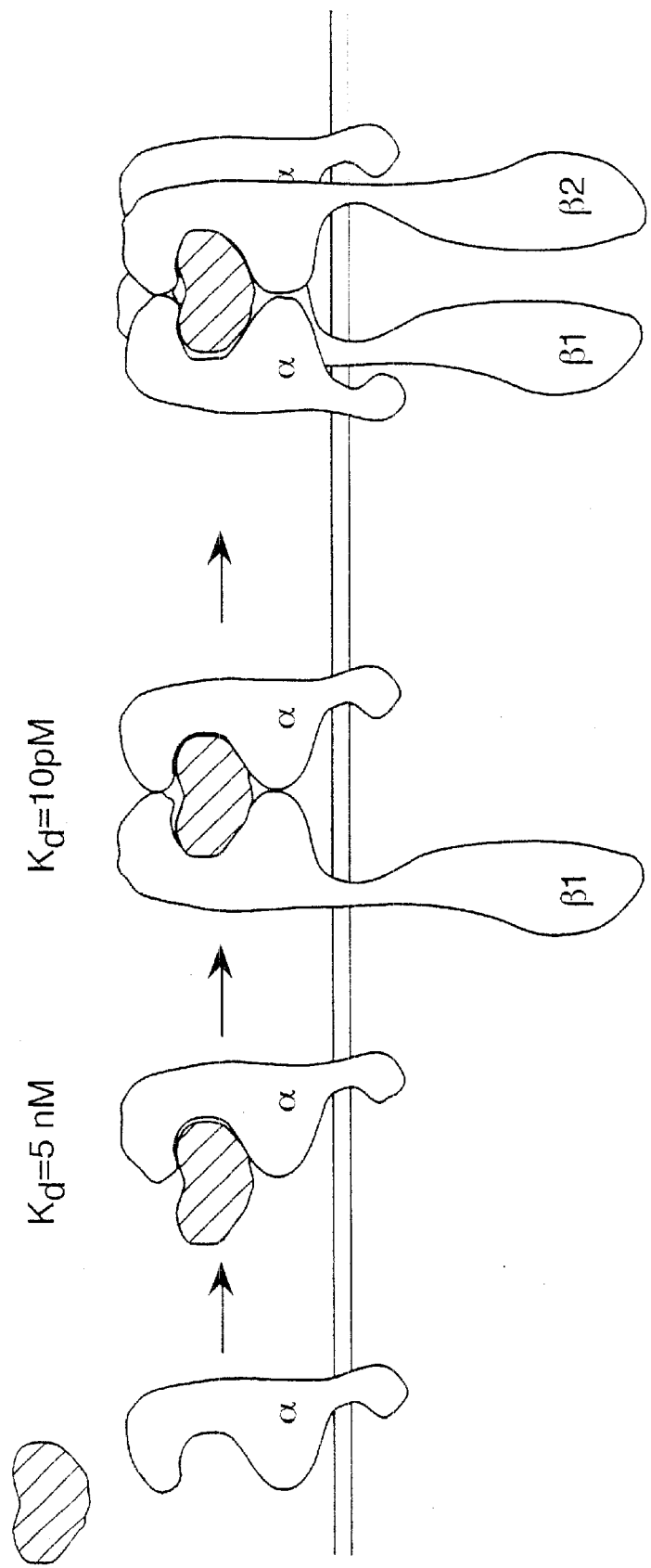

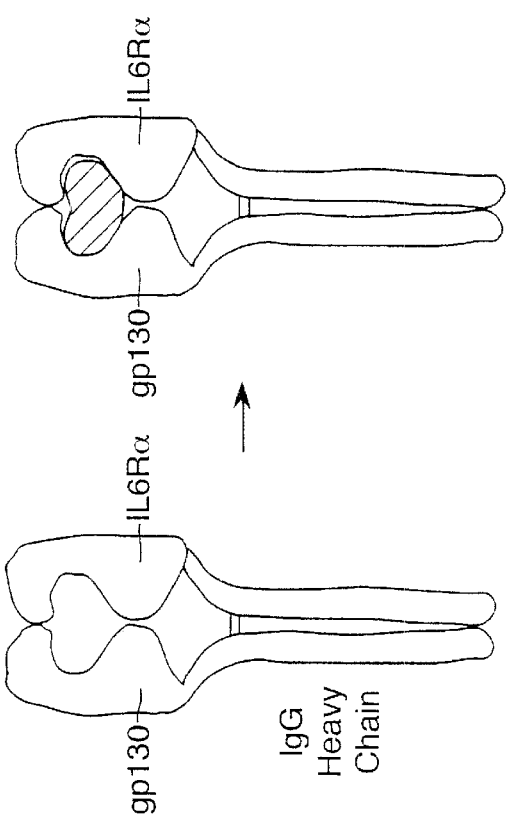
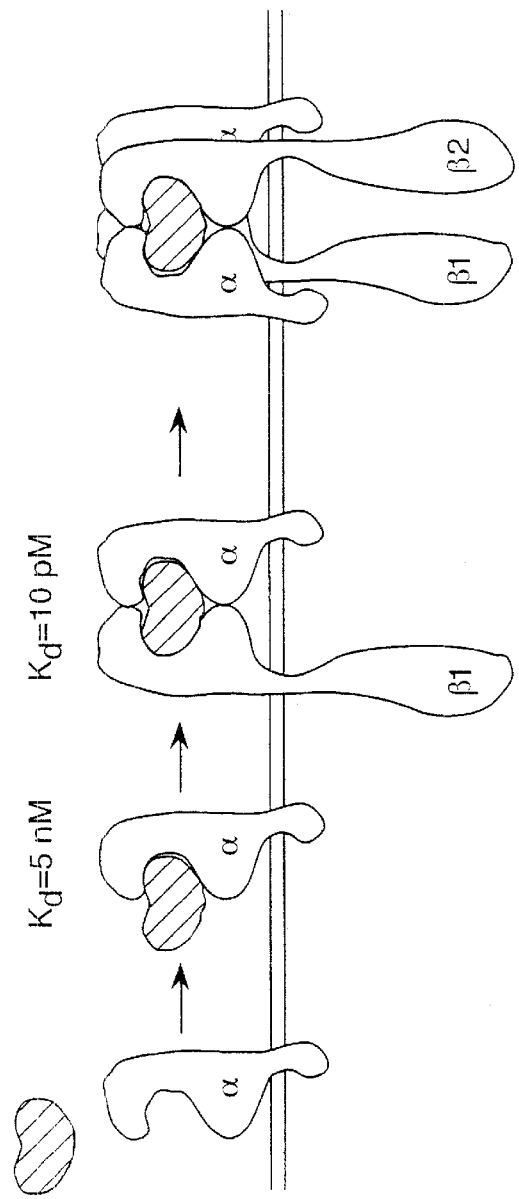
Fig. 7.

Immunoglobulin Heavy/Light Chain receptor Fusions

Fig. 9A

Amino acid sequence of gp130-Cγ1

Sequence Range: 1 to 952

```
              10           20           30           40           50           60
               *            *            *            *            *            *
      MVTLQTWVVQALFIFLTTES  TGELLDPCGYISPESPVVQL  HSNFTAVCVLKEKCMDYFHV 70           80           90          100          110          120
               *            *            *            *            *            *
      NANYIVWKTNHFTIPKEQYT  IINRTASSVTFTDIASLNIQ  LTCNILTFGQLEQNVYGITI 130          140          150          160          170          180
               *            *            *            *            *            *
      ISGLPPEKPKNLSCIVNEGK  KMRCEWDGGRETHLETNFTL  KSEWATHKFADCKAKRDTPT 190          200          210          220          230          240
               *            *            *            *            *            *
      SCTVDYSTVYFVNIEVWVEA  ENALGKVTSDHINFDPVYKV  KPNPPHNLSVINSEELSSIL 250          260          270          280          290          300
               *            *            *            *            *            *
      KLTWTNPSIKSVIILKYNIQ  YRTKDASTWSQIPPEDTAST  RSSFTVQDLKPFTEYVFRIR 310          320          330          340          350          360
               *            *            *            *            *            *
      CMKEDGKGYWSDWSEEASGI  TYEDRPSKAPSFWYKIDPSH  TQGYRTVQLVWKTLPPFEAN 370          380          390          400          410          420
               *            *            *            *            *            *
      GKILDYEVTLTRWKSHLQNY  TVNATKLTVNLTNDRYLATL  TVRNLVGKSDAAVLTIPACD 430          440          450          460          470          480
               *            *            *            *            *            *
      FQATHPVMDLKAFPKDNMLW  VEWTTPRESVKKYILEWCVL  SDKAPCITDWQQEDGTVHRT 490          500          510          520          530          540
               *            *            *            *            *            *
      YLRGNLAESKCYLITVTPVY  ADGPGSPESIKAYLKQAPPS  KGPTVRTKKVGKNEAVLEWD 550          560          570          580          590          600
               *            *            *            *            *            *
      QLPVDVQNGFIRNYTIFYRT  IIGNETAVNVDSSHTEYTLS  SLTSDTLYMVRMAAYTDEGG 610          620          630          640          650          660
               *            *            *            *            *            *
      KDGPEFTFTTPKFAQGEIES  GASTKGPSVFPLAPSSKSTS  GGTAALGCLVKDYFPEPVTV 670          680          690          700          710          720
               *            *            *            *            *            *
      SWNSGALTSGVHTFPAVLQS  SGLYSLSSVVTVPSSSLGTQ  TYICNVNHKPSNTKVDKKVE 730          740          750          760          770          780
               *            *            *            *            *            *
      PKSCDKTHTCPPCPAPELLG  GPSVFLFPPKPKDTLMISRT  PEVTCVVVDVSHEDPEVKFN
```

Fig. 9B

```
         790              800              810              820              830              840
          *                *                *                *                *                *
WYVDGVEVHNAKTKPREEQY  NSTYRVVSVLTVLHQDWLNG  KEYKCKVSNKALPAPIEKTI 850              860              870              880              890              900
          *                *                *                *                *                *
SKAKGQPREPQVYTLPPSRD  ELTKNQVSLTCLVKGFYPSD  IAVEWESNGQPENNYKTTPP 910              920              930              940              950
          *                *                *                *                *
VLDSDGSFFLYSKLTVDKSR  WQQGNVFSCSVMHEALHNHY  TQKSLSLSPGK*
```

Fig. 10.

Amino acid sequence of gp130Δ3fibro

```
Sequence Range: 1 to 332

10              20              30              40              50              60
           *               *               *               *               *               *
MVTLQTWVVQALFIFLTTES  TGELLDPCGYISPESPVVQL  HSNFTAVCVLKEKCMDYFHV 70              80              90             100             110             120
           *               *               *               *               *               *
NANYIVWKTNHFTIPKEQYT  IINRTASSVTFTDIASLNIQ  LTCNILTFGQLEQNVYGITI 130             140             150             160             170             180
           *               *               *               *               *               *
ISGLPPEKPKNLSCIVNEGK  KMRCEWDGGRETHLETNFTL  KSEWATHKFADCKAKRDTPT 190             200             210             220             230             240
           *               *               *               *               *               *
SCTVDYSTVYFVNIEVWVEA  ENALGKVTSDHINFDPVYKV  KPNPPHNLSVINSEELSSIL 250             260             270             280             290             300
           *               *               *               *               *               *
KLTWTNPSIKSVIILKYNIQ  YRTKDASTWSQIPPEDTAST  RSSFTVQDLKPFTEYVFRIR 310             320             330
           *               *               *
CMKEDGKGYWSDWSEEASGI  TYEDRPSKAPSG
```

Fig. 11.

Amino acid sequence of J-CH1

Sequence Range: 1 to 121

```
          10          20          30          40          50          60
           *           *           *           *           *           *
SGGQGTLVTVSSASTKGPSV FPLAPSSKSTSGGTAALGCL VKDYFPEPVTVSWNSGALTS 70          80          90         100         110         120
           *           *           *           *           *           *
GVHTFPAVLQSSGLYSLSSV VTVPSSSLGTQTYICNVNHK PSNTKVDKKVEPKSCDKTHT*
```

Fig. 12.

Amino acid sequence of Cγ4

Sequence Range: 1 to 330

```
          10          20          30          40          50          60
           *           *           *           *           *           *
SGASTKGPSVFPLAPCSRST SESTAALGCLVKDYFPEPVT VSWNSGALTSGVHTFPAVLQ 70          80          90         100         110         120
           *           *           *           *           *           *
SSGLYSLSSVVTVPSSSLGT KTYTCNVDHKPSNTKVDKRV ESKYGPPCPSCPAPEFLGGP 130         140         150         160         170         180
           *           *           *           *           *           *
SVFLFPPKPKDTLMISRTPE VTCVVVDVSQEDPEVQFNWY VDGVEVHNAKTKPREEQFNS 190         200         210         220         230         240
           *           *           *           *           *           *
TYRVVSVLTVLHQDWLNGKE YKCKVSNKGLPSSIEKTISK AKGQPREPQVYTLPPSQEEM 250         260         270         280         290         300
           *           *           *           *           *           *
TKNQVSLTCLVKGFYPSDIA VEWESNGQPENNYKTTPPVL DSDGSFFLYSRLTVDKSRWQ 310         320         330
           *           *           *
EGNVFSCSVMHEALHNHYTQ KSLSLSLGK*
```

Fig. 13.

Amino acid sequence of κ-domain

Sequence Range: 1 to 108

```
            10          20          30          40          50          60
             *           *           *           *           *           *
     SGTVAAPSVFIFPPSDEQLK SGTASVVCLLNNFYPREAKV QWKVDNALQSGNSQESVTEQ 70          80          90         100
             *           *           *           *
     DSKDSTYSLSSTLTLSKADY EKHKVYACEVTHQGLSSPVT KSFNRGEC*
```

Fig. 14.

Amino acid sequence of λ-domain:

Sequence Range: 1 to 107

```
            10          20          30          40          50          60
             *           *           *           *           *           *
     SGPKAAPSVTLFPPSSEELQ ANKATLVCLISDFYPGAVTV AWKADSSPVKAGVETTTPSK 70          80          90         100
             *           *           *           *
     QSNNKYAASSYLSLTPEQWK SHRSYSCQVTHEGSTVEKTV APTECS*
```

Fig.15.
Amino acid sequence of the soluble IL-6Rα domain

Sequence Range: 1 to 360

```
           10          20          30          40          50          60
            *           *           *           *           *           *
   MVAVGCALLAALLAAPGAAL APRRCPAQEVARGVLTSLPG DSVTLTCPGVEPEDNATVHW 70          80          90         100         110         120
            *           *           *           *           *           *
   VLRKPAAGSHPSRWAGMGRR LLLRSVQLHDSGNYSCYRAG RPAGTVHLLVDVPPEEPQLS 130         140         150         160         170         180
            *           *           *           *           *           *
   CFRKSPLSNVVCEWGPRSTP SLTTKAVLLVRKFQNSPAED FQEPCQYSQESQKFSCQLAV 190         200         210         220         230         240
            *           *           *           *           *           *
   PEGDSSFYIVSMCVASSVGS KFSKTQTFQGCGILQPDPPA NITVTAVARNPRWLSVTWQD 250         260         270         280         290         300
            *           *           *           *           *           *
   PHSWNSSFYRLRFELRYRAE RSKTFTTWMVKDLQHHCVIH DAWSGLRHVVQLRAQEEFGQ 310         320         330         340         350         360
            *           *           *           *           *           *
   GEWSEWSPEAMGTPWTESRS PPAENEVSTPMQALTTNKDD DNILFRDSANATSLPVQDAG
```

Fig.16.
Amino acid sequence of the soluble IL-6kα313 domain

Sequence Range: 1 to 315

```
           10          20          30          40          50          60
            *           *           *           *           *           *
   MVAVGCALLAALLAAPGAAL APRRCPAQEVARGVLTSLPG DSVTLTCPGVEPEDNATVHW 70          80          90         100         110         120
            *           *           *           *           *           *
   VLRKPAAGSHPSRWAGMGRR LLLRSVQLHDSGNYSCYRAG RPAGTVHLLVDVPPEEPQLS 130         140         150         160         170         180
            *           *           *           *           *           *
   CFRKSPLSNVVCEWGPRSTP SLTTKAVLLVRKFQNSPAED FQEPCQYSQESQKFSCQLAV 190         200         210         220         230         240
            *           *           *           *           *           *
   PEGDSSFYIVSMCVASSVGS KFSKTQTFQGCGILQPDPPA NITVTAVARNPRWLSVTWQD 250         260         270         280         290         300
            *           *           *           *           *           *
   PHSWNSSFYRLRFELRYRAE RSKTFTTWMVKDLQHHCVIH DAWSGLRHVVQLRAQEEFGQ

310
            *
   GEWSEWSPEAMGTTG
```

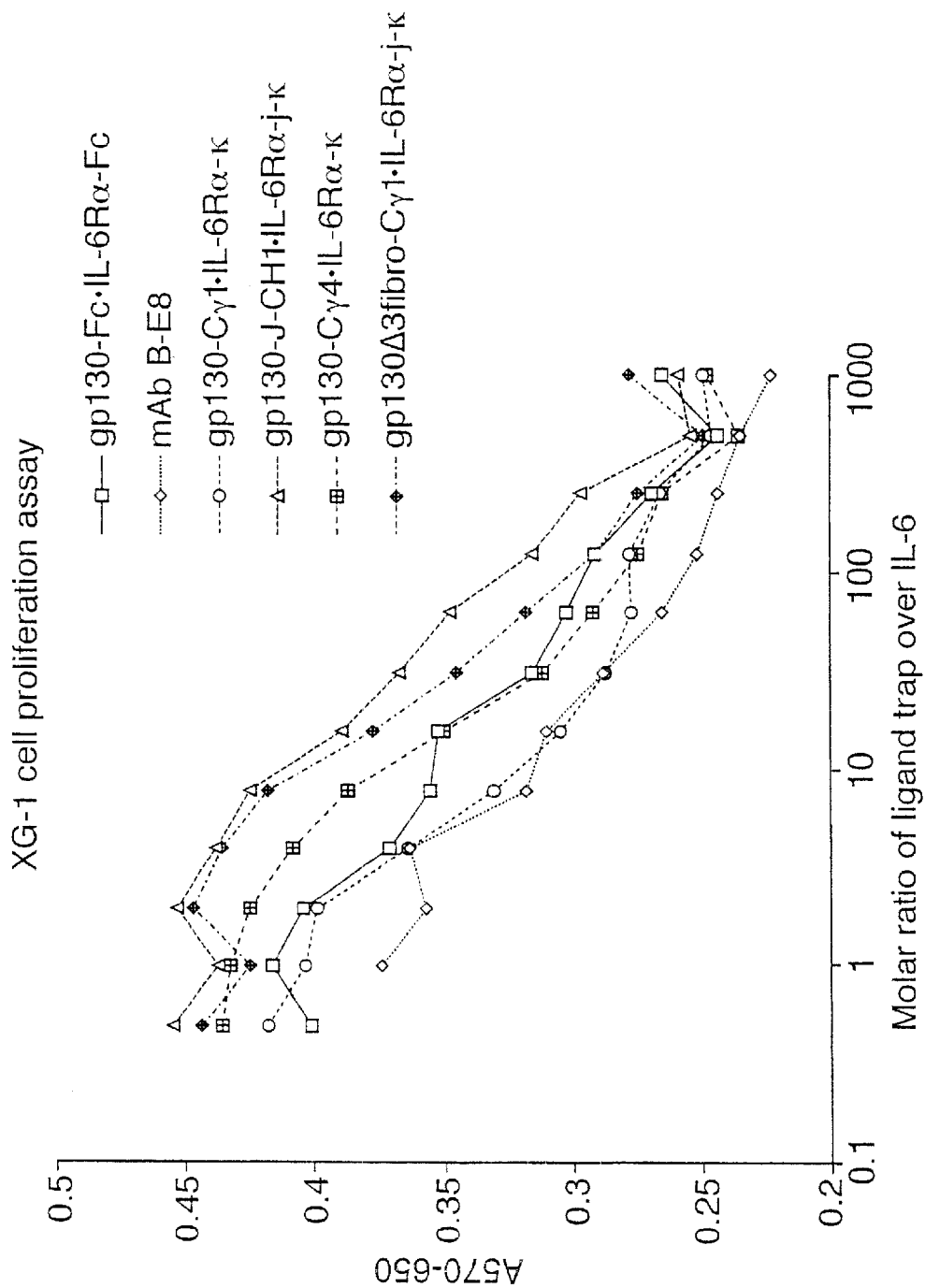

Fig.21A.

```
          10                  20                  30                  40
           *                   *                   *                   *         *
ATG GTG AAG CCA TCA TTA CCA TTC ACA TCC CTC TTA TTC CTG CAG CTG
Met Val Lys Pro Ser Leu Pro Phe Thr Ser Leu Leu Phe Leu Gln Leu>

50                  60                  70                  80                  90
 *                   *                   *                   *                   *
CCC CTG CTG GGA GTG GGG CTG AAC ACG ACA ATT CTG ACG CCC AAT GGG
Pro Leu Leu Gly Val Gly Leu Asn Thr Thr Ile Leu Thr Pro Asn Gly>

100                 110                 120                 130                 140
         *                   *                   *                   *                   *
AAT GAA GAC ACC ACA GCT GAT TTC TTC CTG ACC ACT ATG CCC ACT GAC
Asn Glu Asp Thr Thr Ala Asp Phe Phe Leu Thr Thr Met Pro Thr Asp>

150                 160                 170                 180                 190
            *                   *                   *                   *                   *
TCC CTC AGT GTT TCC ACT CTG CCC CTC CCA GAG GTT CAG TGT TTT GTG
Ser Leu Ser Val Ser Thr Leu Pro Leu Pro Glu Val Gln Cys Phe Val>

200                 210                 220                 230                 240
                 *                   *                   *                   *                   *
TTC AAT GTC GAG TAC ATG AAT TGC ACT TGG AAC AGC AGC TCT GAG CCC
Phe Asn Val Glu Tyr Met Asn Cys Thr Trp Asn Ser Ser Ser Glu Pro>

250                 260                 270                 280
            *                   *                   *                   *         *
CAG CCT ACC AAC CTC ACT CTG CAT TAT TGG TAC AAG AAC TCG GAT AAT
Gln Pro Thr Asn Leu Thr Leu His Tyr Trp Tyr Lys Asn Ser Asp Asn>

290                 300                 310                 320                 330
 *                   *                   *                   *                   *         *
GAT AAA GTC CAG AAG TGC AGC CAC TAT CTA TTC TCT GAA GAA ATC ACT
Asp Lys Val Gln Lys Cys Ser His Tyr Leu Phe Ser Glu Glu Ile Thr>

340                 350                 360                 370                 380
         *                   *                   *                   *                   *
TCT GGC TGT CAG TTG CAA AAA AAG GAG ATC CAC CTC TAC CAA ACA TTT
Ser Gly Cys Gln Leu Gln Lys Lys Glu Ile His Leu Tyr Gln Thr Phe>

*         390                 400                 410                 420                 430
             *                   *                   *                   *                   *
GTT GTT CAG CTC CAG GAC CCA CGG GAA CCC AGG AGA CAG GCC ACA CAG
Val Val Gln Leu Gln Asp Pro Arg Glu Pro Arg Arg Gln Ala Thr Gln>

440                 450                 460                 470                 480
            *                   *                   *                   *                   *
ATG CTA AAA CTG CAG AAT CTG GTG ATC CCC TGG GCT CCA GAG AAC CTA
Met Leu Lys Leu Gln Asn Leu Val Ile Pro Trp Ala Pro Glu Asn Leu>

490                 500                 510                 520
                 *                   *                   *                   *         *
ACA CTT CAC AAA CTG AGT GAA TCC CAG CTA GAA CTG AAC TGG AAC AAC
Thr Leu His Lys Leu Ser Glu Ser Gln Leu Glu Leu Asn Trp Asn Asn>

530                 540                 550                 560                 570
 *                   *                   *                   *                   *         *
AGA TTC TTG AAC CAC TGT TTG GAG CAC TTG GTG CAG TAC CGG ACT GAC
Arg Phe Leu Asn His Cys Leu Glu His Leu Val Gln Tyr Arg Thr Asp>
```

Fig.21B.

```
     580             590             600             610             620
      *       *       *       *       *       *       *       *       *
TGG GAC CAC AGC TGG ACT GAA CAA TCA GTG GAT TAT AGA CAT AAG TTC
Trp Asp His Ser Trp Thr Glu Gln Ser Val Asp Tyr Arg His Lys Phe>

630             640             650             660             670
      *       *       *       *       *       *       *       *       *
TCC TTG CCT AGT GTG GAT GGG CAG AAA CGC TAC ACG TTT CGT GTT CGG
Ser Leu Pro Ser Val Asp Gly Gln Lys Arg Tyr Thr Phe Arg Val Arg>

680             690             700             710             720
          *       *       *       *       *       *       *       *       *
AGC CGC TTT AAC CCA CTC TGT GGA AGT GCT CAG CAT TGG AGT GAA TGG
Ser Arg Phe Asn Pro Leu Cys Gly Ser Ala Gln His Trp Ser Glu Trp>

730             740             750             760
          *       *       *       *       *       *       *       *
AGC CAC CCA ATC CAC TGG GGG AGC AAT ACT TCA AAA GAG AAC GCG TCG
Ser His Pro Ile His Trp Gly Ser Asn Thr Ser Lys Glu Asn Ala Ser>

770             780             790             800             810
 *       *       *       *       *       *       *       *       *       *
TCT GGG AAC ATG AAG GTC CTG CAG GAG CCC ACC TGC GTC TCC GAC TAC
Ser Gly Asn Met Lys Val Leu Gln Glu Pro Thr Cys Val Ser Asp Tyr>

820             830             840             850             860
    *       *       *       *       *       *       *       *       *
ATG AGC ATC TCT ACT TGC GAG TGG AAG ATG AAT GGT CCC ACC AAT TGC
Met Ser Ile Ser Thr Cys Glu Trp Lys Met Asn Gly Pro Thr Asn Cys>

870             880             890             900             910
          *       *       *       *       *       *       *       *       *
AGC ACC GAG CTC CGC CTG TTG TAC CAG CTG GTT TTT CTG CTC TCC GAA
Ser Thr Glu Leu Arg Leu Leu Tyr Gln Leu Val Phe Leu Leu Ser Glu>

920             930             940             950             960
          *       *       *       *       *       *       *       *       *
GCC CAC ACG TGT ATC CCT GAG AAC AAC GGA GGC GCG GGG TGC GTG TGC
Ala His Thr Cys Ile Pro Glu Asn Asn Gly Gly Ala Gly Cys Val Cys>

970             980             990             1000
              *       *       *       *       *       *       *       *
CAC CTG CTC ATG GAT GAC GTG GTC AGT GCG GAT AAC TAT ACA CTG GAC
His Leu Leu Met Asp Asp Val Val Ser Ala Asp Asn Tyr Thr Leu Asp>

1010            1020            1030            1040            1050
  *       *       *       *       *       *       *       *       *       *
CTG TGG GCT GGG CAG CAG CTG CTG TGG AAG GGC TCC TTC AAG CCC AGC
Leu Trp Ala Gly Gln Gln Leu Leu Trp Lys Gly Ser Phe Lys Pro Ser>

1060            1070            1080            1090            1100
      *       *       *       *       *       *       *       *       *
GAG CAT GTG AAA CCC AGG GCC CCA GGA AAC CTG ACA GTT CAC ACC AAT
Glu His Val Lys Pro Arg Ala Pro Gly Asn Leu Thr Val His Thr Asn>

1110            1120            1130            1140            1150
      *       *       *       *       *       *       *       *       *
GTC TCC GAC ACT CTG CTG CTG ACC TGG AGC AAC CCG TAT CCC CCT GAC
Val Ser Asp Thr Leu Leu Leu Thr Trp Ser Asn Pro Tyr Pro Pro Asp>

```
AAT TAC CTG TAT AAT CAT CTC ACC TAT GCA GTC AAC ATT TGG AGT GAA
Asn Tyr Leu Tyr Asn His Leu Thr Tyr Ala Val Asn Ile Trp Ser Glu>
         1210        1220        1230        1240
          *    *      *    *      *    *      *    *      *
AAC GAC CCG GCA GAT TTC AGA ATC TAT AAC GTG ACC TAC CTA GAA CCC
Asn Asp Pro Ala Asp Phe Arg Ile Tyr Asn Val Thr Tyr Leu Glu Pro>
1250        1260        1270        1280        1290
  *    *      *    *      *    *      *    *      *    *
TCC CTC CGC ATC GCA GCC AGC ACC CTG AAG TCT GGG ATT TCC TAC AGG
Ser Leu Arg Ile Ala Ala Ser Thr Leu Lys Ser Gly Ile Ser Tyr Arg>
    1300        1310        1320        1330        1340
      *    *      *    *      *    *      *    *      *
GCA CGG GTG AGG GCC TGG GCT CAG TGC TAT AAC ACC ACC TGG AGT GAG
Ala Arg Val Arg Ala Trp Ala Gln Cys Tyr Asn Thr Thr Trp Ser Glu>
        1350        1360        1370        1380        1390
    *    *      *    *      *    *      *    *      *    *
TGG AGC CCC AGC ACC AAG TGG CAC AAC TCC TAC AGG GAG CCC TTC GAG
Trp Ser Pro Ser Thr Lys Trp His Asn Ser Tyr Arg Glu Pro Phe Glu>
         1400        1410        1420        1430        1440
          *    *      *    *      *    *      *    *      *
CAG TCC GGA GAC AAA ACT CAC ACA TGC CCA CCG TGC CCA GCA CCT GAA
Gln Ser Gly Asp Lys Thr His Thr Cys Pro Pro Cys Pro Ala Pro Glu>
         1450        1460        1470        1480
          *    *      *    *      *    *      *    *
CTC CTG GGG GGA CCG TCA GTC TTC CTC TTC CCC CCA AAA CCC AAG GAC
Leu Leu Gly Gly Pro Ser Val Phe Leu Phe Pro Pro Lys Pro Lys Asp>
1490        1500        1510        1520        1530
  *    *      *    *      *    *      *    *      *    *
ACC CTC ATG ATC TCC CGG ACC CCT GAG GTC ACA TGC GTG GTG GTG GAC
Thr Leu Met Ile Ser Arg Thr Pro Glu Val Thr Cys Val Val Val Asp>
    1540        1550        1560        1570        1580
      *    *      *    *      *    *      *    *      *
GTG AGC CAC GAA GAC CCT GAG GTC AAG TTC AAC TGG TAC GTG GAC GGC
Val Ser His Glu Asp Pro Glu Val Lys Phe Asn Trp Tyr Val Asp Gly>
        1590        1600        1610        1620        1630
    *    *      *    *      *    *      *    *      *    *
GTG GAG GTG CAT AAT GCC AAG ACA AAG CCG CGG GAG GAG CAG TAC AAC
Val Glu Val His Asn Ala Lys Thr Lys Pro Arg Glu Glu Gln Tyr Asn>
         1640        1650        1660        1670        1680
          *    *      *    *      *    *      *    *      *
AGC ACG TAC CGT GTG GTC AGC GTC CTC ACC GTC CTG CAC CAG GAC TGG
Ser Thr Tyr Arg Val Val Ser Val Leu Thr Val Leu His Gln Asp Trp>
             1690        1700        1710        1720
              *    *      *    *      *    *      *    *      *
CTG AAT GGC AAG GAG TAC AAG TGC AAG GTC TCC AAC AAA GCC CTC CCA
Leu Asn Gly Lys Glu Tyr Lys Cys Lys Val Ser Asn Lys Ala Leu Pro>
1730        1740        1750        1760        1770
  *    *      *    *      *    *      *    *      *    *
GCC CCC ATC GAG AAA ACC ATC TCC AAA GCC AAA GGG CAG CCC CGA GAA
Ala Pro Ile Glu Lys Thr Ile Ser Lys Ala Lys Gly Gln Pro Arg Glu>
```

Fig.21D.

```
      1780            1790            1800            1810            1820
        *       *       *       *       *       *       *       *       *
CCA CAG GTG TAC ACC CTG CCC CCA TCC CGG GAG GAG ATG ACC AAG AAC
Pro Gln Val Tyr Thr Leu Pro Pro Ser Arg Glu Glu Met Thr Lys Asn>

1830            1840            1850            1860            1870
    *       *       *       *       *       *       *       *       *       *
CAG GTC AGC CTG ACC TGC CTG GTC AAA GGC TTC TAT CCC AGC GAC ATC
Gln Val Ser Leu Thr Cys Leu Val Lys Gly Phe Tyr Pro Ser Asp Ile>

1880            1890            1900            1910            1920
    *       *       *       *       *       *       *       *       *       *
GCC GTG GAG TGG GAG AGC AAT GGG CAG CCG GAG AAC AAC TAC AAG ACC
Ala Val Glu Trp Glu Ser Asn Gly Gln Pro Glu Asn Asn Tyr Lys Thr>

1930            1940            1950            1960
    *       *       *       *       *       *       *       *       *
ACG CCT CCC GTG CTG GAC TCC GAC GGC TCC TTC TTC CTC TAT AGC AAG
Thr Pro Pro Val Leu Asp Ser Asp Gly Ser Phe Phe Leu Tyr Ser Lys>

1970            1980            1990            2000            2010
  *       *       *       *       *       *       *       *       *       *
CTC ACC GTG GAC AAG AGC AGG TGG CAG CAG GGG AAC GTC TTC TCA TGC
Leu Thr Val Asp Lys Ser Arg Trp Gln Gln Gly Asn Val Phe Ser Cys>

2020            2030            2040            2050            2060
      *       *       *       *       *       *       *       *       *
TCC GTG ATG CAT GAG GCT CTG CAC AAC CAC TAC ACG CAG AAG AGC CTC
Ser Val Met His Glu Ala Leu His Asn His Tyr Thr Gln Lys Ser Leu>

2070            2080
  *       *       *       *       *
TCC CTG TCT CCG GGT AAA TGA
Ser Leu Ser Pro Gly Lys ***>
```

Fig.22A.

```
         10          20          30          40
          *           *           *           *
ATG GTG AAG CCA TCA TTA CCA TTC ACA TCC CTC TTA TTC CTG CAG CTG
Met Val Lys Pro Ser Leu Pro Phe Thr Ser Leu Leu Phe Leu Gln Leu>

50          60          70          80          90
  *           *           *           *           *
CCC CTG CTG GGA GTG GGG CTG AAC ACG ACA ATT CTG ACG CCC AAT GGG
Pro Leu Leu Gly Val Gly Leu Asn Thr Thr Ile Leu Thr Pro Asn Gly>

100         110         120         130         140
     *           *           *           *           *
AAT GAA GAC ACC ACA GCT GAT TTC TTC CTG ACC ACT ATG CCC ACT GAC
Asn Glu Asp Thr Thr Ala Asp Phe Phe Leu Thr Thr Met Pro Thr Asp>

150         160         170         180         190
       *           *           *           *           *
TCC CTC AGT GTT TCC ACT CTG CCC CTC CCA GAG GTT CAG TGT TTT GTG
Ser Leu Ser Val Ser Thr Leu Pro Leu Pro Glu Val Gln Cys Phe Val>

200         210         220         230         240
          *           *           *           *           *
TTC AAT GTC GAG TAC ATG AAT TGC ACT TGG AAC AGC AGC TCT GAG CCC
Phe Asn Val Glu Tyr Met Asn Cys Thr Trp Asn Ser Ser Ser Glu Pro>

250         260         270         280
          *           *           *           *
CAG CCT ACC AAC CTC ACT CTG CAT TAT TGG TAC AAG AAC TCG GAT AAT
Gln Pro Thr Asn Leu Thr Leu His Tyr Trp Tyr Lys Asn Ser Asp Asn>

290         300         310         320         330
 *           *           *           *           *
GAT AAA GTC CAG AAG TGC AGC CAC TAT CTA TTC TCT GAA GAA ATC ACT
Asp Lys Val Gln Lys Cys Ser His Tyr Leu Phe Ser Glu Glu Ile Thr>

340         350         360         370         380
    *           *           *           *           *
TCT GGC TGT CAG TTG CAA AAA AAG GAG ATC CAC CTC TAC CAA ACA TTT
Ser Gly Cys Gln Leu Gln Lys Lys Glu Ile His Leu Tyr Gln Thr Phe>

390         400         410         420         430
       *           *           *           *           *
GTT GTT CAG CTC CAG GAC CCA CGG GAA CCC AGG AGA CAG GCC ACA CAG
Val Val Gln Leu Gln Asp Pro Arg Glu Pro Arg Arg Gln Ala Thr Gln>

440         450         460         470         480
          *           *           *           *           *
ATG CTA AAA CTG CAG AAT CTG GTG ATC CCC TGG GCT CCA GAG AAC CTA
Met Leu Lys Leu Gln Asn Leu Val Ile Pro Trp Ala Pro Glu Asn Leu>

490         500         510         520
             *           *           *           *
ACA CTT CAC AAA CTG AGT GAA TCC CAG CTA GAA CTG AAC TGG AAC AAC
Thr Leu His Lys Leu Ser Glu Ser Gln Leu Glu Leu Asn Trp Asn Asn>

530         540         550         560         570
 *           *           *           *           *
AGA TTC TTG AAC CAC TGT TTG GAG CAC TTG GTG CAG TAC CGG ACT GAC
Arg Phe Leu Asn His Cys Leu Glu His Leu Val Gln Tyr Arg Thr Asp>
```

Fig.22B.

```
      580         590         600         610         620
       *           *           *           *           *
TGG GAC CAC AGC TGG ACT GAA CAA TCA GTG GAT TAT AGA CAT AAG TTC
Trp Asp His Ser Trp Thr Glu Gln Ser Val Asp Tyr Arg His Lys Phe>

630         640         650         660         670
 *     *     *     *     *     *     *     *     *     *
TCC TTG CCT AGT GTG GAT GGG CAG AAA CGC TAC ACG TTT CGT GTT CGG
Ser Leu Pro Ser Val Asp Gly Gln Lys Arg Tyr Thr Phe Arg Val Arg>

680         690         700         710         720
 *     *     *     *     *     *     *     *     *     *
AGC CGC TTT AAC CCA CTC TGT GGA AGT GCT CAG CAT TGG AGT GAA TGG
Ser Arg Phe Asn Pro Leu Cys Gly Ser Ala Gln His Trp Ser Glu Trp>

730         740         750         760
       *     *     *     *     *     *     *     *     *
AGC CAC CCA ATC CAC TGG GGG AGC AAT ACT TCA AAA GAG AAC GGG AAC
Ser His Pro Ile His Trp Gly Ser Asn Thr Ser Lys Glu Asn Gly Asn>

770         780         790         800         810
 *     *     *     *     *     *     *     *     *     *
ATG AAG GTC CTG CAG GAG CCC ACC TGC GTC TCC GAC TAC ATG AGC ATC
Met Lys Val Leu Gln Glu Pro Thr Cys Val Ser Asp Tyr Met Ser Ile>

820         830         840         850         860
 *     *     *     *     *     *     *     *     *     *
TCT ACT TGC GAG TGG AAG ATG AAT GGT CCC ACC AAT TGC AGC ACC GAG
Ser Thr Cys Glu Trp Lys Met Asn Gly Pro Thr Asn Cys Ser Thr Glu>

870         880         890         900         910
 *     *     *     *     *     *     *     *     *     *
CTC CGC CTG TTG TAC CAG CTG GTT TTT CTG CTC TCC GAA GCC CAC ACG
Leu Arg Leu Leu Tyr Gln Leu Val Phe Leu Leu Ser Glu Ala His Thr>

920         930         940         950         960
 *     *     *     *     *     *     *     *     *     *
TGT ATC CCT GAG AAC AAC GGA GGC GCG GGG TGC GTG TGC CAC CTG CTC
Cys Ile Pro Glu Asn Asn Gly Gly Ala Gly Cys Val Cys His Leu Leu>

970         980         990         1000
       *     *     *     *     *     *     *     *     *
ATG GAT GAC GTG GTC AGT GCG GAT AAC TAT ACA CTG GAC CTG TGG GCT
Met Asp Asp Val Val Ser Ala Asp Asn Tyr Thr Leu Asp Leu Trp Ala>

1010        1020        1030        1040        1050
 *     *     *     *     *     *     *     *     *     *
GGG CAG CAG CTG CTG TGG AAG GGC TCC TTC AAG CCC AGC GAG CAT GTG
Gly Gln Gln Leu Leu Trp Lys Gly Ser Phe Lys Pro Ser Glu His Val>

1060        1070        1080        1090        1100
 *     *     *     *     *     *     *     *     *     *
AAA CCC AGG GCC CCA GGA AAC CTG ACA GTT CAC ACC AAT GTC TCC GAC
Lys Pro Arg Ala Pro Gly Asn Leu Thr Val His Thr Asn Val Ser Asp>

1110        1120        1130        1140        1150
 *     *     *     *     *     *     *     *     *     *
ACT CTG CTG CTG ACC TGG AGC AAC CCG TAT CCC CCT GAC AAT TAC CTG
Thr Leu Leu Leu Thr Trp Ser Asn Pro Tyr Pro Pro Asp Asn Tyr Leu>

```
TAT AAT CAT CTC ACC TAT GCA GTC AAC ATT TGG AGT GAA AAC GAC CCG
Tyr Asn His Leu Thr Tyr Ala Val Asn Ile Trp Ser Glu Asn Asp Pro>
            1210          1220          1230          1240
              *             *             *             *       *
GCA GAT TTC AGA ATC TAT AAC GTG ACC TAC CTA GAA CCC TCC CTC CGC
Ala Asp Phe Arg Ile Tyr Asn Val Thr Tyr Leu Glu Pro Ser Leu Arg>
 1250          1260          1270          1280          1290
   *     *     *     *     *     *     *     *     *     *     *
ATC GCA GCC AGC ACC CTG AAG TCT GGG ATT TCC TAC AGG GCA CGG GTG
Ile Ala Ala Ser Thr Leu Lys Ser Gly Ile Ser Tyr Arg Ala Arg Val>
      1300          1310          1320          1330          1340
        *             *             *             *             *
AGG GCC TGG GCT CAG AGC TAT AAC ACC ACC TGG AGT GAG TGG AGC CCC
Arg Ala Trp Ala Gln Ser Tyr Asn Thr Thr Trp Ser Glu Trp Ser Pro>
            1350          1360          1370          1380          1390
              *             *             *             *             *
AGC ACC AAG TGG CAC AAC TCC TAC AGG GAG CCC TTC GAG CAG TCC GGA
Ser Thr Lys Trp His Asn Ser Tyr Arg Glu Pro Phe Glu Gln Ser Gly>
            1400          1410          1420          1430          1440
              *             *             *             *             *
GAC AAA ACT CAC ACA TGC CCA CCG TGC CCA GCA CCT GAA CTC CTG GGG
Asp Lys Thr His Thr Cys Pro Pro Cys Pro Ala Pro Glu Leu Leu Gly>
            1450          1460          1470          1480
              *             *             *             *       *
GGA CCG TCA GTC TTC CTC TTC CCC CCA AAA CCC AAG GAC ACC CTC ATG
Gly Pro Ser Val Phe Leu Phe Pro Pro Lys Pro Lys Asp Thr Leu Met>
 1490          1500          1510          1520          1530
   *     *     *     *     *     *     *     *     *     *     *
ATC TCC CGG ACC CCT GAG GTC ACA TGC GTG GTG GTG GAC GTG AGC CAC
Ile Ser Arg Thr Pro Glu Val Thr Cys Val Val Val Asp Val Ser His>
      1540          1550          1560          1570          1580
        *             *             *             *             *
GAA GAC CCT GAG GTC AAG TTC AAC TGG TAC GTG GAC GGC GTG GAG GTG
Glu Asp Pro Glu Val Lys Phe Asn Trp Tyr Val Asp Gly Val Glu Val>
            1590          1600          1610          1620          1630
              *             *             *             *             *
CAT AAT GCC AAG ACA AAG CCG CGG GAG GAG CAG TAC AAC AGC ACG TAC
His Asn Ala Lys Thr Lys Pro Arg Glu Glu Gln Tyr Asn Ser Thr Tyr>
            1640          1650          1660          1670          1680
              *             *             *             *             *
CGT GTG GTC AGC GTC CTC ACC GTC CTG CAC CAG GAC TGG CTG AAT GGC
Arg Val Val Ser Val Leu Thr Val Leu His Gln Asp Trp Leu Asn Gly>
            1690          1700          1710          1720
              *             *             *             *       *
AAG GAG TAC AAG TGC AAG GTC TCC AAC AAA GCC CTC CCA GCC CCC ATC
Lys Glu Tyr Lys Cys Lys Val Ser Asn Lys Ala Leu Pro Ala Pro Ile>
 1730          1740          1750          1760          1770
   *     *     *     *     *     *     *     *     *     *     *
GAG AAA ACC ATC TCC AAA GCC AAA GGG CAG CCC CGA GAA CCA CAG GTG
Glu Lys Thr Ile Ser Lys Ala Lys Gly Gln Pro Arg Glu Pro Gln Val>
```

Fig.22D.

```
      1780          1790          1800          1810          1820
   *     *     *     *     *     *     *     *     *     *
TAC  ACC  CTG  CCC  CCA  TCC  CGG  GAT  GAG  CTG  ACC  AAG  AAC  CAG  GTC  AGC
Tyr  Thr  Leu  Pro  Pro  Ser  Arg  Asp  Glu  Leu  Thr  Lys  Asn  Gln  Val  Ser>

1830          1840          1850          1860          1870
   *     *     *     *     *     *     *     *     *     *
CTG  ACC  TGC  CTG  GTC  AAA  GGC  TTC  TAT  CCC  AGC  GAC  ATC  GCC  GTG  GAG
Leu  Thr  Cys  Leu  Val  Lys  Gly  Phe  Tyr  Pro  Ser  Asp  Ile  Ala  Val  Glu>

1880          1890          1900          1910          1920
   *     *     *     *     *     *     *     *     *     *
TGG  GAG  AGC  AAT  GGG  CAG  CCG  GAG  AAC  AAC  TAC  AAG  ACC  ACG  CCT  CCC
Trp  Glu  Ser  Asn  Gly  Gln  Pro  Glu  Asn  Asn  Tyr  Lys  Thr  Thr  Pro  Pro>

1930          1940          1950          1960
   *     *     *     *     *     *     *     *     *     *
GTG  CTG  GAC  TCC  GAC  GGC  TCC  TTC  TTC  CTC  TAT  AGC  AAG  CTC  ACC  GTG
Val  Leu  Asp  Ser  Asp  Gly  Ser  Phe  Phe  Leu  Tyr  Ser  Lys  Leu  Thr  Val>

1970          1980          1990          2000          2010
   *     *     *     *     *     *     *     *     *     *
GAC  AAG  AGC  AGG  TGG  CAG  CAG  GGG  AAC  GTC  TTC  TCA  TGC  TCC  GTG  ATG
Asp  Lys  Ser  Arg  Trp  Gln  Gln  Gly  Asn  Val  Phe  Ser  Cys  Ser  Val  Met>

2020          2030          2040          2050          2060
   *     *     *     *     *     *     *     *     *     *
CAT  GAG  GCT  CTG  CAC  AAC  CAC  TAC  ACG  CAG  AAG  AGC  CTC  TCC  CTG  TCT
His  Glu  Ala  Leu  His  Asn  His  Tyr  Thr  Gln  Lys  Ser  Leu  Ser  Leu  Ser>

2070
   *     *     *
CCG  GGT  AAA  TGA
Pro  Gly  Lys  ***>
```

Fig.23A.

```
           10              20              30              40
    *       *       *       *       *       *       *       *       *
ATG GTG AAG CCA TCA TTA CCA TTC ACA TCC CTC TTA TTC CTG CAG CTG
Met Val Lys Pro Ser Leu Pro Phe Thr Ser Leu Leu Phe Leu Gln Leu>

50              60              70              80              90
    *       *       *       *       *       *       *       *       *       *
CCC CTG CTG GGA GTG GGG CTG AAC ACG ACA ATT CTG ACG CCC AAT GGG
Pro Leu Leu Gly Val Gly Leu Asn Thr Thr Ile Leu Thr Pro Asn Gly>

100             110             120             130             140
    *       *       *       *       *       *       *       *       *
AAT GAA GAC ACC ACA GCT GAT TTC TTC CTG ACC ACT ATG CCC ACT GAC
Asn Glu Asp Thr Thr Ala Asp Phe Phe Leu Thr Thr Met Pro Thr Asp>

150             160             170             180             190
    *       *       *       *       *       *       *       *       *       *
TCC CTC AGT GTT TCC ACT CTG CCC CTC CCA GAG GTT CAG TGT TTT GTG
Ser Leu Ser Val Ser Thr Leu Pro Leu Pro Glu Val Gln Cys Phe Val>

200             210             220             230             240
    *       *       *       *       *       *       *       *       *       *
TTC AAT GTC GAG TAC ATG AAT TGC ACT TGG AAC AGC AGC TCT GAG CCC
Phe Asn Val Glu Tyr Met Asn Cys Thr Trp Asn Ser Ser Ser Glu Pro>

250             260             270             280
    *       *       *       *       *       *       *       *       *
CAG CCT ACC AAC CTC ACT CTG CAT TAT TGG TAC AAG AAC TCG GAT AAT
Gln Pro Thr Asn Leu Thr Leu His Tyr Trp Tyr Lys Asn Ser Asp Asn>

290             300             310             320             330
    *       *       *       *       *       *       *       *       *       *
GAT AAA GTC CAG AAG TGC AGC CAC TAT CTA TTC TCT GAA GAA ATC ACT
Asp Lys Val Gln Lys Cys Ser His Tyr Leu Phe Ser Glu Glu Ile Thr>

340             350             360             370             380
    *       *       *       *       *       *       *       *       *
TCT GGC TGT CAG TTG CAA AAA AAG GAG ATC CAC CTC TAC CAA ACA TTT
Ser Gly Cys Gln Leu Gln Lys Lys Glu Ile His Leu Tyr Gln Thr Phe>

390             400             410             420             430
    *       *       *       *       *       *       *       *       *       *
GTT GTT CAG CTC CAG GAC CCA CGG GAA CCC AGG AGA CAG GCC ACA CAG
Val Val Gln Leu Gln Asp Pro Arg Glu Pro Arg Arg Gln Ala Thr Gln>

440             450             460             470             480
    *       *       *       *       *       *       *       *       *       *
ATG CTA AAA CTG CAG AAT CTG GTG ATC CCC TGG GCT CCA GAG AAC CTA
Met Leu Lys Leu Gln Asn Leu Val Ile Pro Trp Ala Pro Glu Asn Leu>

490             500             510             520
    *       *       *       *       *       *       *       *       *
ACA CTT CAC AAA CTG AGT GAA TCC CAG CTA GAA CTG AAC TGG AAC AAC
Thr Leu His Lys Leu Ser Glu Ser Gln Leu Glu Leu Asn Trp Asn Asn>

530             540             550             560             570
    *       *       *       *       *       *       *       *       *       *
AGA TTC TTG AAC CAC TGT TTG GAG CAC TTG GTG CAG TAC CGG ACT GAC
Arg Phe Leu Asn His Cys Leu Glu His Leu Val Gln Tyr Arg Thr Asp>
```

Fig.23B.

```
        580           590           600           610           620
          *             *             *             *             *
TGG  GAC  CAC  AGC  TGG  ACT  GAA  CAA  TCA  GTG  GAT  TAT  AGA  CAT  AAG  TTC
Trp  Asp  His  Ser  Trp  Thr  Glu  Gln  Ser  Val  Asp  Tyr  Arg  His  Lys  Phe>

630           640           650           660           670
          *             *             *             *             *
TCC  TTG  CCT  AGT  GTG  GAT  GGG  CAG  AAA  CGC  TAC  ACG  TTT  CGT  GTT  CGG
Ser  Leu  Pro  Ser  Val  Asp  Gly  Gln  Lys  Arg  Tyr  Thr  Phe  Arg  Val  Arg>

680           690           700           710           720
          *             *             *             *             *
AGC  CGC  TTT  AAC  CCA  CTC  TGT  GGA  AGT  GCT  CAG  CAT  TGG  AGT  GAA  TGG
Ser  Arg  Phe  Asn  Pro  Leu  Cys  Gly  Ser  Ala  Gln  His  Trp  Ser  Glu  Trp>

730           740           750           760
          *             *             *             *             *
AGC  CAC  CCA  ATC  CAC  TGG  GGG  AGC  AAT  ACT  TCA  AAA  GAG  AAC  GCG  TCG
Ser  His  Pro  Ile  His  Trp  Gly  Ser  Asn  Thr  Ser  Lys  Glu  Asn  Ala  Ser>

770           780           790           800           810
  *             *             *             *             *             *
TCT  GGG  AAC  ATG  AAG  GTC  CTG  CAG  GAG  CCC  ACC  TGC  GTC  TCC  GAC  TAC
Ser  Gly  Asn  Met  Lys  Val  Leu  Gln  Glu  Pro  Thr  Cys  Val  Ser  Asp  Tyr>

820           830           840           850           860
          *             *             *             *             *
ATG  AGC  ATC  TCT  ACT  TGC  GAG  TGG  AAG  ATG  AAT  GGT  CCC  ACC  AAT  TGC
Met  Ser  Ile  Ser  Thr  Cys  Glu  Trp  Lys  Met  Asn  Gly  Pro  Thr  Asn  Cys>

870           880           890           900           910
          *             *             *             *             *
AGC  ACC  GAG  CTC  CGC  CTG  TTG  TAC  CAG  CTG  GTT  TTT  CTG  CTC  TCC  GAA
Ser  Thr  Glu  Leu  Arg  Leu  Leu  Tyr  Gln  Leu  Val  Phe  Leu  Leu  Ser  Glu>

920           930           940           950           960
          *             *             *             *             *
GCC  CAC  ACG  TGT  ATC  CCT  GAG  AAC  AAC  GGA  GGC  GCG  GGG  TGC  GTG  TGC
Ala  His  Thr  Cys  Ile  Pro  Glu  Asn  Asn  Gly  Gly  Ala  Gly  Cys  Val  Cys>

970           980           990           1000
          *             *             *             *             *
CAC  CTG  CTC  ATG  GAT  GAC  GTG  GTC  AGT  GCG  GAT  AAC  TAT  ACA  CTG  GAC
His  Leu  Leu  Met  Asp  Asp  Val  Val  Ser  Ala  Asp  Asn  Tyr  Thr  Leu  Asp>

1010          1020          1030          1040          1050
  *             *             *             *             *             *
CTG  TGG  GCT  GGG  CAG  CAG  CTG  CTG  TGG  AAG  GGC  TCC  TTC  AAG  CCC  AGC
Leu  Trp  Ala  Gly  Gln  Gln  Leu  Leu  Trp  Lys  Gly  Ser  Phe  Lys  Pro  Ser>

1060          1070          1080          1090          1100
          *             *             *             *             *
GAG  CAT  GTG  AAA  CCC  AGG  GCC  CCA  GGA  AAC  CTG  ACA  GTT  CAC  ACC  AAT
Glu  His  Val  Lys  Pro  Arg  Ala  Pro  Gly  Asn  Leu  Thr  Val  His  Thr  Asn>

1110          1120          1130          1140          1150
          *             *             *             *             *
GTC  TCC  GAC  ACT  CTG  CTG  CTG  ACC  TGG  AGC  AAC  CCG  TAT  CCC  CCT  GAC
Val  Ser  Asp  Thr  Leu  Leu  Leu  Thr  Trp  Ser  Asn  Pro  Tyr  Pro  Pro  Asp>

```
          AAT TAC CTG TAT AAT CAT CTC ACC TAT GCA GTC AAC ATT TGG AGT GAA
          Asn Tyr Leu Tyr Asn His Leu Thr Tyr Ala Val Asn Ile Trp Ser Glu>
                   1210        1220        1230        1240
                    *     *     *     *     *     *     *     *     *
          AAC GAC CCG GCA GAT TTC AGA ATC TAT AAC GTG ACC TAC CTA GAA CCC
          Asn Asp Pro Ala Asp Phe Arg Ile Tyr Asn Val Thr Tyr Leu Glu Pro>
   1250        1260        1270        1280        1290
     *     *     *     *     *     *     *     *     *     *
          TCC CTC CGC ATC GCA GCC AGC ACC CTG AAG TCT GGG ATT TCC TAC AGG
          Ser Leu Arg Ile Ala Ala Ser Thr Leu Lys Ser Gly Ile Ser Tyr Arg>
               1300        1310        1320        1330        1340
                 *     *     *     *     *     *     *     *     *
          GCA CGG GTG AGG GCC TGG GCT CAG AGC TAT AAC ACC ACC TGG AGT GAG
          Ala Arg Val Arg Ala Trp Ala Gln Ser Tyr Asn Thr Thr Trp Ser Glu>
                   1350        1360        1370        1380        1390
                    *     *     *     *     *     *     *     *     *
          TGG AGC CCC AGC ACC AAG TGG CAC AAC TCC TAC AGG GAG CCC TTC GAG
          Trp Ser Pro Ser Thr Lys Trp His Asn Ser Tyr Arg Glu Pro Phe Glu>
                   1400        1410        1420        1430        1440
                    *     *     *     *     *     *     *     *     *     *
          CAG TCC GGA GAC AAA ACT CAC ACA TGC CCA CCG TGC CCA GCA CCT GAA
          Gln Ser Gly Asp Lys Thr His Thr Cys Pro Pro Cys Pro Ala Pro Glu>
                        1450        1460        1470        1480
                         *     *     *     *     *     *     *     *     *
          CTC CTG GGG GGA CCG TCA GTC TTC CTC TTC CCC CCA AAA CCC AAG GAC
          Leu Leu Gly Gly Pro Ser Val Phe Leu Phe Pro Pro Lys Pro Lys Asp>
   1490        1500        1510        1520        1530
     *     *     *     *     *     *     *     *     *     *
          ACC CTC ATG ATC TCC CGG ACC CCT GAG GTC ACA TGC GTG GTG GTG GAC
          Thr Leu Met Ile Ser Arg Thr Pro Glu Val Thr Cys Val Val Val Asp>
             1540        1550        1560        1570        1580
                *     *     *     *     *     *     *     *     *
          GTG AGC CAC GAA GAC CCT GAG GTC AAG TTC AAC TGG TAC GTG GAC GGC
          Val Ser His Glu Asp Pro Glu Val Lys Phe Asn Trp Tyr Val Asp Gly>
                   1590        1600        1610        1620        1630
                    *     *     *     *     *     *     *     *     *     *
          GTG GAG GTG CAT AAT GCC AAG ACA AAG CCG CGG GAG GAG CAG TAC AAC
          Val Glu Val His Asn Ala Lys Thr Lys Pro Arg Glu Glu Gln Tyr Asn>
                        1640        1650        1660        1670        1680
                         *     *     *     *     *     *     *     *     *     *
          AGC ACG TAC CGT GTG GTC AGC GTC CTC ACC GTC CTG CAC CAG GAC TGG
          Ser Thr Tyr Arg Val Val Ser Val Leu Thr Val Leu His Gln Asp Trp>
                             1690        1700        1710        1720
                              *     *     *     *     *     *     *     *     *
          CTG AAT GGC AAG GAG TAC AAG TGC AAG GTC TCC AAC AAA GCC CTC CCA
          Leu Asn Gly Lys Glu Tyr Lys Cys Lys Val Ser Asn Lys Ala Leu Pro>
   1730        1740        1750        1760        1770
     *     *     *     *     *     *     *     *     *     *
          GCC CCC ATC GAG AAA ACC ATC TCC AAA GCC AAA GGG CAG CCC CGA GAA
          Ala Pro Ile Glu Lys Thr Ile Ser Lys Ala Lys Gly Gln Pro Arg Glu>
```

Fig. 23D.

```
         1780           1790          1800          1810          1820
           *        *     *        *     *        *     *        *     *
CCA CAG GTG TAC ACC CTG CCC CCA TCC CGG GAT GAG CTG ACC AAG AAC
Pro Gln Val Tyr Thr Leu Pro Pro Ser Arg Asp Glu Leu Thr Lys Asn>

1830           1840          1850          1860          1870
  *        *     *        *     *        *     *        *     *        *
CAG GTC AGC CTG ACC TGC CTG GTC AAA GGC TTC TAT CCC AGC GAC ATC
Gln Val Ser Leu Thr Cys Leu Val Lys Gly Phe Tyr Pro Ser Asp Ile>

1880           1890          1900          1910          1920
  *        *     *        *     *        *     *        *     *        *
GCC GTG GAG TGG GAG AGC AAT GGG CAG CCG GAG AAC AAC TAC AAG ACC
Ala Val Glu Trp Glu Ser Asn Gly Gln Pro Glu Asn Asn Tyr Lys Thr>

1930          1940          1950          1960
        *        *     *        *     *        *     *        *     *
ACG CCT CCC GTG CTG GAC TCC GAC GGC TCC TTC TTC CTC TAT AGC AAG
Thr Pro Pro Val Leu Asp Ser Asp Gly Ser Phe Phe Leu Tyr Ser Lys>

1970          1980          1990          2000          2010
    *     *        *     *        *     *        *     *        *     *
CTC ACC GTG GAC AAG AGC AGG TGG CAG CAG GGG AAC GTC TTC TCA TGC
Leu Thr Val Asp Lys Ser Arg Trp Gln Gln Gly Asn Val Phe Ser Cys>

2020          2030          2040          2050          2060
        *     *        *     *        *     *        *     *        *
TCC GTG ATG CAT GAG GCT CTG CAC AAC CAC TAC ACG CAG AAG AGC CTC
Ser Val Met His Glu Ala Leu His Asn His Tyr Thr Gln Lys Ser Leu>

2070          2080
  *        *     *        *     *
TCC CTG TCT CCG GGT AAA TGA
Ser Leu Ser Pro Gly Lys ***>
```

Fig.24A.

```
         10           20          30          40
          *            *           *           *
ATG GTG GCC GTC GGC TGC GCG CTG CTG GCT GCC CTG CTG GCC GCG CCG
Met Val Ala Val Gly Cys Ala Leu Leu Ala Ala Leu Leu Ala Ala Pro>

50          60          70          80          90
  *           *           *           *           *
GGA GCG GCG CTG GCC CCA AGG CGC TGC CCT GCG CAG GAG GTG GCA AGA
Gly Ala Ala Leu Ala Pro Arg Arg Cys Pro Ala Gln Glu Val Ala Arg>

100         110         120         130         140
     *           *           *           *           *
GGC GTG CTG ACC AGT CTG CCA GGA GAC AGC GTG ACT CTG ACC TGC CCG
Gly Val Leu Thr Ser Leu Pro Gly Asp Ser Val Thr Leu Thr Cys Pro>

150         160         170         180         190
        *           *           *           *           *
GGG GTA GAG CCG GAA GAC AAT GCC ACT GTT CAC TGG GTG CTC AGG AAG
Gly Val Glu Pro Glu Asp Asn Ala Thr Val His Trp Val Leu Arg Lys>

200         210         220         230         240
            *           *           *           *           *
CCG GCT GCA GGC TCC CAC CCC AGC AGA TGG GCT GGC ATG GGA AGG AGG
Pro Ala Ala Gly Ser His Pro Ser Arg Trp Ala Gly Met Gly Arg Arg>

250         260         270         280
              *           *           *           *
CTG CTG CTG AGG TCG GTG CAG CTC CAC GAC TCT GGA AAC TAT TCA TGC
Leu Leu Leu Arg Ser Val Gln Leu His Asp Ser Gly Asn Tyr Ser Cys>

290         300         310         320         330
 *           *           *           *           *
TAC CGG GCC GGC CGC CCA GCT GGG ACT GTG CAC TTG CTG GTG GAT GTT
Tyr Arg Ala Gly Arg Pro Ala Gly Thr Val His Leu Leu Val Asp Val>

340         350         360         370         380
       *           *           *           *           *
CCC CCC GAG GAG CCC CAG CTC TCC TGC TTC CGG AAG AGC CCC CTC AGC
Pro Pro Glu Glu Pro Gln Leu Ser Cys Phe Arg Lys Ser Pro Leu Ser>

390         400         410         420         430
          *           *           *           *           *
AAT GTT GTT TGT GAG TGG GGT CCT CGG AGC ACC CCA TCC CTG ACG ACA
Asn Val Val Cys Glu Trp Gly Pro Arg Ser Thr Pro Ser Leu Thr Thr>

440         450         460         470         480
             *           *           *           *           *
AAG GCT GTG CTC TTG GTG AGG AAG TTT CAG AAC AGT CCG GCC GAA GAC
Lys Ala Val Leu Leu Val Arg Lys Phe Gln Asn Ser Pro Ala Glu Asp>

490         500         510         520
                *           *           *           *
TTC CAG GAG CCG TGC CAG TAT TCC CAG GAG TCC CAG AAG TTC TCC TGC
Phe Gln Glu Pro Cys Gln Tyr Ser Gln Glu Ser Gln Lys Phe Ser Cys>

530         540         550         560         570
 *           *           *           *           *
CAG TTA GCA GTC CCG GAG GGA GAC AGC TCT TTC TAC ATA GTG TCC ATG
Gln Leu Ala Val Pro Glu Gly Asp Ser Ser Phe Tyr Ile Val Ser Met>
```

Fig.24B.

```
      580             590             600             610             620
       *       *       *       *       *       *       *       *       *
      TGC GTC GCC AGT AGT GTC GGG AGC AAG TTC AGC AAA ACT CAA ACC TTT
      Cys Val Ala Ser Ser Val Gly Ser Lys Phe Ser Lys Thr Gln Thr Phe>

630             640             650             660             670
               *       *       *       *       *       *       *       *       *       *
      CAG GGT TGT GGA ATC TTG CAG CCT GAT CCG CCT GCC AAC ATC ACA GTC
      Gln Gly Cys Gly Ile Leu Gln Pro Asp Pro Pro Ala Asn Ile Thr Val>

680             690             700             710             720
               *       *       *       *       *       *       *       *       *
      ACT GCC GTG GCC AGA AAC CCC CGC TGG CTC AGT GTC ACC TGG CAA GAC
      Thr Ala Val Ala Arg Asn Pro Arg Trp Leu Ser Val Thr Trp Gln Asp>

730             740             750             760
                       *       *       *       *       *       *       *       *
      CCC CAC TCC TGG AAC TCA TCT TTC TAC AGA CTA CGG TTT GAG CTC AGA
      Pro His Ser Trp Asn Ser Ser Phe Tyr Arg Leu Arg Phe Glu Leu Arg>

770             780             790             800             810
       *       *       *       *       *       *       *       *       *
      TAT CGG GCT GAA CGG TCA AAG ACA TTC ACA ACA TGG ATG GTC AAG GAC
      Tyr Arg Ala Glu Arg Ser Lys Thr Phe Thr Thr Trp Met Val Lys Asp>

820             830             840             850             860
               *       *       *       *       *       *       *       *       *
      CTC CAG CAT CAC TGT GTC ATC CAC GAC GCC TGG AGC GGC CTG AGG CAC
      Leu Gln His His Cys Val Ile His Asp Ala Trp Ser Gly Leu Arg His>

870             880             890             900             910
               *       *       *       *       *       *       *       *       *
      GTG GTG CAG CTT CGT GCC CAG GAG GAG TTC GGG CAA GGC GAG TGG AGC
      Val Val Gln Leu Arg Ala Gln Glu Glu Phe Gly Gln Gly Glu Trp Ser>

920             930             940             950             960
               *       *       *       *       *       *       *       *       *
      GAG TGG AGC CCG GAG GCC ATG GGC ACG CCT TGG ACA GAA TCC AGG AGT
      Glu Trp Ser Pro Glu Ala Met Gly Thr Pro Trp Thr Glu Ser Arg Ser>

970             980             990             1000
                       *       *       *       *       *       *       *       *       *
      CCT CCA GCT GAG AAC GAG GTG TCC ACC CCC ATG ACC GGT GGC GCG CCT
      Pro Pro Ala Glu Asn Glu Val Ser Thr Pro Met Thr Gly Gly Ala Pro>

1010            1020            1030            1040            1050
       *       *       *       *       *       *       *       *       *       *
      TCA GGT GCT CAG CTG GAA CTT CTA GAC CCA TGT GGT TAT ATC AGT CCT
      Ser Gly Ala Gln Leu Glu Leu Leu Asp Pro Cys Gly Tyr Ile Ser Pro>

1060            1070            1080            1090            1100
               *       *       *       *       *       *       *       *       *
      GAA TCT CCA GTT GTA CAA CTT CAT TCT AAT TTC ACT GCA GTT TGT GTG
      Glu Ser Pro Val Val Gln Leu His Ser Asn Phe Thr Ala Val Cys Val>

1110            1120            1130            1140            1150
               *       *       *       *       *       *       *       *       *
      CTA AAG GAA AAA TGT ATG GAT TAT TTT CAT GTA AAT GCT AAT TAC ATT
      Leu Lys Glu Lys Cys Met Asp Tyr Phe His Val Asn Ala Asn Tyr Ile>

```
    GTC TGG AAA ACA AAC CAT TTT ACT ATT CCT AAG GAG CAA TAT ACT ATC
    Val Trp Lys Thr Asn His Phe Thr Ile Pro Lys Glu Gln Tyr Thr Ile>
             1210        1220        1230        1240
          *     *     *     *     *     *     *     *     *
    ATA AAC AGA ACA GCA TCC AGT GTC ACC TTT ACA GAT ATA GCT TCA TTA
    Ile Asn Arg Thr Ala Ser Ser Val Thr Phe Thr Asp Ile Ala Ser Leu>
1250        1260        1270        1280        1290
    *     *     *     *     *     *     *     *     *     *
    AAT ATT CAG CTC ACT TGC AAC ATT CTT ACA TTC GGA CAG CTT GAA CAG
    Asn Ile Gln Leu Thr Cys Asn Ile Leu Thr Phe Gly Gln Leu Glu Gln>
          1300        1310        1320        1330        1340
       *     *     *     *     *     *     *     *     *
    AAT GTT TAT GGA ATC ACA ATA ATT TCA GGC TTG CCT CCA GAA AAA CCT
    Asn Val Tyr Gly Ile Thr Ile Ile Ser Gly Leu Pro Pro Glu Lys Pro>
             1350        1360        1370        1380        1390
          *     *     *     *     *     *     *     *     *     *
    AAA AAT TTG AGT TGC ATT GTG AAC GAG GGG AAG AAA ATG AGG TGT GAG
    Lys Asn Leu Ser Cys Ile Val Asn Glu Gly Lys Lys Met Arg Cys Glu>
                1400        1410        1420        1430        1440
          *     *     *     *     *     *     *     *     *     *
    TGG GAT GGT GGA AGG GAA ACA CAC TTG GAG ACA AAC TTC ACT TTA AAA
    Trp Asp Gly Gly Arg Glu Thr His Leu Glu Thr Asn Phe Thr Leu Lys>
                1450        1460        1470        1480
             *     *     *     *     *     *     *     *     *
    TCT GAA TGG GCA ACA CAC AAG TTT GCT GAT TGC AAA GCA AAA CGT GAC
    Ser Glu Trp Ala Thr His Lys Phe Ala Asp Cys Lys Ala Lys Arg Asp>
1490        1500        1510        1520        1530        *
    *     *     *     *     *     *     *     *     *     *
    ACC CCC ACC TCA TGC ACT GTT GAT TAT TCT ACT GTG TAT TTT GTC AAC
    Thr Pro Thr Ser Cys Thr Val Asp Tyr Ser Thr Val Tyr Phe Val Asn>
          1540        1550        1560        1570        1580
       *     *     *     *     *     *     *     *     *
    ATT GAA GTC TGG GTA GAA GCA GAG AAT GCC CTT GGG AAG GTT ACA TCA
    Ile Glu Val Trp Val Glu Ala Glu Asn Ala Leu Gly Lys Val Thr Ser>
             1590        1600        1610        1620        1630
          *     *     *     *     *     *     *     *     *     *
    GAT CAT ATC AAT TTT GAT CCT GTA TAT AAA GTG AAG CCC AAT CCG CCA
    Asp His Ile Asn Phe Asp Pro Val Tyr Lys Val Lys Pro Asn Pro Pro>
                1640        1650        1660        1670        1680
          *     *     *     *     *     *     *     *     *     *
    CAT AAT TTA TCA GTG ATC AAC TCA GAG GAA CTG TCT AGT ATC TTA AAA
    His Asn Leu Ser Val Ile Asn Ser Glu Glu Leu Ser Ser Ile Leu Lys>
                   1690        1700        1710        1720
             *     *     *     *     *     *     *     *     *
    TTG ACA TGG ACC AAC CCA AGT ATT AAG AGT GTT ATA ATA CTA AAA TAT
    Leu Thr Trp Thr Asn Pro Ser Ile Lys Ser Val Ile Ile Leu Lys Tyr>
          1730        1740        1750        1760        1770
       *     *     *     *     *     *     *     *     *     *
    AAC ATT CAA TAT AGG ACC AAA GAT GCC TCA ACT TGG AGC CAG ATT CCT
    Asn Ile Gln Tyr Arg Thr Lys Asp Ala Ser Thr Trp Ser Gln Ile Pro>
```

Fig.24D.

```
        1780           1790           1800           1810           1820
         *     *     *     *     *     *     *     *     *     *
        CCT GAA GAC ACA GCA TCC ACC CGA TCT TCA TTC ACT GTC CAA GAC CTT
        Pro Glu Asp Thr Ala Ser Thr Arg Ser Ser Phe Thr Val Gln Asp Leu>

1830           1840           1850           1860           1870
         *     *     *     *     *     *     *     *     *     *
        AAA CCT TTT ACA GAA TAT GTG TTT AGG ATT CGC TGT ATG AAG GAA GAT
        Lys Pro Phe Thr Glu Tyr Val Phe Arg Ile Arg Cys Met Lys Glu Asp>

1880           1890           1900           1910           1920
         *     *     *     *     *     *     *     *     *     *
        GGT AAG GGA TAC TGG AGT GAC TGG AGT GAA GAA GCA AGT GGG ATC ACC
        Gly Lys Gly Tyr Trp Ser Asp Trp Ser Glu Glu Ala Ser Gly Ile Thr>

1930           1940           1950           1960
         *     *     *     *     *     *     *     *     *
        TAT GAA GAT AGA CCA TCT AAA GCA CCA AGT TTC TGG TAT AAA ATA GAT
        Tyr Glu Asp Arg Pro Ser Lys Ala Pro Ser Phe Trp Tyr Lys Ile Asp>

1970           1980           1990           2000           2010
   *     *     *     *     *     *     *     *     *     *
  CCA TCC CAT ACT CAA GGC TAC AGA ACT GTA CAA CTC GTG TGG AAG ACA
  Pro Ser His Thr Gln Gly Tyr Arg Thr Val Gln Leu Val Trp Lys Thr>

2020           2030           2040           2050           2060
         *     *     *     *     *     *     *     *     *     *
        TTG CCT CCT TTT GAA GCC AAT GGA AAA ATC TTG GAT TAT GAA GTG ACT
        Leu Pro Pro Phe Glu Ala Asn Gly Lys Ile Leu Asp Tyr Glu Val Thr>

2070           2080           2090           2100           2110
         *     *     *     *     *     *     *     *     *     *
        CTC ACA AGA TGG AAA TCA CAT TTA CAA AAT TAC ACA GTT AAT GCC ACA
        Leu Thr Arg Trp Lys Ser His Leu Gln Asn Tyr Thr Val Asn Ala Thr>

2120           2130           2140           2150           2160
         *     *     *     *     *     *     *     *     *     *
        AAA CTG ACA GTA AAT CTC ACA AAT GAT CGC TAT CTA GCA ACC CTA ACA
        Lys Leu Thr Val Asn Leu Thr Asn Asp Arg Tyr Leu Ala Thr Leu Thr>

2170           2180           2190           2200
         *     *     *     *     *     *     *     *     *
        GTA AGA AAT CTT GTT GGC AAA TCA GAT GCA GCT GTT TTA ACT ATC CCT
        Val Arg Asn Leu Val Gly Lys Ser Asp Ala Ala Val Leu Thr Ile Pro>

2210           2220           2230           2240           2250
   *     *     *     *     *     *     *     *     *     *
  GCC TGT GAC TTT CAA GCT ACT CAC CCT GTA ATG GAT CTT AAA GCA TTC
  Ala Cys Asp Phe Gln Ala Thr His Pro Val Met Asp Leu Lys Ala Phe>

2260           2270           2280           2290           2300
         *     *     *     *     *     *     *     *     *     *
        CCC AAA GAT AAC ATG CTT TGG GTG GAA TGG ACT ACT CCA AGG GAA TCT
        Pro Lys Asp Asn Met Leu Trp Val Glu Trp Thr Thr Pro Arg Glu Ser>

2310           2320           2330           2340           2350
         *     *     *     *     *     *     *     *     *     *
        GTA AAG AAA TAT ATA CTT GAG TGG TGT GTG TTA TCA GAT AAA GCA CCC
        Val Lys Lys Tyr Ile Leu Glu Trp Cys Val Leu Ser Asp Lys Ala Pro>

```
              *         *         *         *         *         *         *         *         *         *
         TGT ATC ACA GAC TGG CAA CAA GAA GAT GGT ACC GTG CAT CGC ACC TAT
         Cys Ile Thr Asp Trp Gln Gln Glu Asp Gly Thr Val His Arg Thr Tyr>

2410           2420          2430            2440
              *         *         *         *         *         *         *         *         *
         TTA AGA GGG AAC TTA GCA GAG AGC AAA TGC TAT TTG ATA ACA GTT ACT
         Leu Arg Gly Asn Leu Ala Glu Ser Lys Cys Tyr Leu Ile Thr Val Thr>

2450          2460           2470          2480           2490
         *         *         *         *         *         *         *         *         *         *
         CCA GTA TAT GCT GAT GGA CCA GGA AGC CCT GAA TCC ATA AAG GCA TAC
         Pro Val Tyr Ala Asp Gly Pro Gly Ser Pro Glu Ser Ile Lys Ala Tyr>

2500          2510           2520          2530           2540
              *         *         *         *         *         *         *         *         *
         CTT AAA CAA GCT CCA CCT TCC AAA GGA CCT ACT GTT CGG ACA AAA AAA
         Leu Lys Gln Ala Pro Pro Ser Lys Gly Pro Thr Val Arg Thr Lys Lys>

2550          2560           2570          2580           2590
         *         *         *         *         *         *         *         *         *         *
         GTA GGG AAA AAC GAA GCT GTC TTA GAG TGG GAC CAA CTT CCT GTT GAT
         Val Gly Lys Asn Glu Ala Val Leu Glu Trp Asp Gln Leu Pro Val Asp>

2600           2610          2620            2630          2640
              *         *         *         *         *         *         *         *         *
         GTT CAG AAT GGA TTT ATC AGA AAT TAT ACT ATA TTT TAT AGA ACC ATC
         Val Gln Asn Gly Phe Ile Arg Asn Tyr Thr Ile Phe Tyr Arg Thr Ile>

2650          2660           2670          2680
              *         *         *         *         *         *         *         *         *
         ATT GGA AAT GAA ACT GCT GTG AAT GTG GAT TCT TCC CAC ACA GAA TAT
         Ile Gly Asn Glu Thr Ala Val Asn Val Asp Ser Ser His Thr Glu Tyr>

2690          2700           2710          2720           2730
         *         *         *         *         *         *         *         *         *         *
         ACA TTG TCC TCT TTG ACT AGT GAC ACA TTG TAC ATG GTA CGA ATG GCA
         Thr Leu Ser Ser Leu Thr Ser Asp Thr Leu Tyr Met Val Arg Met Ala>

2740          2750           2760          2770           2780
              *         *         *         *         *         *         *         *         *
         GCA TAC ACA GAT GAA GGT GGG AAG GAT GGT CCA GAA TTC ACT TTT ACT
         Ala Tyr Thr Asp Glu Gly Gly Lys Asp Gly Pro Glu Phe Thr Phe Thr>

2790           2800          2810           2820          2830
         *         *         *         *         *         *         *         *         *         *
         ACC CCA AAG TTT GCT CAA GGA GAA ATT GAA TCC GGG GGC GAC AAA ACT
         Thr Pro Lys Phe Ala Gln Gly Glu Ile Glu Ser Gly Gly Asp Lys Thr>

2840          2850           2860          2870           2880
         *         *         *         *         *         *         *         *         *         *
         CAC ACA TGC CCA CCG TGC CCA GCA CCT GAA CTC CTG GGG GGA CCG TCA
         His Thr Cys Pro Pro Cys Pro Ala Pro Glu Leu Leu Gly Gly Pro Ser>

2890          2900           2910          2920
              *         *         *         *         *         *         *         *         *
         GTC TTC CTC TTC CCC CCA AAA CCC AAG GAC ACC CTC ATG ATC TCC CGG
         Val Phe Leu Phe Pro Pro Lys Pro Lys Asp Thr Leu Met Ile Ser Arg>

2930          2940           2950          2960           2970
         *         *         *         *         *         *         *         *         *         *
         ACC CCT GAG GTC ACA TGC GTG GTG GTG GAC GTG AGC CAC GAA GAC CCT
```

Fig.24F.

```
                Thr Pro Glu Val Thr Cys Val Val Val Asp Val Ser His Glu Asp Pro>
     2980          2990          3000          3010          3020
       *       *     *       *     *       *     *       *     *       *
     GAG GTC AAG TTC AAC TGG TAC GTG GAC GGC GTG GAG GTG CAT AAT GCC
     Glu Val Lys Phe Asn Trp Tyr Val Asp Gly Val Glu Val His Asn Ala>
           3030          3040          3050          3060          3070
             *       *     *       *     *       *     *       *     *
     AAG ACA AAG CCG CGG GAG GAG CAG TAC AAC AGC ACG TAC CGT GTG GTC
     Lys Thr Lys Pro Arg Glu Glu Gln Tyr Asn Ser Thr Tyr Arg Val Val>
           3080          3090          3100          3110          3120
             *       *     *       *     *       *     *       *     *
     AGC GTC CTC ACC GTC CTG CAC CAG GAC TGG CTG AAT GGC AAG GAG TAC
     Ser Val Leu Thr Val Leu His Gln Asp Trp Leu Asn Gly Lys Glu Tyr>
                 3130          3140          3150          3160
                   *       *     *       *     *       *     *       *     *
     AAG TGC AAG GTC TCC AAC AAA GCC CTC CCA GCC CCC ATC GAG AAA ACC
     Lys Cys Lys Val Ser Asn Lys Ala Leu Pro Ala Pro Ile Glu Lys Thr>
 3170          3180          3190          3200          3210
   *       *     *       *     *       *     *       *     *       *
 ATC TCC AAA GCC AAA GGG CAG CCC CGA GAA CCA CAG GTG TAC ACC CTG
 Ile Ser Lys Ala Lys Gly Gln Pro Arg Glu Pro Gln Val Tyr Thr Leu>
       3220          3230          3240          3250          3260
         *       *     *       *     *       *     *       *     *
     CCC CCA TCC CGG GAT GAG CTG ACC AAG AAC CAG GTC AGC CTG ACC TGC
     Pro Pro Ser Arg Asp Glu Leu Thr Lys Asn Gln Val Ser Leu Thr Cys>
           3270          3280          3290          3300          3310
             *       *     *       *     *       *     *       *     *
     CTG GTC AAA GGC TTC TAT CCC AGC GAC ATC GCC GTG GAG TGG GAG AGC
     Leu Val Lys Gly Phe Tyr Pro Ser Asp Ile Ala Val Glu Trp Glu Ser>
                 3320          3330          3340          3350          3360
                   *       *     *       *     *       *     *       *     *
     AAT GGG CAG CCG GAG AAC AAC TAC AAG ACC ACG CCT CCC GTG CTG GAC
     Asn Gly Gln Pro Glu Asn Asn Tyr Lys Thr Thr Pro Pro Val Leu Asp>
                 3370          3380          3390          3400
                   *       *     *       *     *       *     *       *     *
     TCC GAC GGC TCC TTC TTC CTC TAC AGC AAG CTC ACC GTG GAC AAG AGC
     Ser Asp Gly Ser Phe Phe Leu Tyr Ser Lys Leu Thr Val Asp Lys Ser>
 3410          3420          3430          3440          3450
   *       *     *       *     *       *     *       *     *       *
 AGG TGG CAG CAG GGG AAC GTC TTC TCA TGC TCC GTG ATG CAT GAG GCT
 Arg Trp Gln Gln Gly Asn Val Phe Ser Cys Ser Val Met His Glu Ala>
       3460          3470          3480          3490          3500
         *       *     *       *     *       *     *       *     *
     CTG CAC AAC CAC TAC ACG CAG AAG AGC CTC TCC CTG TCT CCG GGT AAA
     Leu His Asn His Tyr Thr Gln Lys Ser Leu Ser Leu Ser Pro Gly Lys>
 *
 TGA
 ***>
```

Fig.25A.

```
                10               20               30               40
         *       *       *       *       *       *       *       *       *
        ATG GTG GCC GTC GGC TGC GCG CTG CTG GCT GCC CTG CTG GCC GCG CCG
        Met Val Ala Val Gly Cys Ala Leu Leu Ala Ala Leu Leu Ala Ala Pro>

50              60               70              80               90
  *       *       *       *       *       *       *       *       *       *
 GGA GCG GCG CTG GCC CCA AGG CGC TGC CCT GCG CAG GAG GTG GCA AGA
 Gly Ala Ala Leu Ala Pro Arg Arg Cys Pro Ala Gln Glu Val Ala Arg>

100              110              120              130              140
         *       *       *       *       *       *       *       *       *
        GGC GTG CTG ACC AGT CTG CCA GGA GAC AGC GTG ACT CTG ACC TGC CCG
        Gly Val Leu Thr Ser Leu Pro Gly Asp Ser Val Thr Leu Thr Cys Pro>

150              160              170              180              190
         *       *       *       *       *       *       *       *       *
        GGG GTA GAG CCG GAA GAC AAT GCC ACT GTT CAC TGG GTG CTC AGG AAG
        Gly Val Glu Pro Glu Asp Asn Ala Thr Val His Trp Val Leu Arg Lys>

200              210              220              230              240
         *       *       *       *       *       *       *       *       *       *
        CCG GCT GCA GGC TCC CAC CCC AGC AGA TGG GCT GGC ATG GGA AGG AGG
        Pro Ala Ala Gly Ser His Pro Ser Arg Trp Ala Gly Met Gly Arg Arg>

250              260              270              280
         *       *       *       *       *       *       *       *       *
        CTG CTG CTG AGG TCG GTG CAG CTC CAC GAC TCT GGA AAC TAT TCA TGC
        Leu Leu Leu Arg Ser Val Gln Leu His Asp Ser Gly Asn Tyr Ser Cys>

290             300              310              320              330
  *       *       *       *       *       *       *       *       *       *
 TAC CGG GCC GGC CGC CCA GCT GGG ACT GTG CAC TTG CTG GTG GAT GTT
 Tyr Arg Ala Gly Arg Pro Ala Gly Thr Val His Leu Leu Val Asp Val>

340              350              360              370              380
         *       *       *       *       *       *       *       *       *
        CCC CCC GAG GAG CCC CAG CTC TCC TGC TTC CGG AAG AGC CCC CTC AGC
        Pro Pro Glu Glu Pro Gln Leu Ser Cys Phe Arg Lys Ser Pro Leu Ser>

390              400              410              420              430
         *       *       *       *       *       *       *       *       *       *
        AAT GTT GTT TGT GAG TGG GGT CCT CGG AGC ACC CCA TCC CTG ACG ACA
        Asn Val Val Cys Glu Trp Gly Pro Arg Ser Thr Pro Ser Leu Thr Thr>

440              450              460              470              480
         *       *       *       *       *       *       *       *       *       *
        AAG GCT GTG CTC TTG GTG AGG AAG TTT CAG AAC AGT CCG GCC GAA GAC
        Lys Ala Val Leu Leu Val Arg Lys Phe Gln Asn Ser Pro Ala Glu Asp>

490              500              510              520
         *       *       *       *       *       *       *       *       *
        TTC CAG GAG CCG TGC CAG TAT TCC CAG GAG TCC CAG AAG TTC TCC TGC
        Phe Gln Glu Pro Cys Gln Tyr Ser Gln Glu Ser Gln Lys Phe Ser Cys>

530             540              550              560              570
  *       *       *       *       *       *       *       *       *       *
 CAG TTA GCA GTC CCG GAG GGA GAC AGC TCT TTC TAC ATA GTG TCC ATG
 Gln Leu Ala Val Pro Glu Gly Asp Ser Ser Phe Tyr Ile Val Ser Met>
```

Fig. 25B.

```
      580              590              600              610              620
       *        *       *        *       *        *       *        *       *
TGC  GTC  GCC  AGT  AGT  GTC  GGG  AGC  AAG  TTC  AGC  AAA  ACT  CAA  ACC  TTT
Cys  Val  Ala  Ser  Ser  Val  Gly  Ser  Lys  Phe  Ser  Lys  Thr  Gln  Thr  Phe>

630              640              650              660              670
 *        *       *        *       *        *       *        *       *        *
CAG  GGT  TGT  GGA  ATC  TTG  CAG  CCT  GAT  CCG  CCT  GCC  AAC  ATC  ACA  GTC
Gln  Gly  Cys  Gly  Ile  Leu  Gln  Pro  Asp  Pro  Pro  Ala  Asn  Ile  Thr  Val>

680              690              700              710              720
      *        *       *        *       *        *       *        *       *        *
ACT  GCC  GTG  GCC  AGA  AAC  CCC  CGC  TGG  CTC  AGT  GTC  ACC  TGG  CAA  GAC
Thr  Ala  Val  Ala  Arg  Asn  Pro  Arg  Trp  Leu  Ser  Val  Thr  Trp  Gln  Asp>

730              740              750              760
      *        *       *        *       *        *       *        *       *
CCC  CAC  TCC  TGG  AAC  TCA  TCT  TTC  TAC  AGA  CTA  CGG  TTT  GAG  CTC  AGA
Pro  His  Ser  Trp  Asn  Ser  Ser  Phe  Tyr  Arg  Leu  Arg  Phe  Glu  Leu  Arg>

770              780              790              800              810
 *        *       *        *       *        *       *        *       *        *
TAT  CGG  GCT  GAA  CGG  TCA  AAG  ACA  TTC  ACA  ACA  TGG  ATG  GTC  AAG  GAC
Tyr  Arg  Ala  Glu  Arg  Ser  Lys  Thr  Phe  Thr  Thr  Trp  Met  Val  Lys  Asp>

820              830              840              850              860
 *        *       *        *       *        *       *        *       *        *
CTC  CAG  CAT  CAC  TGT  GTC  ATC  CAC  GAC  GCC  TGG  AGC  GGC  CTG  AGG  CAC
Leu  Gln  His  His  Cys  Val  Ile  His  Asp  Ala  Trp  Ser  Gly  Leu  Arg  His>

870              880              890              900              910
 *        *       *        *       *        *       *        *       *        *
GTG  GTG  CAG  CTT  CGT  GCC  CAG  GAG  GAG  TTC  GGG  CAA  GGC  GAG  TGG  AGC
Val  Val  Gln  Leu  Arg  Ala  Gln  Glu  Glu  Phe  Gly  Gln  Gly  Glu  Trp  Ser>

920              930              940              950              960
      *        *       *        *       *        *       *        *       *        *
GAG  TGG  AGC  CCG  GAG  GCC  ATG  GGC  ACG  CCT  TGG  ACA  GAA  TCG  CGA  TCG
Glu  Trp  Ser  Pro  Glu  Ala  Met  Gly  Thr  Pro  Trp  Thr  Glu  Ser  Arg  Ser>

970              980              990              1000
      *        *       *        *       *        *       *        *       *
CCT  CCA  GCT  GAG  AAC  GAG  GTG  TCC  ACC  CCC  ATG  GAA  CTT  CTA  GAC  CCA
Pro  Pro  Ala  Glu  Asn  Glu  Val  Ser  Thr  Pro  Met  Glu  Leu  Leu  Asp  Pro>

1010             1020             1030             1040             1050
 *        *       *        *       *        *       *        *       *        *
TGT  GGT  TAT  ATC  AGT  CCT  GAA  TCT  CCA  GTT  GTA  CAA  CTT  CAT  TCT  AAT
Cys  Gly  Tyr  Ile  Ser  Pro  Glu  Ser  Pro  Val  Val  Gln  Leu  His  Ser  Asn>

1060             1070             1080             1090             1100
 *        *       *        *       *        *       *        *       *        *
TTC  ACT  GCA  GTT  TGT  GTG  CTA  AAG  GAA  AAA  TGT  ATG  GAT  TAT  TTT  CAT
Phe  Thr  Ala  Val  Cys  Val  Leu  Lys  Glu  Lys  Cys  Met  Asp  Tyr  Phe  His>

1110             1120             1130             1140             1150
 *        *       *        *       *        *       *        *       *        *
GTA  AAT  GCT  AAT  TAC  ATT  GTC  TGG  AAA  ACA  AAC  CAT  TTT  ACT  ATT  CCT
Val  Asn  Ala  Asn  Tyr  Ile  Val  Trp  Lys  Thr  Asn  His  Phe  Thr  Ile  Pro>

```
AAG GAG CAA TAT ACT ATC ATA AAC AGA ACA GCA TCC AGT GTC ACC TTT
Lys Glu Gln Tyr Thr Ile Ile Asn Arg Thr Ala Ser Ser Val Thr Phe>
         1210        1220        1230        1240
          *           *           *           *           *
           *           *           *           *           *
ACA GAT ATA GCT TCA TTA AAT ATT CAG CTC ACT TGC AAC ATT CTT ACA
Thr Asp Ile Ala Ser Leu Asn Ile Gln Leu Thr Cys Asn Ile Leu Thr>
  1250        1260        1270        1280        1290
    *          *           *           *           *
     *          *           *           *           *
TTC GGA CAG CTT GAA CAG AAT GTT TAT GGA ATC ACA ATA ATT TCA GGC
Phe Gly Gln Leu Glu Gln Asn Val Tyr Gly Ile Thr Ile Ile Ser Gly>
      1300        1310        1320        1330        1340
        *           *           *           *           *
         *           *           *           *           *
TTG CCT CCA GAA AAA CCT AAA AAT TTG AGT TGC ATT GTG AAC GAG GGG
Leu Pro Pro Glu Lys Pro Lys Asn Leu Ser Cys Ile Val Asn Glu Gly>
        1350        1360        1370        1380        1390
          *           *           *           *           *
           *           *           *           *           *
AAG AAA ATG AGG TGT GAG TGG GAT GGT GGA AGG GAA ACA CAC TTG GAG
Lys Lys Met Arg Cys Glu Trp Asp Gly Gly Arg Glu Thr His Leu Glu>
         1400        1410        1420        1430        1440
           *          *           *           *           *
            *          *           *           *           *
ACA AAC TTC ACT TTA AAA TCT GAA TGG GCA ACA CAC AAG TTT GCT GAT
Thr Asn Phe Thr Leu Lys Ser Glu Trp Ala Thr His Lys Phe Ala Asp>
           1450        1460        1470        1480
             *           *           *           *
              *           *           *           *
TGC AAA GCA AAA CGT GAC ACC CCC ACC TCA TGC ACT GTT GAT TAT TCT
Cys Lys Ala Lys Arg Asp Thr Pro Thr Ser Cys Thr Val Asp Tyr Ser>
  1490        1500        1510        1520        1530
    *           *           *           *           *
     *           *           *           *           *
ACT GTG TAT TTT GTC AAC ATT GAA GTC TGG GTA GAA GCA GAG AAT GCC
Thr Val Tyr Phe Val Asn Ile Glu Val Trp Val Glu Ala Glu Asn Ala>
      1540        1550        1560        1570        1580
        *           *           *           *           *
         *           *           *           *           *
CTT GGG AAG GTT ACA TCA GAT CAT ATC AAT TTT GAT CCT GTA TAT AAA
Leu Gly Lys Val Thr Ser Asp His Ile Asn Phe Asp Pro Val Tyr Lys>
          1590        1600        1610        1620        1630
            *           *           *           *           *
             *           *           *           *           *
GTG AAG CCC AAT CCG CCA CAT AAT TTA TCA GTG ATC AAC TCA GAG GAA
Val Lys Pro Asn Pro Pro His Asn Leu Ser Val Ile Asn Ser Glu Glu>
             1640        1650        1660        1670        1680
               *           *           *           *           *
                *           *           *           *           *
CTG TCT AGT ATC TTA AAA TTG ACA TGG ACC AAC CCA AGT ATT AAG AGT
Leu Ser Ser Ile Leu Lys Leu Thr Trp Thr Asn Pro Ser Ile Lys Ser>
                 1690        1700        1710        1720
                   *           *           *           *
                    *           *           *           *
GTT ATA ATA CTA AAA TAT AAC ATT CAA TAT AGG ACC AAA GAT GCC TCA
Val Ile Ile Leu Lys Tyr Asn Ile Gln Tyr Arg Thr Lys Asp Ala Ser>
   1730        1740        1750        1760        1770
     *           *           *           *           *
      *           *           *           *           *
ACT TGG AGC CAG ATT CCT CCT GAA GAC ACA GCA TCC ACC CGA TCT TCA
Thr Trp Ser Gln Ile Pro Pro Glu Asp Thr Ala Ser Thr Arg Ser Ser>
```

Fig.25D.

```
      1780          1790          1800          1810          1820
        *             *             *             *             *
    *             *             *             *             *
TTC ACT GTC CAA GAC CTT AAA CCT TTT ACA GAA TAT GTG TTT AGG ATT
Phe Thr Val Gln Asp Leu Lys Pro Phe Thr Glu Tyr Val Phe Arg Ile>

1830          1840          1850          1860          1870
        *             *             *             *             *
    *             *             *             *             *
CGC TGT ATG AAG GAA GAT GGT AAG GGA TAC TGG AGT GAC TGG AGT GAA
Arg Cys Met Lys Glu Asp Gly Lys Gly Tyr Trp Ser Asp Trp Ser Glu>

1880          1890          1900          1910          1920
        *             *             *             *             *
    *             *             *             *             *
GAA GCA AGT GGG ATC ACC TAT GAA GAT AGA CCA TCT AAA GCA CCA AGT
Glu Ala Ser Gly Ile Thr Tyr Glu Asp Arg Pro Ser Lys Ala Pro Ser>

1930          1940          1950          1960
        *             *             *             *
    *             *             *             *
TTC TGG TAT AAA ATA GAT CCA TCC CAT ACT CAA GGC TAC AGA ACT GTA
Phe Trp Tyr Lys Ile Asp Pro Ser His Thr Gln Gly Tyr Arg Thr Val>

1970          1980          1990          2000          2010
  *             *             *             *             *
    *             *             *             *             *
CAA CTC GTG TGG AAG ACA TTG CCT CCT TTT GAA GCC AAT GGA AAA ATC
Gln Leu Val Trp Lys Thr Leu Pro Pro Phe Glu Ala Asn Gly Lys Ile>

2020          2030          2040          2050          2060
        *             *             *             *             *
    *             *             *             *             *
TTG GAT TAT GAA GTG ACT CTC ACA AGA TGG AAA TCA CAT TTA CAA AAT
Leu Asp Tyr Glu Val Thr Leu Thr Arg Trp Lys Ser His Leu Gln Asn>

2070          2080          2090          2100          2110
        *             *             *             *             *
    *             *             *             *             *
TAC ACA GTT AAT GCC ACA AAA CTG ACA GTA AAT CTC ACA AAT GAT CGC
Tyr Thr Val Asn Ala Thr Lys Leu Thr Val Asn Leu Thr Asn Asp Arg>

2120          2130          2140          2150          2160
        *             *             *             *             *
    *             *             *             *             *
TAT CTA GCA ACC CTA ACA GTA AGA AAT CTT GTT GGC AAA TCA GAT GCA
Tyr Leu Ala Thr Leu Thr Val Arg Asn Leu Val Gly Lys Ser Asp Ala>

2170          2180          2190          2200
        *             *             *             *
    *             *             *             *
GCT GTT TTA ACT ATC CCT GCC TGT GAC TTT CAA GCT ACT CAC CCT GTA
Ala Val Leu Thr Ile Pro Ala Cys Asp Phe Gln Ala Thr His Pro Val>

2210          2220          2230          2240          2250
  *             *             *             *             *
    *             *             *             *             *
ATG GAT CTT AAA GCA TTC CCC AAA GAT AAC ATG CTT TGG GTG GAA TGG
Met Asp Leu Lys Ala Phe Pro Lys Asp Asn Met Leu Trp Val Glu Trp>

2260          2270          2280          2290          2300
        *             *             *             *             *
    *             *             *             *             *
ACT ACT CCA AGG GAA TCT GTA AAG AAA TAT ATA CTT GAG TGG TGT GTG
Thr Thr Pro Arg Glu Ser Val Lys Lys Tyr Ile Leu Glu Trp Cys Val>

2310          2320          2330          2340          2350
        *             *             *             *             *
    *             *             *             *             *
TTA TCA GAT AAA GCA CCC TGT ATC ACA GAC TGG CAA CAA GAA GAT GGT
Leu Ser Asp Lys Ala Pro Cys Ile Thr Asp Trp Gln Gln Glu Asp Gly>

```
         *         *         *         *         *         *         *         *         *         *
        ACC GTG CAT CGC ACC TAT TTA AGA GGG AAC TTA GCA GAG AGC AAA TGC
        Thr Val His Arg Thr Tyr Leu Arg Gly Asn Leu Ala Glu Ser Lys Cys>

2410          2420          2430          2440
         *         *         *         *         *         *         *         *         *
        TAT TTG ATA ACA GTT ACT CCA GTA TAT GCT GAT GGA CCA GGA AGC CCT
        Tyr Leu Ile Thr Val Thr Pro Val Tyr Ala Asp Gly Pro Gly Ser Pro>

2450          2460          2470          2480          2490
   *         *         *         *         *         *         *         *         *         *
        GAA TCC ATA AAG GCA TAC CTT AAA CAA GCT CCA CCT TCC AAA GGA CCT
        Glu Ser Ile Lys Ala Tyr Leu Lys Gln Ala Pro Pro Ser Lys Gly Pro>

2500          2510          2520          2530          2540
         *         *         *         *         *         *         *         *         *         *
        ACT GTT CGG ACA AAA AAA GTA GGG AAA AAC GAA GCT GTC TTA GAG TGG
        Thr Val Arg Thr Lys Lys Val Gly Lys Asn Glu Ala Val Leu Glu Trp>

2550          2560          2570          2580          2590
         *         *         *         *         *         *         *         *         *         *
        GAC CAA CTT CCT GTT GAT GTT CAG AAT GGA TTT ATC AGA AAT TAT ACT
        Asp Gln Leu Pro Val Asp Val Gln Asn Gly Phe Ile Arg Asn Tyr Thr>

2600          2610          2620          2630          2640
         *         *         *         *         *         *         *         *         *         *
        ATA TTT TAT AGA ACC ATC ATT GGA AAT GAA ACT GCT GTG AAT GTG GAT
        Ile Phe Tyr Arg Thr Ile Ile Gly Asn Glu Thr Ala Val Asn Val Asp>

2650          2660          2670          2680
         *         *         *         *         *         *         *         *         *
        TCT TCC CAC ACA GAA TAT ACA TTG TCC TCT TTG ACT AGT GAC ACA TTG
        Ser Ser His Thr Glu Tyr Thr Leu Ser Ser Leu Thr Ser Asp Thr Leu>

2690          2700          2710          2720          2730
   *         *         *         *         *         *         *         *         *         *
        TAC ATG GTA CGA ATG GCA GCA TAC ACA GAT GAA GGT GGG AAG GAT GGT
        Tyr Met Val Arg Met Ala Ala Tyr Thr Asp Glu Gly Gly Lys Asp Gly>

2740          2750          2760          2770          2780
         *         *         *         *         *         *         *         *         *
        CCA GAA TTC ACT TTT ACT ACC CCA AAG TTT GCT CAA GGA GAA ATT GAA
        Pro Glu Phe Thr Phe Thr Thr Pro Lys Phe Ala Gln Gly Glu Ile Glu>

2790          2800          2810          2820          2830
         *         *         *         *         *         *         *         *         *         *
        TCC GGG GGC GAC AAA ACT CAC ACA TGC CCA CCG TGC CCA GCA CCT GAA
        Ser Gly Gly Asp Lys Thr His Thr Cys Pro Pro Cys Pro Ala Pro Glu>

2840          2850          2860          2870          2880
         *         *         *         *         *         *         *         *         *         *
        CTC CTG GGG GGA CCG TCA GTC TTC CTC TTC CCC CCA AAA CCC AAG GAC
        Leu Leu Gly Gly Pro Ser Val Phe Leu Phe Pro Pro Lys Pro Lys Asp>

2890          2900          2910          2920
         *         *         *         *         *         *         *         *         *
        ACC CTC ATG ATC TCC CGG ACC CCT GAG GTC ACA TGC GTG GTG GTG GAC
        Thr Leu Met Ile Ser Arg Thr Pro Glu Val Thr Cys Val Val Val Asp>

2930          2940          2950          2960          2970
   *         *         *         *         *         *         *         *         *         *
        GTG AGC CAC GAA GAC CCT GAG GTC AAG TTC AAC TGG TAC GTG GAC GGC
```

Fig.25F.

```
                  Val Ser His Glu Asp Pro Glu Val Lys Phe Asn Trp Tyr Val Asp Gly>
       2980          2990          3000          3010          3020
         *      *      *      *      *      *      *      *      *      *
       GTG GAG GTG CAT AAT GCC AAG ACA AAG CCG CGG GAG GAG CAG TAC AAC
       Val Glu Val His Asn Ala Lys Thr Lys Pro Arg Glu Glu Gln Tyr Asn>

3030          3040          3050          3060          3070
         *      *      *      *      *      *      *      *      *      *
       AGC ACG TAC CGT GTG GTC AGC GTC CTC ACC GTC CTG CAC CAG GAC TGG
       Ser Thr Tyr Arg Val Val Ser Val Leu Thr Val Leu His Gln Asp Trp>

3080          3090          3100          3110          3120
         *      *      *      *      *      *      *      *      *      *
       CTG AAT GGC AAG GAG TAC AAG TGC AAG GTC TCC AAC AAA GCC CTC CCA
       Leu Asn Gly Lys Glu Tyr Lys Cys Lys Val Ser Asn Lys Ala Leu Pro>

3130          3140          3150          3160
            *      *      *      *      *      *      *      *      *
          GCC CCC ATC GAG AAA ACC ATC TCC AAA GCC AAA GGG CAG CCC CGA GAA
          Ala Pro Ile Glu Lys Thr Ile Ser Lys Ala Lys Gly Gln Pro Arg Glu>

3170          3180          3190          3200          3210
  *      *      *      *      *      *      *      *      *      *
CCA CAG GTG TAC ACC CTG CCC CCA TCC CGG GAT GAG CTG ACC AAG AAC
Pro Gln Val Tyr Thr Leu Pro Pro Ser Arg Asp Glu Leu Thr Lys Asn>

3220          3230          3240          3250          3260
         *      *      *      *      *      *      *      *      *      *
       CAG GTC AGC CTG ACC TGC CTG GTC AAA GGC TTC TAT CCC AGC GAC ATC
       Gln Val Ser Leu Thr Cys Leu Val Lys Gly Phe Tyr Pro Ser Asp Ile>

3270          3280          3290          3300          3310
         *      *      *      *      *      *      *      *      *      *
       GCC GTG GAG TGG GAG AGC AAT GGG CAG CCG GAG AAC AAC TAC AAG ACC
       Ala Val Glu Trp Glu Ser Asn Gly Gln Pro Glu Asn Asn Tyr Lys Thr>

3320          3330          3340          3350          3360
           *      *      *      *      *      *      *      *      *      *
          ACG CCT CCC GTG CTG GAC TCC GAC GGC TCC TTC TTC CTC TAC AGC AAG
          Thr Pro Pro Val Leu Asp Ser Asp Gly Ser Phe Phe Leu Tyr Ser Lys>

3370          3380          3390          3400
              *      *      *      *      *      *      *      *      *
             CTC ACC GTG GAC AAG AGC AGG TGG CAG CAG GGG AAC GTC TTC TCA TGC
             Leu Thr Val Asp Lys Ser Arg Trp Gln Gln Gly Asn Val Phe Ser Cys>

3410          3420          3430          3440          3450
  *      *      *      *      *      *      *      *      *      *
TCC GTG ATG CAT GAG GCT CTG CAC AAC CAC TAC ACG CAG AAG AGC CTC
Ser Val Met His Glu Ala Leu His Asn His Tyr Thr Gln Lys Ser Leu>

3460          3470
         *      *      *      *
       TCC CTG TCT CCG GGT AAA TGA
       Ser Leu Ser Pro Gly Lys ***>
```

Fig.26A.

```
         10              20              30              40
          *               *               *               *
ATG GTG CTT CTG TGG TGT GTA GTG AGT CTC TAC TTT TAT GGA ATC CTG
Met Val Leu Leu Trp Cys Val Val Ser Leu Tyr Phe Tyr Gly Ile Leu>

50              60              70              80              90
  *               *               *               *               *
CAA AGT GAT GCC TCA GAA CGC TGC GAT GAC TGG GGA CTA GAC ACC ATG
Gln Ser Asp Ala Ser Glu Arg Cys Asp Asp Trp Gly Leu Asp Thr Met>

100             110             120             130             140
         *               *               *               *               *
AGG CAA ATC CAA GTG TTT GAA GAT GAG CCA GCT CGC ATC AAG TGC CCA
Arg Gln Ile Gln Val Phe Glu Asp Glu Pro Ala Arg Ile Lys Cys Pro>

150             160             170             180             190
  *      *       *       *       *       *       *       *       *       *
CTC TTT GAA CAC TTC TTG AAA TTC AAC TAC AGC ACA GCC CAT TCA GCT
Leu Phe Glu His Phe Leu Lys Phe Asn Tyr Ser Thr Ala His Ser Ala>

200             210             220             230             240
  *      *       *       *       *       *       *       *       *       *
GGC CTT ACT CTG ATC TGG TAT TGG ACT AGG CAG GAC CGG GAC CTT GAG
Gly Leu Thr Leu Ile Trp Tyr Trp Thr Arg Gln Asp Arg Asp Leu Glu>

250             260             270             280
  *      *       *       *       *       *       *       *       *
GAG CCA ATT AAC TTC CGC CTC CCC GAG AAC CGC ATT AGT AAG GAG AAA
Glu Pro Ile Asn Phe Arg Leu Pro Glu Asn Arg Ile Ser Lys Glu Lys>

290             300             310             320             330
 *       *       *       *       *       *       *       *       *       *
GAT GTG CTG TGG TTC CGG CCC ACT CTC CTC AAT GAC ACT GGC AAC TAT
Asp Val Leu Trp Phe Arg Pro Thr Leu Leu Asn Asp Thr Gly Asn Tyr>

340             350             360             370             380
  *      *       *       *       *       *       *       *       *
ACC TGC ATG TTA AGG AAC ACT ACA TAT TGC AGC AAA GTT GCA TTT CCC
Thr Cys Met Leu Arg Asn Thr Thr Tyr Cys Ser Lys Val Ala Phe Pro>

390             400             410             420             430
  *      *       *       *       *       *       *       *       *       *
TTG GAA GTT GTT CAA AAA GAC AGC TGT TTC AAT TCC CCC ATG AAA CTC
Leu Glu Val Val Gln Lys Asp Ser Cys Phe Asn Ser Pro Met Lys Leu>

440             450             460             470             480
  *      *       *       *       *       *       *       *       *       *
CCA GTG CAT AAA CTG TAT ATA GAA TAT GGC ATT CAG AGG ATC ACT TGT
Pro Val His Lys Leu Tyr Ile Glu Tyr Gly Ile Gln Arg Ile Thr Cys>

490             500             510             520
  *      *       *       *       *       *       *       *       *
CCA AAT GTA GAT GGA TAT TTT CCT TCC AGT GTC AAA CCG ACT ATC ACT
Pro Asn Val Asp Gly Tyr Phe Pro Ser Ser Val Lys Pro Thr Ile Thr>

530             540             550             560             570
 *       *       *       *       *       *       *       *       *       *
TGG TAT ATG GGC TGT TAT AAA ATA CAG AAT TTT AAT AAT GTA ATA CCC
Trp Tyr Met Gly Cys Tyr Lys Ile Gln Asn Phe Asn Asn Val Ile Pro>
```

Fig.26B.

```
       580           590           600           610           620
         *      *      *      *      *      *      *      *      *      *
       GAA   GGT   ATG   AAC   TTG   AGT   TTC   CTC   ATT   GCC   TTA   ATT   TCA   AAT   AAT   GGA
       Glu   Gly   Met   Asn   Leu   Ser   Phe   Leu   Ile   Ala   Leu   Ile   Ser   Asn   Asn   Gly>

630           640           650           660           670
         *      *      *      *      *      *      *      *      *      *
       AAT   TAC   ACA   TGT   GTT   GTT   ACA   TAT   CCA   GAA   AAT   GGA   CGT   ACG   TTT   CAT
       Asn   Tyr   Thr   Cys   Val   Val   Thr   Tyr   Pro   Glu   Asn   Gly   Arg   Thr   Phe   His>

680           690           700           710           720
         *      *      *      *      *      *      *      *      *      *
       CTC   ACC   AGG   ACT   CTG   ACT   GTA   AAG   GTA   GTA   GGC   TCT   CCA   AAA   AAT   GCA
       Leu   Thr   Arg   Thr   Leu   Thr   Val   Lys   Val   Val   Gly   Ser   Pro   Lys   Asn   Ala>

730           740           750           760
         *      *      *      *      *      *      *      *      *
       GTG   CCC   CCT   GTG   ATC   CAT   TCA   CCT   AAT   GAT   CAT   GTG   GTC   TAT   GAG   AAA
       Val   Pro   Pro   Val   Ile   His   Ser   Pro   Asn   Asp   His   Val   Val   Tyr   Glu   Lys>

770           780           790           800           810
         *      *      *      *      *      *      *      *      *      *
       GAA   CCA   GGA   GAG   GAG   CTA   CTC   ATT   CCC   TGT   ACG   GTC   TAT   TTT   AGT   TTT
       Glu   Pro   Gly   Glu   Glu   Leu   Leu   Ile   Pro   Cys   Thr   Val   Tyr   Phe   Ser   Phe>

820           830           840           850           860
         *      *      *      *      *      *      *      *      *
       CTG   ATG   GAT   TCT   CGC   AAT   GAG   GTT   TGG   TGG   ACC   ATT   GAT   GGA   AAA   AAA
       Leu   Met   Asp   Ser   Arg   Asn   Glu   Val   Trp   Trp   Thr   Ile   Asp   Gly   Lys   Lys>

870           880           890           900           910
         *      *      *      *      *      *      *      *      *      *
       CCT   GAT   GAC   ATC   ACT   ATT   GAT   GTC   ACC   ATT   AAC   GAA   AGT   ATA   AGT   CAT
       Pro   Asp   Asp   Ile   Thr   Ile   Asp   Val   Thr   Ile   Asn   Glu   Ser   Ile   Ser   His>

920           930           940           950           960
         *      *      *      *      *      *      *      *      *      *
       AGT   AGA   ACA   GAA   GAT   GAA   ACA   AGA   ACT   CAG   ATT   TTG   AGC   ATC   AAG   AAA
       Ser   Arg   Thr   Glu   Asp   Glu   Thr   Arg   Thr   Gln   Ile   Leu   Ser   Ile   Lys   Lys>

970           980           990           1000
         *      *      *      *      *      *      *      *      *
       GTT   ACC   TCT   GAG   GAT   CTC   AAG   CGC   AGC   TAT   GTC   TGT   CAT   GCT   AGA   AGT
       Val   Thr   Ser   Glu   Asp   Leu   Lys   Arg   Ser   Tyr   Val   Cys   His   Ala   Arg   Ser>

1010          1020          1030          1040          1050
         *      *      *      *      *      *      *      *      *      *
       GCC   AAA   GGC   GAA   GTT   GCC   AAA   GCA   GCC   AAG   GTG   AAG   CAG   AAA   GTG   CCA
       Ala   Lys   Gly   Glu   Val   Ala   Lys   Ala   Ala   Lys   Val   Lys   Gln   Lys   Val   Pro>

1060          1070          1080          1090          1100
         *      *      *      *      *      *      *      *      *
       GCT   CCA   AGA   TAC   ACA   GTG   TCC   GGT   GGC   GCG   CCT   ATG   CTG   AGC   GAG   GCT
       Ala   Pro   Arg   Tyr   Thr   Val   Ser   Gly   Gly   Ala   Pro   Met   Leu   Ser   Glu   Ala>

1110          1120          1130          1140          1150
         *      *      *      *      *      *      *      *      *      *
       GAT   AAA   TGC   AAG   GAA   CGT   GAA   GAA   AAA   ATA   ATT   TTA   GTG   TCA   TCT   GCA
       Asp   Lys   Cys   Lys   Glu   Arg   Glu   Glu   Lys   Ile   Ile   Leu   Val   Ser   Ser   Ala>

```
                    AAT GAA ATT GAT GTT CGT CCC TGT CCT CTT AAC CCA AAT GAA CAC AAA
                    Asn Glu Ile Asp Val Arg Pro Cys Pro Leu Asn Pro Asn Glu His Lys>
           1210          1220          1230          1240
             *     *      *     *      *     *      *     *      *
           GGC ACT ATA ACT TGG TAT AAG GAT GAC AGC AAG ACA CCT GTA TCT ACA
           Gly Thr Ile Thr Trp Tyr Lys Asp Asp Ser Lys Thr Pro Val Ser Thr>
  1250          1260          1270          1280          1290
    *     *      *     *      *     *      *     *      *     *
    GAA CAA GCC TCC AGG ATT CAT CAA CAC AAA GAG AAA CTT TGG TTT GTT
    Glu Gln Ala Ser Arg Ile His Gln His Lys Glu Lys Leu Trp Phe Val>
           1300          1310          1320          1330          1340
             *     *      *     *      *     *      *     *      *
           CCT GCT AAG GTG GAG GAT TCA GGA CAT TAC TAT TGC GTG GTA AGA AAT
           Pro Ala Lys Val Glu Asp Ser Gly His Tyr Tyr Cys Val Val Arg Asn>
                    1350          1360          1370          1380          1390
                      *     *      *     *      *     *      *     *      *     *
                    TCA TCT TAC TGC CTC AGA ATT AAA ATA AGT GCA AAA TTT GTG GAG AAT
                    Ser Ser Tyr Cys Leu Arg Ile Lys Ile Ser Ala Lys Phe Val Glu Asn>
                             1400          1410          1420          1430          1440
                               *     *      *     *      *     *      *     *      *
                             GAG CCT AAC TTA TGT TAT AAT GCA CAA GCC ATA TTT AAG CAG AAA CTA
                             Glu Pro Asn Leu Cys Tyr Asn Ala Gln Ala Ile Phe Lys Gln Lys Leu>
                                      1450          1460          1470          1480
                                        *     *      *     *      *     *      *     *      *
                                      CCC GTT GCA GGA GAC GGA GGA CTT GTG TGC CCT TAT ATG GAG TTT TTT
                                      Pro Val Ala Gly Asp Gly Gly Leu Val Cys Pro Tyr Met Glu Phe Phe>
  1490          1500          1510          1520          1530
    *     *      *     *      *     *      *     *      *     *
    AAA AAT GAA AAT AAT GAG TTA CCT AAA TTA CAG TGG TAT AAG GAT TGC
    Lys Asn Glu Asn Asn Glu Leu Pro Lys Leu Gln Trp Tyr Lys Asp Cys>
           1540          1550          1560          1570          1580
             *     *      *     *      *     *      *     *      *
           AAA CCT CTA CTT CTT GAC AAT ATA CAC TTT AGT GGA GTC AAA GAT AGG
           Lys Pro Leu Leu Leu Asp Asn Ile His Phe Ser Gly Val Lys Asp Arg>
                    1590          1600          1610          1620          1630
                      *     *      *     *      *     *      *     *      *     *
                    CTC ATC GTG ATG AAT GTG GCT GAA AAG CAT AGA GGG AAC TAT ACT TGT
                    Leu Ile Val Met Asn Val Ala Glu Lys His Arg Gly Asn Tyr Thr Cys>
                             1640          1650          1660          1670          1680
                               *     *      *     *      *     *      *     *      *
                             CAT GCA TCC TAC ACA TAC TTG GGC AAG CAA TAT CCT ATT ACC CGG GTA
                             His Ala Ser Tyr Thr Tyr Leu Gly Lys Gln Tyr Pro Ile Thr Arg Val>
                                      1690          1700          1710          1720
                                        *     *      *     *      *     *      *     *
                                      ATA GAA TTT ATT ACT CTA GAG GAA AAC AAA CCC ACA AGG CCT GTG ATT
                                      Ile Glu Phe Ile Thr Leu Glu Glu Asn Lys Pro Thr Arg Pro Val Ile>
  1730          1740          1750          1760          1770
    *     *      *     *      *     *      *     *      *     *
    GTG AGC CCA GCT AAT GAG ACA ATG GAA GTA GAC TTG GGA TCC CAG ATA
    Val Ser Pro Ala Asn Glu Thr Met Glu Val Asp Leu Gly Ser Gln Ile>
```

Fig.26D.

```
     1780           1790           1800           1810           1820
       *     *       *     *        *     *       *     *        *     *
CAA TTG ATC TGT AAT GTC ACC GGC CAG TTG AGT GAC ATT GCT TAC TGG
Gln Leu Ile Cys Asn Val Thr Gly Gln Leu Ser Asp Ile Ala Tyr Trp>

1830           1840           1850           1860           1870
       *     *       *     *        *     *       *     *        *     *
AAG TGG AAT GGG TCA GTA ATT GAT GAA GAT GAC CCA GTG CTA GGG GAA
Lys Trp Asn Gly Ser Val Ile Asp Glu Asp Asp Pro Val Leu Gly Glu>

1880           1890           1900           1910           1920
       *     *       *     *        *     *       *     *        *     *
GAC TAT TAC AGT GTG GAA AAT CCT GCA AAC AAA AGA AGG AGT ACC CTC
Asp Tyr Tyr Ser Val Glu Asn Pro Ala Asn Lys Arg Arg Ser Thr Leu>

1930           1940           1950           1960
       *     *       *     *        *     *       *     *
ATC ACA GTG CTT AAT ATA TCG GAA ATT GAG AGT AGA TTT TAT AAA CAT
Ile Thr Val Leu Asn Ile Ser Glu Ile Glu Ser Arg Phe Tyr Lys His>

1970           1980           1990           2000           2010
   *     *       *     *        *     *       *     *        *     *
CCA TTT ACC TGT TTT GCC AAG AAT ACA CAT GGT ATA GAT GCA GCA TAT
Pro Phe Thr Cys Phe Ala Lys Asn Thr His Gly Ile Asp Ala Ala Tyr>

2020           2030           2040           2050           2060
       *     *       *     *        *     *       *     *        *     *
ATC CAG TTA ATA TAT CCA GTC ACT AAT TCC GGA GAC AAA ACT CAC ACA
Ile Gln Leu Ile Tyr Pro Val Thr Asn Ser Gly Asp Lys Thr His Thr>

2070           2080           2090           2100           2110
       *     *       *     *        *     *       *     *        *     *
TGC CCA CCG TGC CCA GCA CCT GAA CTC CTG GGG GGA CCG TCA GTC TTC
Cys Pro Pro Cys Pro Ala Pro Glu Leu Leu Gly Gly Pro Ser Val Phe>

2120           2130           2140           2150           2160
       *     *       *     *        *     *       *     *        *     *
CTC TTC CCC CCA AAA CCC AAG GAC ACC CTC ATG ATC TCC CGG ACC CCT
Leu Phe Pro Pro Lys Pro Lys Asp Thr Leu Met Ile Ser Arg Thr Pro>

2170           2180           2190           2200
       *     *       *     *        *     *       *     *
GAG GTC ACA TGC GTG GTG GTG GAC GTG AGC CAC GAA GAC CCT GAG GTC
Glu Val Thr Cys Val Val Val Asp Val Ser His Glu Asp Pro Glu Val>

2210           2220           2230           2240           2250
   *     *       *     *        *     *       *     *        *     *
AAG TTC AAC TGG TAC GTG GAC GGC GTG GAG GTG CAT AAT GCC AAG ACA
Lys Phe Asn Trp Tyr Val Asp Gly Val Glu Val His Asn Ala Lys Thr>

2260           2270           2280           2290           2300
       *     *       *     *        *     *       *     *        *     *
AAG CCG CGG GAG GAG CAG TAC AAC AGC ACG TAC CGT GTG GTC AGC GTC
Lys Pro Arg Glu Glu Gln Tyr Asn Ser Thr Tyr Arg Val Val Ser Val>

2310           2320           2330           2340           2350
       *     *       *     *        *     *       *     *        *     *
CTC ACC GTC CTG CAC CAG GAC TGG CTG AAT GGC AAG GAG TAC AAG TGC
Leu Thr Val Leu His Gln Asp Trp Leu Asn Gly Lys Glu Tyr Lys Cys>

```
         *         *         *         *         *         *         *         *         *         *
        AAG GTC TCC AAC AAA GCC CTC CCA GCC CCC ATC GAG AAA ACC ATC TCC
        Lys Val Ser Asn Lys Ala Leu Pro Ala Pro Ile Glu Lys Thr Ile Ser>

2410          2420          2430          2440
         *         *         *         *         *         *         *         *         *
        AAA GCC AAA GGG CAG CCC CGA GAA CCA CAG GTG TAC ACC CTG CCC CCA
        Lys Ala Lys Gly Gln Pro Arg Glu Pro Gln Val Tyr Thr Leu Pro Pro>

2450          2460          2470          2480          2490
   *     *     *     *     *     *     *     *     *     *
  TCC CGG GAG GAG ATG ACC AAG AAC CAG GTC AGC CTG ACC TGC CTG GTC
  Ser Arg Glu Glu Met Thr Lys Asn Gln Val Ser Leu Thr Cys Leu Val>

2500          2510          2520          2530          2540
     *     *     *     *     *     *     *     *     *
    AAA GGC TTC TAT CCC AGC GAC ATC GCC GTG GAG TGG GAG AGC AAT GGG
    Lys Gly Phe Tyr Pro Ser Asp Ile Ala Val Glu Trp Glu Ser Asn Gly>

2550          2560          2570          2580          2590
      *     *     *     *     *     *     *     *     *     *
     CAG CCG GAG AAC AAC TAC AAG ACC ACG CCT CCC GTG CTG GAC TCC GAC
     Gln Pro Glu Asn Asn Tyr Lys Thr Thr Pro Pro Val Leu Asp Ser Asp>

2600          2610          2620          2630          2640
        *     *     *     *     *     *     *     *     *     *
       GGC TCC TTC TTC CTC TAT AGC AAG CTC ACC GTG GAC AAG AGC AGG TGG
       Gly Ser Phe Phe Leu Tyr Ser Lys Leu Thr Val Asp Lys Ser Arg Trp>

2650          2660          2670          2680
           *     *     *     *     *     *     *     *     *
          CAG CAG GGG AAC GTC TTC TCA TGC TCC GTG ATG CAT GAG GCT CTG CAC
          Gln Gln Gly Asn Val Phe Ser Cys Ser Val Met His Glu Ala Leu His>

2690          2700          2710          2720          2730
   *     *     *     *     *     *     *     *     *
  AAC CAC TAC ACG CAG AAG AGC CTC TCC CTG TCT CCG GGT AAA TGA
  Asn His Tyr Thr Gln Lys Ser Leu Ser Leu Ser Pro Gly Lys ***>
```

XG1 Bioassay (10nM IL6 Trap)

MRC5 Bioassay (10nM IL1 Trap)
IL1 Trap 1SC569 vs IL1 Trap IL1RI.Fc

Fig.31A.

```
         10          20          30          40
    *      *    *      *    *      *    *      *    *
ATG GTG TGG CTT TGC TCT GGG CTC CTG TTC CCT GTG AGC TGC CTG GTC
TAC CAC ACC GAA ACG AGA CCC GAG GAC AAG GGA CAC TCG ACG GAC CAG
Met Val Trp Leu Cys Ser Gly Leu Leu Phe Pro Val Ser Cys Leu Val>

50          60          70          80          90
  *      *    *      *    *      *    *      *    *      *
CTG CTG CAG GTG GCA AGC TCT GGG AAC ATG AAG GTC TTG CAG GAG CCC
GAC GAC GTC CAC CGT TCG AGA CCC TTG TAC TTC CAG AAC GTC CTC GGG
Leu Leu Gln Val Ala Ser Ser Gly Asn Met Lys Val Leu Gln Glu Pro>

100         110         120         130         140
    *      *    *      *    *      *    *      *    *
ACC TGC GTC TCC GAC TAC ATG AGC ATC TCT ACT TGC GAG TGG AAG ATG
TGG ACG CAG AGG CTG ATG TAC TCG TAG AGA TGA ACG CTC ACC TTC TAC
Thr Cys Val Ser Asp Tyr Met Ser Ile Ser Thr Cys Glu Trp Lys Met>

150         160         170         180         190
  *      *    *      *    *      *    *      *    *      *
AAT GGT CCC ACC AAT TGC AGC ACC GAG CTC CGC CTG TTG TAC CAG CTG
TTA CCA GGG TGG TTA ACG TCG TGG CTC GAG GCG GAC AAC ATG GTC GAC
Asn Gly Pro Thr Asn Cys Ser Thr Glu Leu Arg Leu Leu Tyr Gln Leu>

200         210         220         230         240
    *      *    *      *    *      *    *      *    *      *
GTT TTT CTG CTC TCC GAA GCC CAC ACG TGT ATC CCT GAG AAC AAC GGA
CAA AAA GAC GAG AGG CTT CGG GTG TGC ACA TAG GGA CTC TTG TTG CCT
Val Phe Leu Leu Ser Glu Ala His Thr Cys Ile Pro Glu Asn Asn Gly>

250         260         270         280
  *      *    *      *    *      *    *      *    *
GGC GCG GGG TGC GTG TGC CAC CTG CTC ATG GAT GAC GTG GTC AGT GCG
CCG CGC CCC ACG CAC ACG GTG GAC GAG TAC CTA CTG CAC CAG TCA CGC
Gly Ala Gly Cys Val Cys His Leu Leu Met Asp Asp Val Val Ser Ala>

290         300         310         320         330
  *      *    *      *    *      *    *      *    *      *
GAT AAC TAT ACA CTG GAC CTG TGG GCT GGG CAG CAG CTG CTG TGG AAG
CTA TTG ATA TGT GAC CTG GAC ACC CGA CCC GTC GTC GAC GAC ACC TTC
Asp Asn Tyr Thr Leu Asp Leu Trp Ala Gly Gln Gln Leu Leu Trp Lys>

340         350         360         370         380
  *      *    *      *    *      *    *      *    *      *
GGC TCC TTC AAG CCC AGC GAG CAT GTG AAA CCC AGG GCC CCA GGA AAC
CCG AGG AAG TTC GGG TCG CTC GTA CAC TTT GGG TCC CGG GGT CCT TTG
Gly Ser Phe Lys Pro Ser Glu His Val Lys Pro Arg Ala Pro Gly Asn>
```

Fig.31B.

```
      390         400         410         420         430
       *     *     *     *     *     *     *     *     *     *
CTG ACA GTT CAC ACC AAT GTC TCC GAC ACT CTG CTG CTG ACC TGG AGC
GAC TGT CAA GTG TGG TTA CAG AGG CTG TGA GAC GAC GAC TGG ACC TCG
Leu Thr Val His Thr Asn Val Ser Asp Thr Leu Leu Leu Thr Trp Ser>

440         450         460         470         480
       *     *     *     *     *     *     *     *     *     *
AAC CCG TAT CCC CCT GAC AAT TAC CTG TAT AAT CAT CTC ACC TAT GCA
TTG GGC ATA GGG GGA CTG TTA ATG GAC ATA TTA GTA GAG TGG ATA CGT
Asn Pro Tyr Pro Pro Asp Asn Tyr Leu Tyr Asn His Leu Thr Tyr Ala>

490         500         510         520
       *     *     *     *     *     *     *     *     *
GTC AAC ATT TGG AGT GAA AAC GAC CCG GCA GAT TTC AGA ATC TAT AAC
CAG TTG TAA ACC TCA CTT TTG CTG GGC CGT CTA AAG TCT TAG ATA TTG
Val Asn Ile Trp Ser Glu Asn Asp Pro Ala Asp Phe Arg Ile Tyr Asn>

530         540         550         560         570
  *     *     *     *     *     *     *     *     *     *
GTG ACC TAC CTA GAA CCC TCC CTC CGC ATC GCA GCC AGC ACC CTG AAG
CAC TGG ATG GAT CTT GGG AGG GAG GCG TAG CGT CGG TCG TGG GAC TTC
Val Thr Tyr Leu Glu Pro Ser Leu Arg Ile Ala Ala Ser Thr Leu Lys>

580         590         600         610         620
       *     *     *     *     *     *     *     *     *
TCT GGG ATT TCC TAC AGG GCA CGG GTG AGG GCC TGG GCT CAG AGC TAT
AGA CCC TAA AGG ATG TCC CGT GCC CAC TCC CGG ACC CGA GTC TCG ATA
Ser Gly Ile Ser Tyr Arg Ala Arg Val Arg Ala Trp Ala Gln Ser Tyr>

630         640         650         660         670
       *     *     *     *     *     *     *     *     *     *
AAC ACC ACC TGG AGT GAG TGG AGC CCC AGC ACC AAG TGG CAC AAC TCC
TTG TGG TGG ACC TCA CTC ACC TCG GGG TCG TGG TTC ACC GTG TTG AGG
Asn Thr Thr Trp Ser Glu Trp Ser Pro Ser Thr Lys Trp His Asn Ser>

680         690         700         710         720
       *     *     *     *     *     *     *     *     *     *
TAC AGG GAG CCC TTC GAG CAG TCC GGT GGG GGC GGG GGC GCC GCG CCT
ATG TCC CTC GGG AAG CTC GTC AGG CCA CCC CCG CCC CCG CGG CGC GGA
Tyr Arg Glu Pro Phe Glu Gln Ser Gly Gly Gly Gly Gly Ala Ala Pro>

730         740         750         760
       *     *     *     *     *     *     *     *     *
ACG GAA ACT CAG CCA CCT GTG ACA AAT TTG AGT GTC TCT GTT GAA AAC
TGC CTT TGA GTC GGT GGA CAC TGT TTA AAC TCA CAG AGA CAA CTT TTG
Thr Glu Thr Gln Pro Pro Val Thr Asn Leu Ser Val Ser Val Glu Asn>
```

Fig.31C.

```
        770             780             790             800             810
         *       *       *       *       *       *       *       *       *       *
        CTC TGC ACA GTA ATA TGG ACA TGG AAT CCA CCC GAG GGA GCC AGC TCA
        GAG ACG TGT CAT TAT ACC TGT ACC TTA GGT GGG CTC CCT CGG TCG AGT
        Leu Cys Thr Val Ile Trp Thr Trp Asn Pro Pro Glu Gly Ala Ser Ser>

820             830             840             850             860
         *       *       *       *       *       *       *       *       *       *
        AAT TGT AGT CTA TGG TAT TTT AGT CAT TTT GGC GAC AAA CAA GAT AAG
        TTA ACA TCA GAT ACC ATA AAA TCA GTA AAA CCG CTG TTT GTT CTA TTC
        Asn Cys Ser Leu Trp Tyr Phe Ser His Phe Gly Asp Lys Gln Asp Lys>

870             880             890             900             910
         *       *       *       *       *       *       *       *       *       *
        AAA ATA GCT CCG GAA ACT CGT CGT TCA ATA GAA GTA CCC CTG AAT GAG
        TTT TAT CGA GGC CTT TGA GCA GCA AGT TAT CTT CAT GGG GAC TTA CTC
        Lys Ile Ala Pro Glu Thr Arg Arg Ser Ile Glu Val Pro Leu Asn Glu>

920             930             940             950             960
         *       *       *       *       *       *       *       *       *       *
        AGG ATT TGT CTG CAA GTG GGG TCC CAG TGT AGC ACC AAT GAG AGT GAG
        TCC TAA ACA GAC GTT CAC CCC AGG GTC ACA TCG TGG TTA CTC TCA CTC
        Arg Ile Cys Leu Gln Val Gly Ser Gln Cys Ser Thr Asn Glu Ser Glu>

970             980             990             1000
         *       *       *       *       *       *       *       *       *
        AAG CCT AGC ATT TTG GTT GAA AAA TGC ATC TCA CCC CCA GAA GGT GAT
        TTC GGA TCG TAA AAC CAA CTT TTT ACG TAG AGT GGG GGT CTT CCA CTA
        Lys Pro Ser Ile Leu Val Glu Lys Cys Ile Ser Pro Pro Glu Gly Asp>

1010            1020            1030            1040            1050
 *       *       *       *       *       *       *       *       *       *
CCT GAG TCT GCT GTG ACT GAG CTT CAA TGC ATT TGG CAC AAC CTG AGC
GGA CTC AGA CGA CAC TGA CTC GAA GTT ACG TAA ACC GTG TTG GAC TCG
Pro Glu Ser Ala Val Thr Glu Leu Gln Cys Ile Trp His Asn Leu Ser>

1060            1070            1080            1090            1100
         *       *       *       *       *       *       *       *       *       *
        TAC ATG AAG TGT TCT TGG CTC CCT GGA AGG AAT ACC AGT CCC GAC ACT
        ATG TAC TTC ACA AGA ACC GAG GGA CCT TCC TTA TGG TCA GGG CTG TGA
        Tyr Met Lys Cys Ser Trp Leu Pro Gly Arg Asn Thr Ser Pro Asp Thr>

1110            1120            1130            1140            1150
         *       *       *       *       *       *       *       *       *       *
        AAC TAT ACT CTC TAC TAT TGG CAC AGA AGC CTG GAA AAA ATT CAT CAA
        TTG ATA TGA GAG ATG ATA ACC GTG TCT TCG GAC CTT TTT TAA GTA GTT
        Asn Tyr Thr Leu Tyr Tyr Trp His Arg Ser Leu Glu Lys Ile His Gln>
```

Fig.31D.

```
        1160        1170        1180        1190        1200
         *     *     *     *     *     *     *     *     *     *
        TGT GAA AAC ATC TTT AGA GAA GGC CAA TAC TTT GGT TGT TCC TTT GAT
        ACA CTT TTG TAG AAA TCT CTT CCG GTT ATG AAA CCA ACA AGG AAA CTA
        Cys Glu Asn Ile Phe Arg Glu Gly Gln Tyr Phe Gly Cys Ser Phe Asp>

1210        1220        1230        1240
         *     *     *     *     *     *     *     *     *
        CTG ACC AAA GTG AAG GAT TCC AGT TTT GAA CAA CAC AGT GTC CAA ATA
        GAC TGG TTT CAC TTC CTA AGG TCA AAA CTT GTT GTG TCA CAG GTT TAT
        Leu Thr Lys Val Lys Asp Ser Ser Phe Glu Gln His Ser Val Gln Ile>

1250        1260        1270        1280        1290
   *     *     *     *     *     *     *     *     *     *
  ATG GTC AAG GAT AAT GCA GGA AAA ATT AAA CCA TCC TTC AAT ATA GTG
  TAC CAG TTC CTA TTA CGT CCT TTT TAA TTT GGT AGG AAG TTA TAT CAC
  Met Val Lys Asp Asn Ala Gly Lys Ile Lys Pro Ser Phe Asn Ile Val>

1300        1310        1320        1330        1340
         *     *     *     *     *     *     *     *     *
        CCT TTA ACT TCC CGT GTG AAA CCT GAT CCT CCA CAT ATT AAA AAC CTC
        GGA AAT TGA AGG GCA CAC TTT GGA CTA GGA GGT GTA TAA TTT TTG GAG
        Pro Leu Thr Ser Arg Val Lys Pro Asp Pro Pro His Ile Lys Asn Leu>

1350        1360        1370        1380        1390
         *     *     *     *     *     *     *     *     *     *
        TCC TTC CAC AAT GAT GAC CTA TAT GTG CAA TGG GAG AAT CCA CAG AAT
        AGG AAG GTG TTA CTA CTG GAT ATA CAC GTT ACC CTC TTA GGT GTC TTA
        Ser Phe His Asn Asp Asp Leu Tyr Val Gln Trp Glu Asn Pro Gln Asn>

1400        1410        1420        1430        1440
         *     *     *     *     *     *     *     *     *     *
        TTT ATT AGC AGA TGC CTA TTT TAT GAA GTA GAA GTC AAT AAC AGC CAA
        AAA TAA TCG TCT ACG GAT AAA ATA CTT CAT CTT CAG TTA TTG TCG GTT
        Phe Ile Ser Arg Cys Leu Phe Tyr Glu Val Glu Val Asn Asn Ser Gln>

1450        1460        1470        1480
         *     *     *     *     *     *     *     *     *
        ACT GAG ACA CAT AAT GTT TTC TAC GTC CAA GAG GCT AAA TGT GAG AAT
        TGA CTC TGT GTA TTA CAA AAG ATG CAG GTT CTC CGA TTT ACA CTC TTA
        Thr Glu Thr His Asn Val Phe Tyr Val Gln Glu Ala Lys Cys Glu Asn>

1490        1500        1510        1520        1530
   *     *     *     *     *     *     *     *     *     *
  CCA GAA TTT GAG AGA AAT GTG GAG AAT ACA TCT TGT TTC ATG GTC CCT
  GGT CTT AAA CTC TCT TTA CAC CTC TTA TGT AGA ACA AAG TAC CAG GGA
  Pro Glu Phe Glu Arg Asn Val Glu Asn Thr Ser Cys Phe Met Val Pro>
```

Fig.31E.

```
      1540        1550        1560        1570        1580
       *     *     *     *     *     *     *     *     *
GGT GTT CTT CCT GAT ACT TTG AAC ACA GTC AGA ATA AGA GTC AAA ACA
CCA CAA GAA GGA CTA TGA AAC TTG TGT CAG TCT TAT TCT CAG TTT TGT
Gly Val Leu Pro Asp Thr Leu Asn Thr Val Arg Ile Arg Val Lys Thr>

1590        1600        1610        1620        1630
       *     *     *     *     *     *     *     *     *     *
AAT AAG TTA TGC TAT GAG GAT GAC AAA CTC TGG AGT AAT TGG AGC CAA
TTA TTC AAT ACG ATA CTC CTA CTG TTT GAG ACC TCA TTA ACC TCG GTT
Asn Lys Leu Cys Tyr Glu Asp Asp Lys Leu Trp Ser Asn Trp Ser Gln>

1640        1650        1660        1670        1680
     *     *     *     *     *     *     *     *     *     *
GAA ATG AGT ATA GGT AAG AAG CGC AAT TCC ACA ACC GGA GAC AAA ACT
CTT TAC TCA TAT CCA TTC TTC GCG TTA AGG TGT TGG CCT CTG TTT TGA
Glu Met Ser Ile Gly Lys Lys Arg Asn Ser Thr Thr Gly Asp Lys Thr>

1690        1700        1710        1720
          *     *     *     *     *     *     *     *     *
CAC ACA TGC CCA CCG TGC CCA GCA CCT GAA CTC CTG GGG GGA CCG TCA
GTG TGT ACG GGT GGC ACG GGT CGT GGA CTT GAG GAC CCC CCT GGC AGT
His Thr Cys Pro Pro Cys Pro Ala Pro Glu Leu Leu Gly Gly Pro Ser>

1730        1740        1750        1760        1770
  *     *     *     *     *     *     *     *     *     *
GTC TTC CTC TTC CCC CCA AAA CCC AAG GAC ACC CTC ATG ATC TCC CGG
CAG AAG GAG AAG GGG GGT TTT GGG TTC CTG TGG GAG TAC TAG AGG GCC
Val Phe Leu Phe Pro Pro Lys Pro Lys Asp Thr Leu Met Ile Ser Arg>

1780        1790        1800        1810        1820
       *     *     *     *     *     *     *     *     *
ACC CCT GAG GTC ACA TGC GTG GTG GTG GAC GTG AGC CAC GAA GAC CCT
TGG GGA CTC CAG TGT ACG CAC CAC CAC CTG CAC TCG GTG CTT CTG GGA
Thr Pro Glu Val Thr Cys Val Val Val Asp Val Ser His Glu Asp Pro>

1830        1840        1850        1860        1870
       *     *     *     *     *     *     *     *     *     *
GAG GTC AAG TTC AAC TGG TAC GTG GAC GGC GTG GAG GTG CAT AAT GCC
CTC CAG TTC AAG TTG ACC ATG CAC CTG CCG CAC CTC CAC GTA TTA CGG
Glu Val Lys Phe Asn Trp Tyr Val Asp Gly Val Glu Val His Asn Ala>

1880        1890        1900        1910        1920
       *     *     *     *     *     *     *     *     *     *
AAG ACA AAG CCG CGG GAG GAG CAG TAC AAC AGC ACG TAC CGT GTG GTC
TTC TGT TTC GGC GCC CTC CTC GTC ATG TTG TCG TGC ATG GCA CAC CAG
Lys Thr Lys Pro Arg Glu Glu Gln Tyr Asn Ser Thr Tyr Arg Val Val>
```

Fig.31F.

```
              1930          1940          1950          1960
          *     *       *     *       *     *       *     *       *
        AGC GTC CTC ACC GTC CTG CAC CAG GAC TGG CTG AAT GGC AAG GAG TAC
        TCG CAG GAG TGG CAG GAC GTG GTC CTG ACC GAC TTA CCG TTC CTC ATG
        Ser Val Leu Thr Val Leu His Gln Asp Trp Leu Asn Gly Lys Glu Tyr>

1970          1980          1990          2000          2010
    *     *       *     *       *     *       *     *       *     *
        AAG TGC AAG GTC TCC AAC AAA GCC CTC CCA GCC CCC ATC GAG AAA ACC
        TTC ACG TTC CAG AGG TTG TTT CGG GAG GGT CGG GGG TAG CTC TTT TGG
        Lys Cys Lys Val Ser Asn Lys Ala Leu Pro Ala Pro Ile Glu Lys Thr>

2020          2030          2040          2050          2060
        *     *       *     *       *     *       *     *       *     *
        ATC TCC AAA GCC AAA GGG CAG CCC CGA GAA CCA CAG GTG TAC ACC CTG
        TAG AGG TTT CGG TTT CCC GTC GGG GCT CTT GGT GTC CAC ATG TGG GAC
        Ile Ser Lys Ala Lys Gly Gln Pro Arg Glu Pro Gln Val Tyr Thr Leu>

2070          2080          2090          2100          2110
          *     *       *     *       *     *       *     *       *     *
        CCC CCA TCC CGG GAG GAG ATG ACC AAG AAC CAG GTC AGC CTG ACC TGC
        GGG GGT AGG GCC CTC CTC TAC TGG TTC TTG GTC CAG TCG GAC TGG ACG
        Pro Pro Ser Arg Glu Glu Met Thr Lys Asn Gln Val Ser Leu Thr Cys>

2120          2130          2140          2150          2160
          *     *       *     *       *     *       *     *       *     *
        CTG GTC AAA GGC TTC TAT CCC AGC GAC ATC GCC GTG GAG TGG GAG AGC
        GAC CAG TTT CCG AAG ATA GGG TCG CTG TAG CGG CAC CTC ACC CTC TCG
        Leu Val Lys Gly Phe Tyr Pro Ser Asp Ile Ala Val Glu Trp Glu Ser>

2170          2180          2190          2200
          *     *       *     *       *     *       *     *       *
        AAT GGG CAG CCG GAG AAC AAC TAC AAG ACC ACG CCT CCC GTG CTG GAC
        TTA CCC GTC GGC CTC TTG TTG ATG TTC TGG TGC GGA GGG CAC GAC CTG
        Asn Gly Gln Pro Glu Asn Asn Tyr Lys Thr Thr Pro Pro Val Leu Asp>

2210          2220          2230          2240          2250
        *     *       *     *       *     *       *     *       *     *
        TCC GAC GGC TCC TTC TTC CTC TAT AGC AAG CTC ACC GTG GAC AAG AGC
        AGG CTG CCG AGG AAG AAG GAG ATA TCG TTC GAG TGG CAC CTG TTC TCG
        Ser Asp Gly Ser Phe Phe Leu Tyr Ser Lys Leu Thr Val Asp Lys Ser>

2260          2270          2280          2290          2300
          *     *       *     *       *     *       *     *       *
        AGG TGG CAG CAG GGG AAC GTC TTC TCA TGC TCC GTG ATG CAT GAG GCT
        TCC ACC GTC GTC CCC TTG CAG AAG AGT ACG AGG CAC TAC GTA CTC CGA
        Arg Trp Gln Gln Gly Asn Val Phe Ser Cys Ser Val Met His Glu Ala>
```

Fig.31G.

```
      2310            2320            2330            2340            2350
  *      *       *      *        *      *        *      *        *      *
CTG CAC AAC CAC TAC ACG CAG AAG AGC CTC TCC CTG TCT CCG GGT AAA
GAC GTG TTG GTG ATG TGC GTC TTC TCG GAG AGG GAC AGA GGC CCA TTT
Leu His Asn His Tyr Thr Gln Lys Ser Leu Ser Leu Ser Pro Gly Lys>

*
TGA
ACT
***>
```

Fig.32A.

```
         10            20            30            40
         *    *    *    *    *    *    *    *    *
ATG GTG TGG CCG GCG CGG CTC TGC GGG CTG TGG GCG CTG CTG CTC TGC
TAC CAC ACC GGC CGC GCC GAG ACG CCC GAC ACC GCC GAC GAC GAG ACG
Met Val Trp Pro Ala Arg Leu Cys Gly Leu Trp Ala Leu Leu Leu Cys>

50            60            70            80            90
    *    *    *    *    *    *    *    *    *    *
GCC GGC GGC GGG GGC GGG GGC GGG GGC GCC GCG CCT ACG GAA ACT CAG
CGG CCG CCG CCC CCG CCC CCG CCC CCG CGG CGC GGA TGC CTT TGA GTC
Ala Gly Gly Gly Gly Gly Gly Gly Ala Ala Pro Thr Glu Thr Gln>

100           110           120           130           140
         *    *    *    *    *    *    *    *    *
CCA CCT GTG ACA AAT TTG AGT GTC TCT GTT GAA AAC CTC TGC ACA GTA
GGT GGA CAC TGT TTA AAC TCA CAG AGA CAA CTT TTG GAG ACG TGT CAT
Pro Pro Val Thr Asn Leu Ser Val Ser Val Glu Asn Leu Cys Thr Val>

150           160           170           180           190
    *    *    *    *    *    *    *    *    *    *
ATA TGG ACA TGG AAT CCA CCC GAG GGA GCC AGC TCA AAT TGT AGT CTA
TAT ACC TGT ACC TTA GGT GGG CTC CCT CGG TCG AGT TTA ACA TCA GAT
Ile Trp Thr Trp Asn Pro Pro Glu Gly Ala Ser Ser Asn Cys Ser Leu>

200           210           220           230           240
    *    *    *    *    *    *    *    *    *    *
TGG TAT TTT AGT CAT TTT GGC GAC AAA CAA GAT AAG AAA ATA GCT CCG
ACC ATA AAA TCA GTA AAA CCG CTG TTT GTT CTA TTC TTT TAT CGA GGC
Trp Tyr Phe Ser His Phe Gly Asp Lys Gln Asp Lys Lys Ile Ala Pro>

250           260           270           280
    *    *    *    *    *    *    *    *    *
GAA ACT CGT CGT TCA ATA GAA GTA CCC CTG AAT GAG AGG ATT TGT CTG
CTT TGA GCA GCA AGT TAT CTT CAT GGG GAC TTA CTC TCC TAA ACA GAC
Glu Thr Arg Arg Ser Ile Glu Val Pro Leu Asn Glu Arg Ile Cys Leu>

290           300           310           320           330
    *    *    *    *    *    *    *    *    *    *
CAA GTG GGG TCC CAG TGT AGC ACC AAT GAG AGT GAG AAG CCT AGC ATT
GTT CAC CCC AGG GTC ACA TCG TGG TTA CTC TCA CTC TTC GGA TCG TAA
Gln Val Gly Ser Gln Cys Ser Thr Asn Glu Ser Glu Lys Pro Ser Ile>

340           350           360           370           380
    *    *    *    *    *    *    *    *    *
TTG GTT GAA AAA TGC ATC TCA CCC CCA GAA GGT GAT CCT GAG TCT GCT
AAC CAA CTT TTT ACG TAG AGT GGG GGT CTT CCA CTA GGA CTC AGA CGA
Leu Val Glu Lys Cys Ile Ser Pro Pro Glu Gly Asp Pro Glu Ser Ala>
```

Fig.32B.

```
       390          400          410          420          430
        *            *            *            *            *
GTG ACT GAG CTT CAA TGC ATT TGG CAC AAC CTG AGC TAC ATG AAG TGT
CAC TGA CTC GAA GTT ACG TAA ACC GTG TTG GAC TCG ATG TAC TTC ACA
Val Thr Glu Leu Gln Cys Ile Trp His Asn Leu Ser Tyr Met Lys Cys>

440          450          460          470          480
   *    *    *    *    *    *    *    *    *    *
TCT TGG CTC CCT GGA AGG AAT ACC AGT CCC GAC ACT AAC TAT ACT CTC
AGA ACC GAG GGA CCT TCC TTA TGG TCA GGG CTG TGA TTG ATA TGA GAG
Ser Trp Leu Pro Gly Arg Asn Thr Ser Pro Asp Thr Asn Tyr Thr Leu>

490          500          510          520
        *    *    *    *    *    *    *    *    *
TAC TAT TGG CAC AGA AGC CTG GAA AAA ATT CAT CAA TGT GAA AAC ATC
ATG ATA ACC GTG TCT TCG GAC CTT TTT TAA GTA GTT ACA CTT TTG TAG
Tyr Tyr Trp His Arg Ser Leu Glu Lys Ile His Gln Cys Glu Asn Ile>

530          540          550          560          570
   *    *    *    *    *    *    *    *    *    *
TTT AGA GAA GGC CAA TAC TTT GGT TGT TCC TTT GAT CTG ACC AAA GTG
AAA TCT CTT CCG GTT ATG AAA CCA ACA AGG AAA CTA GAC TGG TTT CAC
Phe Arg Glu Gly Gln Tyr Phe Gly Cys Ser Phe Asp Leu Thr Lys Val>

580          590          600          610          620
        *    *    *    *    *    *    *    *    *
AAG GAT TCC AGT TTT GAA CAA CAC AGT GTC CAA ATA ATG GTC AAG GAT
TTC CTA AGG TCA AAA CTT GTT GTG TCA CAG GTT TAT TAC CAG TTC CTA
Lys Asp Ser Ser Phe Glu Gln His Ser Val Gln Ile Met Val Lys Asp>

630          640          650          660          670
        *    *    *    *    *    *    *    *    *    *
AAT GCA GGA AAA ATT AAA CCA TCC TTC AAT ATA GTG CCT TTA ACT TCC
TTA CGT CCT TTT TAA TTT GGT AGG AAG TTA TAT CAC GGA AAT TGA AGG
Asn Ala Gly Lys Ile Lys Pro Ser Phe Asn Ile Val Pro Leu Thr Ser>

680          690          700          710          720
        *    *    *    *    *    *    *    *    *
CGT GTG AAA CCT GAT CCT CCA CAT ATT AAA AAC CTC TCC TTC CAC AAT
GCA CAC TTT GGA CTA GGA GGT GTA TAA TTT TTG GAG AGG AAG GTG TTA
Arg Val Lys Pro Asp Pro Pro His Ile Lys Asn Leu Ser Phe His Asn>

730          740          750          760
        *    *    *    *    *    *    *    *    *
GAT GAC CTA TAT GTG CAA TGG GAG AAT CCA CAG AAT TTT ATT AGC AGA
CTA CTG GAT ATA CAC GTT ACC CTC TTA GGT GTC TTA AAA TAA TCG TCT
Asp Asp Leu Tyr Val Gln Trp Glu Asn Pro Gln Asn Phe Ile Ser Arg>
```

Fig.32C.

```
        770           780           790           800           810
         *     *     *     *     *     *     *     *     *     *
        TGC   CTA   TTT   TAT   GAA   GTA   GAA   GTC   AAT   AAC   AGC   CAA   ACT   GAG   ACA   CAT
        ACG   GAT   AAA   ATA   CTT   CAT   CTT   CAG   TTA   TTG   TCG   GTT   TGA   CTC   TGT   GTA
        Cys   Leu   Phe   Tyr   Glu   Val   Glu   Val   Asn   Asn   Ser   Gln   Thr   Glu   Thr   His>

820           830           840           850           860
         *     *     *     *     *     *     *     *     *
        AAT   GTT   TTC   TAC   GTC   CAA   GAG   GCT   AAA   TGT   GAG   AAT   CCA   GAA   TTT   GAG
        TTA   CAA   AAG   ATG   CAG   GTT   CTC   CGA   TTT   ACA   CTC   TTA   GGT   CTT   AAA   CTC
        Asn   Val   Phe   Tyr   Val   Gln   Glu   Ala   Lys   Cys   Glu   Asn   Pro   Glu   Phe   Glu>

870           880           890           900           910
         *     *     *     *     *     *     *     *     *     *
        AGA   AAT   GTG   GAG   AAT   ACA   TCT   TGT   TTC   ATG   GTC   CCT   GGT   GTT   CTT   CCT
        TCT   TTA   CAC   CTC   TTA   TGT   AGA   ACA   AAG   TAC   CAG   GGA   CCA   CAA   GAA   GGA
        Arg   Asn   Val   Glu   Asn   Thr   Ser   Cys   Phe   Met   Val   Pro   Gly   Val   Leu   Pro>

920           930           940           950           960
           *     *     *     *     *     *     *     *     *     *
        GAT   ACT   TTG   AAC   ACA   GTC   AGA   ATA   AGA   GTC   AAA   ACA   AAT   AAG   TTA   TGC
        CTA   TGA   AAC   TTG   TGT   CAG   TCT   TAT   TCT   CAG   TTT   TGT   TTA   TTC   AAT   ACG
        Asp   Thr   Leu   Asn   Thr   Val   Arg   Ile   Arg   Val   Lys   Thr   Asn   Lys   Leu   Cys>

970           980           990           1000
           *     *     *     *     *     *     *     *     *
        TAT   GAG   GAT   GAC   AAA   CTC   TGG   AGT   AAT   TGG   AGC   CAA   GAA   ATG   AGT   ATA
        ATA   CTC   CTA   CTG   TTT   GAG   ACC   TCA   TTA   ACC   TCG   GTT   CTT   TAC   TCA   TAT
        Tyr   Glu   Asp   Asp   Lys   Leu   Trp   Ser   Asn   Trp   Ser   Gln   Glu   Met   Ser   Ile>

1010          1020          1030          1040          1050
   *     *     *     *     *     *     *     *     *     *
GGT   AAG   AAG   CGC   AAT   TCC   ACA   GGC   GCG   CCT   AGT   GGT   GGA   GGT   GGC   CGG
CCA   TTC   TTC   GCG   TTA   AGG   TGT   CCG   CGC   GGA   TCA   CCA   CCT   CCA   CCG   GCC
Gly   Lys   Lys   Arg   Asn   Ser   Thr   Gly   Ala   Pro   Ser   Gly   Gly   Gly   Gly   Arg>

1060          1070          1080          1090          1100
         *     *     *     *     *     *     *     *     *
        CCC   GCA   AGC   TCT   GGG   AAC   ATG   AAG   GTC   TTG   CAG   GAG   CCC   ACC   TGC   GTC
        GGG   CGT   TCG   AGA   CCC   TTG   TAC   TTC   CAG   AAC   GTC   CTC   GGG   TGG   ACG   CAG
        Pro   Ala   Ser   Ser   Gly   Asn   Met   Lys   Val   Leu   Gln   Glu   Pro   Thr   Cys   Val>

1110          1120          1130          1140          1150
             *     *     *     *     *     *     *     *     *     *
        TCC   GAC   TAC   ATG   AGC   ATC   TCT   ACT   TGC   GAG   TGG   AAG   ATG   AAT   GGT   CCC
        AGG   CTG   ATG   TAC   TCG   TAG   AGA   TGA   ACG   CTC   ACC   TTC   TAC   TTA   CCA   GGG
        Ser   Asp   Tyr   Met   Ser   Ile   Ser   Thr   Cys   Glu   Trp   Lys   Met   Asn   Gly   Pro>
```

Fig.32D.

```
            1160            1170            1180            1190            1200
              *       *       *       *       *       *       *       *       *       *
            ACC AAT TGC AGC ACC GAG CTC CGC CTG TTG TAC CAG CTG GTT TTT CTG
            TGG TTA ACG TCG TGG CTC GAG GCG GAC AAC ATG GTC GAC CAA AAA GAC
            Thr Asn Cys Ser Thr Glu Leu Arg Leu Leu Tyr Gln Leu Val Phe Leu>

1210            1220            1230            1240
              *       *       *       *       *       *       *       *       *
            CTC TCC GAA GCC CAC ACG TGT ATC CCT GAG AAC AAC GGA GGC GCG GGG
            GAG AGG CTT CGG GTG TGC ACA TAG GGA CTC TTG TTG CCT CCG CGC CCC
            Leu Ser Glu Ala His Thr Cys Ile Pro Glu Asn Asn Gly Gly Ala Gly>

1250            1260            1270            1280            1290
       *       *       *       *       *       *       *       *       *       *
     TGC GTG TGC CAC CTG CTC ATG GAT GAC GTG GTC AGT GCG GAT AAC TAT
     ACG CAC ACG GTG GAC GAG TAC CTA CTG CAC CAG TCA CGC CTA TTG ATA
     Cys Val Cys His Leu Leu Met Asp Asp Val Val Ser Ala Asp Asn Tyr>

1300            1310            1320            1330            1340
              *       *       *       *       *       *       *       *       *
            ACA CTG GAC CTG TGG GCT GGG CAG CAG CTG CTG TGG AAG GGC TCC TTC
            TGT GAC CTG GAC ACC CGA CCC GTC GTC GAC GAC ACC TTC CCG AGG AAG
            Thr Leu Asp Leu Trp Ala Gly Gln Gln Leu Leu Trp Lys Gly Ser Phe>

1350            1360            1370            1380            1390
              *       *       *       *       *       *       *       *       *       *
            AAG CCC AGC GAG CAT GTG AAA CCC AGG GCC CCA GGA AAC CTG ACA GTT
            TTC GGG TCG CTC GTA CAC TTT GGG TCC CGG GGT CCT TTG GAC TGT CAA
            Lys Pro Ser Glu His Val Lys Pro Arg Ala Pro Gly Asn Leu Thr Val>

1400            1410            1420            1430            1440
              *       *       *       *       *       *       *       *       *       *
            CAC ACC AAT GTC TCC GAC ACT CTG CTG CTG ACC TGG AGC AAC CCG TAT
            GTG TGG TTA CAG AGG CTG TGA GAC GAC GAC TGG ACC TCG TTG GGC ATA
            His Thr Asn Val Ser Asp Thr Leu Leu Leu Thr Trp Ser Asn Pro Tyr>

1450            1460            1470            1480
              *       *       *       *       *       *       *       *       *
            CCC CCT GAC AAT TAC CTG TAT AAT CAT CTC ACC TAT GCA GTC AAC ATT
            GGG GGA CTG TTA ATG GAC ATA TTA GTA GAG TGG ATA CGT CAG TTG TAA
            Pro Pro Asp Asn Tyr Leu Tyr Asn His Leu Thr Tyr Ala Val Asn Ile>

1490            1500            1510            1520            1530
       *       *       *       *       *       *       *       *       *       *
     TGG AGT GAA AAC GAC CCG GCA GAT TTC AGA ATC TAT AAC GTG ACC TAC
     ACC TCA CTT TTG CTG GGC CGT CTA AAG TCT TAG ATA TTG CAC TGG ATG
     Trp Ser Glu Asn Asp Pro Ala Asp Phe Arg Ile Tyr Asn Val Thr Tyr>
```

Fig.32E.

```
       1540          1550          1560          1570          1580
         *     *       *     *       *      *      *      *      *
CTA GAA CCC TCC CTC CGC ATC GCA GCC AGC ACC CTG AAG TCT GGG ATT
GAT CTT GGG AGG GAG GCG TAG CGT CGG TCG TGG GAC TTC AGA CCC TAA
Leu Glu Pro Ser Leu Arg Ile Ala Ala Ser Thr Leu Lys Ser Gly Ile>

1590          1600          1610          1620          1630
         *     *       *     *       *      *      *      *      *
TCC TAC AGG GCA CGG GTG AGG GCC TGG GCT CAG TGC TAT AAC ACC ACC
AGG ATG TCC CGT GCC CAC TCC CGG ACC CGA GTC ACG ATA TTG TGG TGG
Ser Tyr Arg Ala Arg Val Arg Ala Trp Ala Gln Cys Tyr Asn Thr Thr>

1640          1650          1660          1670          1680
         *     *       *     *       *      *      *      *      *
TGG AGT GAG TGG AGC CCC AGC ACC AAG TGG CAC AAC TCC TAC AGG GAG
ACC TCA CTC ACC TCG GGG TCG TGG TTC ACC GTG TTG AGG ATG TCC CTC
Trp Ser Glu Trp Ser Pro Ser Thr Lys Trp His Asn Ser Tyr Arg Glu>

1690          1700          1710          1720
         *     *       *     *       *      *      *      *      *
CCC TTC GAG CAG TCC GGA GAC AAA ACT CAC ACA TGC CCA CCG TGC CCA
GGG AAG CTC GTC AGG CCT CTG TTT TGA GTG TGT ACG GGT GGC ACG GGT
Pro Phe Glu Gln Ser Gly Asp Lys Thr His Thr Cys Pro Pro Cys Pro>

1730          1740          1750          1760          1770
   *     *       *     *       *      *      *      *      *    *
GCA CCT GAA CTC CTG GGG GGA CCG TCA GTC TTC CTC TTC CCC CCA AAA
CGT GGA CTT GAG GAC CCC CCT GGC AGT CAG AAG GAG AAG GGG GGT TTT
Ala Pro Glu Leu Leu Gly Gly Pro Ser Val Phe Leu Phe Pro Pro Lys>

1780          1790          1800          1810          1820
         *     *       *     *       *      *      *      *      *
CCC AAG GAC ACC CTC ATG ATC TCC CGG ACC CCT GAG GTC ACA TGC GTG
GGG TTC CTG TGG GAG TAC TAG AGG GCC TGG GGA CTC CAG TGT ACG CAC
Pro Lys Asp Thr Leu Met Ile Ser Arg Thr Pro Glu Val Thr Cys Val>

1830          1840          1850          1860          1870
         *     *       *     *       *      *      *      *      *
GTG GTG GAC GTG AGC CAC GAA GAC CCT GAG GTC AAG TTC AAC TGG TAC
CAC CAC CTG CAC TCG GTG CTT CTG GGA CTC CAG TTC AAG TTG ACC ATG
Val Val Asp Val Ser His Glu Asp Pro Glu Val Lys Phe Asn Trp Tyr>

1880          1890          1900          1910          1920
         *     *       *     *       *      *      *      *      *
GTG GAC GGC GTG GAG GTG CAT AAT GCC AAG ACA AAG CCG CGG GAG GAG
CAC CTG CCG CAC CTC CAC GTA TTA CGG TTC TGT TTC GGC GCC CTC CTC
Val Asp Gly Val Glu Val His Asn Ala Lys Thr Lys Pro Arg Glu Glu>
```

Fig.32F.

```
          1930        1940        1950        1960
       *     *     *     *     *     *     *     *     *
      CAG   TAC   AAC   AGC   ACG   TAC   CGT   GTG   GTC   AGC   GTC   CTC   ACC   GTC   CTG   CAC
      GTC   ATG   TTG   TCG   TGC   ATG   GCA   CAC   CAG   TCG   CAG   GAG   TGG   CAG   GAC   GTG
      Gln   Tyr   Asn   Ser   Thr   Tyr   Arg   Val   Val   Ser   Val   Leu   Thr   Val   Leu   His>

1970        1980        1990        2000        2010
       *     *     *     *     *     *     *     *     *     *
      CAG   GAC   TGG   CTG   AAT   GGC   AAG   GAG   TAC   AAG   TGC   AAG   GTC   TCC   AAC   AAA
      GTC   CTG   ACC   GAC   TTA   CCG   TTC   CTC   ATG   TTC   ACG   TTC   CAG   AGG   TTG   TTT
      Gln   Asp   Trp   Leu   Asn   Gly   Lys   Glu   Tyr   Lys   Cys   Lys   Val   Ser   Asn   Lys>

2020        2030        2040        2050        2060
       *     *     *     *     *     *     *     *     *
      GCC   CTC   CCA   GCC   CCC   ATC   GAG   AAA   ACC   ATC   TCC   AAA   GCC   AAA   GGG   CAG
      CGG   GAG   GGT   CGG   GGG   TAG   CTC   TTT   TGG   TAG   AGG   TTT   CGG   TTT   CCC   GTC
      Ala   Leu   Pro   Ala   Pro   Ile   Glu   Lys   Thr   Ile   Ser   Lys   Ala   Lys   Gly   Gln>

2070        2080        2090        2100        2110
       *     *     *     *     *     *     *     *     *     *
      CCC   CGA   GAA   CCA   CAG   GTG   TAC   ACC   CTG   CCC   CCA   TCC   CGG   GAG   GAG   ATG
      GGG   GCT   CTT   GGT   GTC   CAC   ATG   TGG   GAC   GGG   GGT   AGG   GCC   CTC   CTC   TAC
      Pro   Arg   Glu   Pro   Gln   Val   Tyr   Thr   Leu   Pro   Pro   Ser   Arg   Glu   Glu   Met>

2120        2130        2140        2150        2160
       *     *     *     *     *     *     *     *     *     *
      ACC   AAG   AAC   CAG   GTC   AGC   CTG   ACC   TGC   CTG   GTC   AAA   GGC   TTC   TAT   CCC
      TGG   TTC   TTG   GTC   CAG   TCG   GAC   TGG   ACG   GAC   CAG   TTT   CCG   AAG   ATA   GGG
      Thr   Lys   Asn   Gln   Val   Ser   Leu   Thr   Cys   Leu   Val   Lys   Gly   Phe   Tyr   Pro>

2170        2180        2190        2200
         *     *     *     *     *     *     *     *     *
      AGC   GAC   ATC   GCC   GTG   GAG   TGG   GAG   AGC   AAT   GGG   CAG   CCG   GAG   AAC   AAC
      TCG   CTG   TAG   CGG   CAC   CTC   ACC   CTC   TCG   TTA   CCC   GTC   GGC   CTC   TTG   TTG
      Ser   Asp   Ile   Ala   Val   Glu   Trp   Glu   Ser   Asn   Gly   Gln   Pro   Glu   Asn   Asn>

2210        2220        2230        2240        2250
       *     *     *     *     *     *     *     *     *     *
      TAC   AAG   ACC   ACG   CCT   CCC   GTG   CTG   GAC   TCC   GAC   GGC   TCC   TTC   TTC   CTC
      ATG   TTC   TGG   TGC   GGA   GGG   CAC   GAC   CTG   AGG   CTG   CCG   AGG   AAG   AAG   GAG
      Tyr   Lys   Thr   Thr   Pro   Pro   Val   Leu   Asp   Ser   Asp   Gly   Ser   Phe   Phe   Leu>

2260        2270        2280        2290        2300
       *     *     *     *     *     *     *     *     *
      TAT   AGC   AAG   CTC   ACC   GTG   GAC   AAG   AGC   AGG   TGG   CAG   CAG   GGG   AAC   GTC
      ATA   TCG   TTC   GAG   TGG   CAC   CTG   TTC   TCG   TCC   ACC   GTC   GTC   CCC   TTG   CAG
      Tyr   Ser   Lys   Leu   Thr   Val   Asp   Lys   Ser   Arg   Trp   Gln   Gln   Gly   Asn   Val>
```

Fig.32G.

```
        2310                2320                2330                2340                2350
   *       *       *       *       *       *       *       *       *       *
   TTC TCA TGC TCC GTG ATG CAT GAG GCT CTG CAC AAC CAC TAC ACG CAG
   AAG AGT ACG AGG CAC TAC GTA CTC CGA GAC GTG TTG GTG ATG TGC GTC
   Phe Ser Cys Ser Val Met His Glu Ala Leu His Asn His Tyr Thr Gln>

2360                2370                2380
       *       *       *       *       *       *
   AAG AGC CTC TCC CTG TCT CCG GGT AAA TGA
   TTC TCG GAG AGG GAC AGA GGC CCA TTT ACT
   Lys Ser Leu Ser Leu Ser Pro Gly Lys ***>
```

RECEPTOR BASED ANTAGONISTS AND METHODS OF MAKING AND USING

This application claims priority of U.S. Provisional application No. 60/101,858 filed Sep. 25, 1998. Throughout this application various publications are referenced. The disclosures of these publications in their entireties are hereby incorporated by reference into this application.

BACKGROUND OF THE INVENTION

Although discovered for varying biological activities, ciliary neurotrophic factor (CNTF), leukemia inhibitory factor (LIF), oncostatin M (OSM) and interleukin-6 (IL-6) comprise a defined family of cytokines (referred to herein as the "CNTF family" of cytokines). These cytokines are grouped together because of their distant structural similarities [Bazan, J. Neuron 7: 197–208 (1991); Rose and Bruce, Proc. Natl. Acad. Sci. USA 88: 8641–8645 (1991)], and, perhaps more importantly, because they share "β" signal-transducing receptor components [Baumann, et al., J. Biol. Chem. 265:19853–19862 (1993); Davis, et al., Science 260: 1805–1808 (1993); Gearing et al., Science 255:1434–1437 (1992); Ip et al., Cell 69: 1121–1132 (1992); Stahl, et al., J. Biol. Chem. 268: 7628–7631 (1993); Stahl and Yancopoulos, Cell 74: 587–590 (1993)]. Receptor activation by this family of cytokines results from either homo- or hetero-dimerization of these β components [Davis, et al. Science 260: 1805–1808 (1993), Murakami, et al., Science 260: 1808–1810 (1993); Stahl and Yancopoulos, Cell 74: 587–590 (1993)]. IL-6 receptor activation requires homodimerization of gp130 [Murakami, et al. Science 260: 1808–1810 (1993), Hibi, et al., Cell 63: 1149–1157 (1990)], a protein initially identified as the IL-6 signal transducer [Hibi, et al., Cell 63: 1149–1157 (1990)]. CNTF, LIF and OSM receptor activation results from heterodimerization between gp130 and a second gp130-related protein known as LIFRβ [Davis, et al., Science 260: 1805–1808 (1993)], that was initially identified by its ability to bind LIF [Gearing et al., EMBO J. 10: 2839–2848 (1991)].

In addition to the β components, some of these cytokines also require specificity-determining "α" components that are more limited in their tissue distribution than the β components, and thus determine the cellular targets of the particular cytokines [Stahl and Yancopoulos, Cell 74: 587–590 (1993)]. Thus, LIF and OSM are broadly acting factors that may only require the presence of gp130 and LIFRβ on responding cells, while CNTF requires CNTFRα [Stahl and Yancopoulos, Cell 74: 587–590 (1993)] and IL-6 requires IL-6Rα [Kishimoto, et al., Science 258: 593–597 (1992)]. Both CNTFRα (Davis et al., Science 259:1736–1739 (1993) and IL-6Rα [Hibi, et al. Cell 63:1149–1157, Murakami, et al., Science 260:1808–1810 (1990); Taga, et al., Cell 58:573–581 (1989)] can function as soluble proteins, consistent with the notion that they do not interact with intracellular signaling molecules but that they serve to help their ligands interact with the appropriate signal transducing β subunits [Stahl and Yancopoulos, Cell 74: 587–590 (1993)].

Additional evidence from other cytokine systems also supports the notion that dimerization provides a common mechanism by which all cytokine receptors initiate signal transduction. Growth hormone (GH) serves as perhaps the best example in this regard. Crystallographic studies have revealed that each GH molecule contains two distinct receptor binding sites, both of which are recognized by the same binding domain in the receptor, allowing a single molecule of GH to engage two receptor molecules [de Vos, et al., Science 255: 306–312 (1992)]. Dimerization occurs sequentially, with site 1 on the GH first binding to one receptor molecule, followed by the binding of site 2 to a second receptor molecule [Fuh, et al., Science 256: 1677–1680 (1992)]. Studies with the erythropoietin (EPO) receptor are also consistent with the importance of dimerization in receptor activation, as EPO receptors can be constitutively activated by a single amino acid change that introduces a cysteine residue and results in disulfide-linked homodimers [Watowich, et al., Proc. Natl. Acad. Sci. USA 89:2140–2144 (1992)].

In addition to homo- or hetero-dimerization of β subunits as the critical step for receptor activation, a second important feature is that formation of the final receptor complex by the CNTF family of cytokines occurs through a mechanism whereby the ligand successively binds to receptor components in an ordered manner [Davis, et al. Science 260:1805–1818 (1993); Stahl and Yancopoulos, Cell 74: 587–590 (1993)]. Thus CNTF first binds to CNTFRα, forming a complex which then binds gp130 to form an intermediate (called here the αβ1 intermediate) that is not signaling competent because it has only a single β component, before finally recruiting LIFRβ to form a heterodimer of β components which then initiates signal transduction. Although a similar intermediate containing IL-6 bound to IL-6Rα and a single molecule of gp130 has not been directly isolated, we have postulated that it does exist by analogy to its distant relative, CNTF, as well as the fact that the final active IL-6 receptor complex recruits two gp130 monomers. Altogether, these findings led to a proposal for the structure of a generic cytokine receptor complex (FIG. 1) in which each cytokine can have up to 3 receptor binding sites: a site that binds to an optional α specificity-determining component (α site), a site that binds to the first β signal-transducing component (β1 site), and a site that binds to the second β signal-transducing component (β2 site) [Stahl and Yancopoulos, Cell 74: 587–590 (1993)]. These 3 sites are used in sequential fashion, with the last step in complex formation—resulting in β component dimerization—critical for initiating signal transduction [Davis, et al. Science 260:1805–1818 (1993)]. Knowledge of the details of receptor activation and the existence of the non-functional β1 intermediate for CNTF has led to the finding that CNTF is a high affinity antagonist for IL-6 under certain circumstances, and provides the strategic basis for designing ligand or receptor-based antagonists for the CNTF family of cytokines as detailed below.

Once cytokine binding induces receptor complex formation, the dimerization of β components activates intracellular tyrosine kinase activity that results in phosphorylation of a wide variety of substrates [Ip, et al. Cell 69:121–1132 (1992)]. This activation of tyrosine kinase appears to be critical for downstream events since inhibitors that block the tyrosine phosphorylations also prevent later events such as gene inductions [Ip, et al., Cell 69:121–1132 (1992); Nakajima and Wall, Mol. Cell. Biol. 11:1409–1418 (1991)]. Recently, we have demonstrated that a newly discovered family of non-receptor tyrosine kinases that includes Jak1, Jak2, and Tyk2 (referred to as the Jak/Tyk kinases) [Firmbach-Kraft, et al., Oncogene 5:1329–1336 (1990); Wilks, et al., Mol. Cell. Biol. 11: 2057–2065 (1991] and that are involved in signal transduction with other cytokines [Argetsinger, et al., Cell 74:237–244 (1993); Silvennoinen, et al., Proc. Natl. Acad. Sci. USA 90:8429–8433 (1993); Velazquez, et al., Cell 70: 313–322 (1992); Witthuhn, et al., Cell 74:227–236 (1993)], preassociate with the cytoplasmic domains of the β subunits gp130 and LIFRβ in the absence of ligand, and become tyrosine phosphorylated and activated upon ligand addition [Stahl et al., Science 263:92–95 (1994)]. Therefore these kinases appear to be the most proximal step of intracellular signal transduction activated inside the cell as a result of ligand binding outside of the cell. Assay systems for screening collections of small molecules for specific agonist or antagonist activities based on this system are described below.

The CNTF family of cytokines play important roles in a wide variety of physiological processes that provide potential therapeutic applications for both antagonists and agonists.

SUMMARY OF THE INVENTION

An object of the present invention is the production of cytokine antagonists that are useful in the treatment of cytokine related diseases or disorders.

Another object of the invention is the use of the disclosed cytokine antagonists for the treatment of cytokine related diseases or disorders. For example, an IL-6 antagonist described herein may be used for the treatment of osteoporosis, the primary and second effects of cancers, including multiple myeloma, or cachexia.

Another object of the invention is the development of screening systems useful for identifying novel agonists and antagonists of cytokine receptors. Another object of the invention is the development of screening systems useful for identifying small molecules that act as agonists or antagonists of the cytokines.

Another object of the invention is the development of screening systems useful for identifying novel agonists and antagonists of members of the CNTF family of cytokines.

Another object of the invention is the development of screening systems useful for identifying small molecules that act as agonists or antagonists of the CNTF family of cytokines.

BRIEF DESCRIPTION OF THE FIGURES

FIGS. 4A–B (SEQ ID NO: 7). The amino acid sequence of human gp130-Fc-His$_6$ (SEQ ID NO: 7). Amino acids 1 to 619 are from human gp130 (Hibi et al., Cell 63:1149–1157 (1990). Note that amino acid number 2 has been changed from a Leu to a Val in order to accommodate a Kozak sequence in the coding DNA sequence. The signal peptide of gp130-Fc-His$_6$ has been italicized (amino acids 1 to 22). The Ser-Gly bridge is shown in bold type (amino acids 620, 621). Amino acids 662 to 853 are from the Fc domain of human IgG1 (Lewis, et al., J. Immunol. 151:2829–2838 (1993). (†) mark the two cysteines (amino acids number 632 and 635) of the IgG hinge preceding the Fc that form the inter-chain disulfide bridges that link two Fc domains. The hexahistine tag is shown in bold/italic type (amino acids 854 to 859). (•) shows the position of the STOP codon.

FIG. 5 (SEQ ID NO: 8). The amino acid sequence of human IL-6Rα-Fc (SEQ ID NO: 8). Key: Amino acids 1 to 358 are from human IL-6Rα (Yamasaki, et al., Science 241:825–828 (1988). Note that amino acid number 2 has been changed from a Leu to a Val in order to accomodate a Kozak sequence in the coding DNA sequence. The signal peptide of IL-6Rα -Fc has been italicized (amino acids 1 to 19). The Ala-Gly bridge is shown in bold type (amino acids 359, 360). Amino acids 361 to 592 are from the Fc domain of human IgG1 (Lewis et al., J. Immunol. 151:2829–2838 (1993). (†) mark the two cysteines (amino acids number 371 and 374) of the IgG hinge preceding the Fc that form the inter-chain disulfide bridges that link two Fc domains. (•) shows the position of the STOP codon.

FIG. 6: The CNTF/IL-6/IL-11 receptor system. The ordered formation of the hexameric signal transducing receptor complex is depicted schematically. The cytokine associates with the Rα component to form an obligatory cytokine•Rα complex (Kd is about 5 nM). This low affinity complex next associates with the first signal transducing component, marked β1, to form a high affinity cytokine•Rα•β1 complex (Kd is about 10 pM). In the case of IL-6Rα, this component is gp130. This trimeric high affinity complex subsequently associates with another such complex. Formation of this complex results in signal transduction as it involves dimerization of two signal transducing components, marked β1 and β2 respectively (adapted from (Ward et al., J. Bio. Chem. 269:23286–23289 (1994); Stahl and Yancopoulos, J. Neurobiology 25:1454–1466 (1994); Stahl and Yancopoulos, Cell 74:587–590 (1993).

FIG. 7: Design of heterodimeric receptor-based ligand traps for IL-6. The heterodimeric ligand trap is comprised of two interdisulfide linked proteins, gp130-Fc and IL-6Rα-Fc. The gp130-Fc•IL-6Rα-Fc complex (upper panel) is shown to mimic the high affinity cytokine•Rα•β1 complex (lower panel). The ligand trap functions as an antagonist by sequestering IL-6 and thus rendering unavailable to interact with the native receptors on IL-6-responsive cells.

FIGS. 9A–B (SEQ ID NO: 9). Amino acid sequence of gp130-Cγ1 (SEQ ID NO: 9). Key: Amino acids 1 to 619 are from human gp130 (Hibi, et al., Cell 63:1149–1157 (1990). Ser-Gly bridge is shown in bold type. Amino acids 662 to 651 are from the constant region of human IgG1 (Lewis et al., J. Immunol. 151:2829–2838 (1993). (*) shows the position of the STOP codon.

FIG. 10 (SEQ ID NO: 10). Amino acid sequence of gp130Δ3fibro (SEQ ID NO: 10). Key: Amino acids 1 to 330 are from human gp130 (Hibi et al., Cell 63:1149–1157 (1990). Other symbols as described in FIGS. 9A–B (SEQ ID NO: 9).

FIG. 11 (SEQ ID NO: 11). Amino acid sequence of J-CH1 (SEQ ID NO: 11). Key: The Ser-Gly bridge is shown in bold, the J-peptide is shown in italics, the $C_H1$ domain is underlined.

FIG. 12 (SEQ ID NO: 12). Amino acid sequence of Cγ4 (SEQ ID NO: 12). Key: The Ser-Gly bridge is shown in bold type. Amino acids 2 to 239 comprise the Cγ4 sequence.

FIG. 13 (SEQ ID NO: 13). Amino acid sequence of κ-domain (SEQ ID NO: 13). Key: The Ser-Gly bridge is shown in bold type. Amino acids 2 to 108 comprise the κ domain. The C-terminal cysteine (amino acid 108) is that involved in the disulfide bond of the κ domain with the $C_H1$ domain of Cγ.

FIG. 14 (SEQ ID NO: 14). Amino acid sequence of λ-domain (SEQ ID NO: 14). Key: The Ser-Gly bridge is shown in bold type. Amino acids 2 to 106 comprise the λ domain (Cheung, et al., J. Virol. 66: 6714–6720 (1992). The C-terminal cysteine (amino acid 106) is that involved in the disulfide bond of the λ domain with the $C_H1$ domain of Cγ.

FIG. 15 (SEQ ID NO: 15). Amino acid sequence of the soluble IL-6Rα domain (SEQ ID NO: 15). Key: Amino acids 1 to 358 comprise the soluble IL-6Rα domain (Yamasaki, et al., Science 241:825–828 (1988). The Ala-Gly bridge is shown in bold type.

FIG. 16 (SEQ ID NO: 16). Amino acid sequence of the soluble IL-6Rα313 domain (SEQ ID NO: 16): Key: Amino acids 1 to 313 comprise the truncated IL-6Rα domain (IL-6Rα313). The Thr-Gly bridge is shown in bold type.

(FIG. 19A) Two different ligand traps are depicted schematically and listed according to their ability to bind protein A. gp130-Fc.IL-6Rα-Fc (GF6F) binds protein A via its Fc-domains, whereas gp130-C$_H$1.IL-6Rα-κ (G16K) does not bind to protein A. (FIG. 19B) Anti-kappa western blotting of proteins precipitated with Protein A-Sepharose from mixtures of GF6F+IL-6, G16K+IL-6, or GF6F plus G16K+IL-6, as marked.

FIG. 20. Inhibition of IL-6-dependent XG-1 cell proliferation. XG-1 cells [Zhang, et al., Blood 83:3654–3663 (1994)] were prepared for a proliferation assay by starving the cells from IL-6 for 5 hours. Assays were set up in 96-well tissue culture dishes in RPM +10% fetal calf serum +penicillin/streptomycin +0.050 nM 2-mercaptoethanol +glutamine. 0.1 ml of that media was used per well. Cells were suspended at a density of 250,000 per ml at the start of the assay. 72 hours post addition of IL-6±ligands traps or antibodies, an MT assay was performed as described (Panayotatos et al. Biochemistry 33:5813–5818 (1994). The different ligand traps utilized are listed.

FIGS. 21A–21D (SEQ ID NOS: 17 and 18)—Nucleotide sequence (SEQ ID NO: 17) encoding and deduced amino acid sequence (SEQ ID NO: 18) of fusion polypeptide designated 424 which is capable of binding the cytokine IL-4 to form a nonfunctional complex.

FIGS. 22A–22D (SEQ ID NOS: 19 and 20)—Nucleotide sequence (SEQ ID NO: 19) encoding and deduced amino acid sequence (SEQ ID NO: 20) of fusion polypeptide designated 603 which is capable of binding the cytokine IL-4 to form a nonfunctional complex.

FIGS. 23A–23D (SEQ ID NOS: 21 and 22)—Nucleotide sequence (SEQ ID NO: 21) encoding and deduced amino acid sequence (SEQ ID NO: 22) of fusion polypeptide designated 622 which is capable of binding the cytokine IL-4 to form a nonfunctional complex.

FIGS. 24A–24F (SEQ ID NOS: 23 and 24)—Nucleotide sequence (SEQ ID NO: 23) encoding and deduced amino acid sequence (SEQ ID NO: 24) of fusion polypeptide designated 412 which is capable of binding the cytokine IL-6 to form a nonfunctional complex.

FIGS. 25A–25F (SEQ ID NOS: 25 and 26)—Nucleotide sequence (SEQ ID NO: 25) encoding and deduced amino acid sequence (SEQ ID NO: 26) of fusion polypeptide designated 616 which is capable of binding the cytokine IL-6 to form a nonfunctional complex.

FIGS. 26A–26E (SEQ ID NOS: 27 and 28)—Nucleotide sequence (SEQ ID NO: 27) encoding and deduced amino acid sequence (SEQ ID NO: 28) of fusion polypeptide designated 569 which is capable of binding the cytokine IL-1 to form a nonfunctional complex.

FIGS. 31A–31G (SEQ ID NOS: 29 and 30)—The nucleotide (SEQ ID NO: 29) and encoded amino acid sequence (SEQ ID NO: 30) of the IL-4Rα.IL-13Rα1.Fc single chain trap construct is set forth.

FIGS. 32A–32G (SEQ ID NOS: 31 and 32)—The nucleotide (SEQ ID NO: 31) and encoded amino acid sequence (SEQ ID NO: 32) of the IL-13Rα1.IL-4Rα.Fc single chain trap construct is set forth.

DETAILED DESCRIPTION OF THE INVENTION

Figure 1:
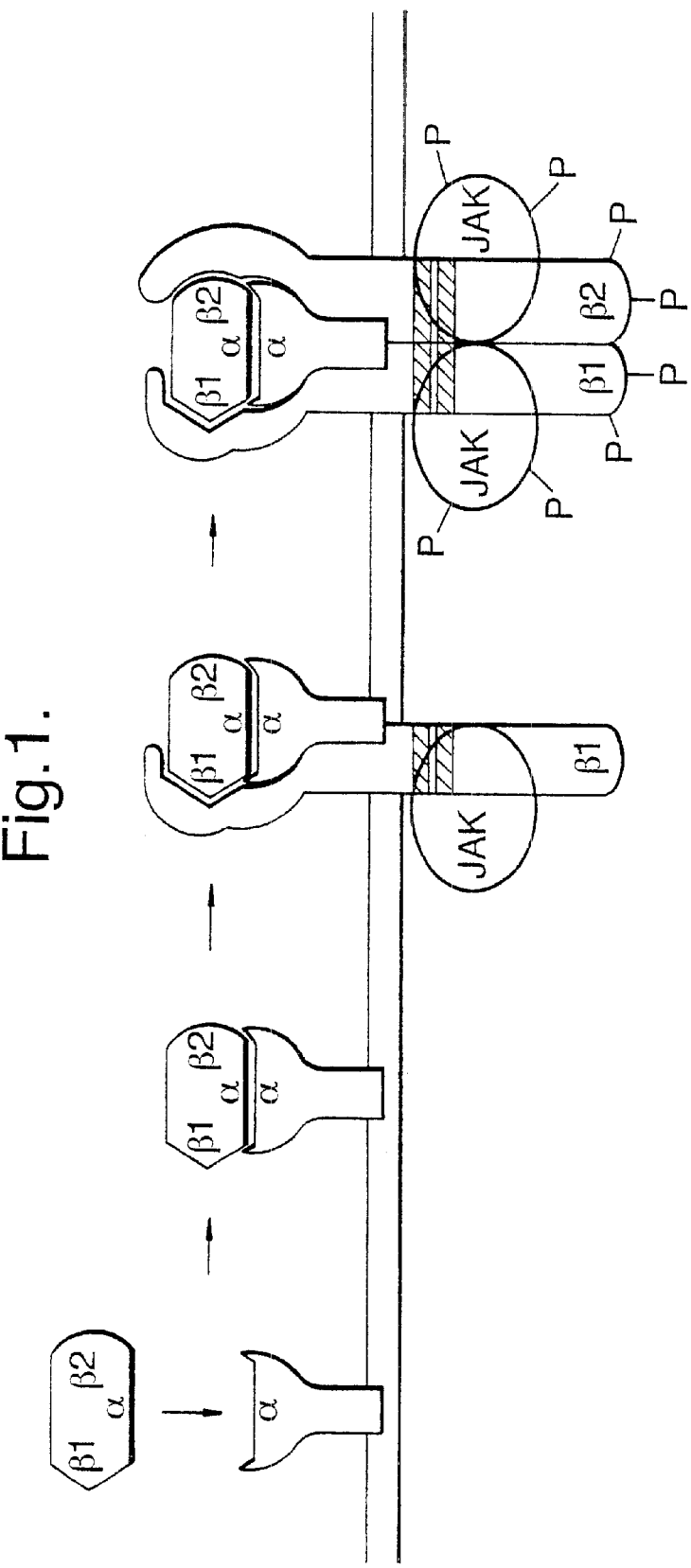
FIG. 1: Ordered binding of receptor components in a model of a generic cytokine receptor. The model indicates that cytokines contain up to 3 receptor binding sites and interact with their receptor components by binding first the optional α component, followed by binding to β1, and then β2. The β components for many cytokine receptors interact through membrane proximal regions (shaded boxes) with the Jak/Tyk family of cytoplasmic protein tyrosine kinases. Only upon dimerization of β components is signal transduction initiated, as schematized by the tyrosine phosphorylations (P) of the β components and the Jak/Tyk kinases.

The present invention provides an isolated nucleic acid molecule encoding a fusion polypeptide capable of binding a cytokine to form a nonfunctional complex comprising:

a) a nucleotide sequence encoding a first fusion polypeptide component comprising the amino acid sequence of the cytokine binding portion of the extracellular domain of the specificity determining component of the cytokine's receptor;

b) a nucleotide sequence encoding a second fusion polypeptide component comprising the amino acid sequence of the cytokine binding portion of the extracellular domain of the signal transducing component of the cytokine's receptor; and c) a nucleotide sequence encoding a third fusion polypeptide component comprising the amino acid sequence of a multimerizing component. By "cytokine binding portion" what is meant is the minimal portion of the extracellular domain necessary to bind the cytokine. It is accepted by those of skill in the art that a defining characteristic of a cytokine receptor is the presence of the two fibronectin-like domains that contain canonical cysteines and of the WSXWS box (Bazan, J. F., 1990, PNAS 87: 6934–6938). Sequences encoding the extracellular domains of the binding component of the cytokine's receptor and of the signal transducing component of the cytokine's receptor may also be used to create the fusion polypeptide of the invention. Similarly, longer sequences encoding larger portions of the components of the cytokine's receptor may be used. However, it is contemplated that fragments smaller than the extracellular domain will function to bind the cytokine and therefore, the invention contemplates fusion polypeptides comprising the minimal portion of the extracellular domain necessary to bind the cytokine as the cytokine binding portion.

The invention comprises a "specificity determining component" of a cytokine's receptor and a "signal transducing component" of the cytokine's receptor. Regardless of the nomenclature used to designate a particular component or subunit of a cytokine receptor, one skilled in the art would recognize which component or subunit of a receptor is responsible for determining the cellular target of the cytokine, and thus would know which component constitutes the "specificity determining component."

Similarly, regardless of the nomenclature used, one of skill in the art would know which component or subunit of a receptor would constitute the "signal transducing component." As used herein, the "signal transducing component" is a component of the native receptor which is not the specificity determining component and which, does not bind or weakly binds the cytokine in the absence of the specificity determining component. In the native receptor, the "signal transducing component" may participate in signalling.

For example, while some cytokine receptors have components designated α and β, the IL-4 receptor has a signal transducing component referred to as IL-2Rγ. However, regardless of what name is associated with that component, one skilled in the art would know which component of the IL-4 receptor is the signal transducing component. Thus to practice the present invention and create a high affinity trap for IL-4, one of skill in the art would create an isolated nucleic acid comprising a nucleotide sequence encoding a first fusion polypeptide component comprising the amino acid sequence of the cytokine binding portion of the extracellular domain of the specificity determining component of the IL-4 receptor (IL-4Rα); a nucleotide sequence encoding a second fusion polypeptide component comprising the amino acid sequence of the cytokine binding portion of the extracellular domain of the signal transducing component of the IL-4 receptor (IL-2Rγ); and a nucleotide sequence encoding a third fusion polypeptide component comprising the amino acid sequence of a multimerizing component (for example, an Fc domain of IgG) to create a high affinity trap for IL-4.

Some further examples of the receptor components that may be used to prepare cytokine antagonists according to the invention are set forth in Table 1. The Table 1 sets forth, by way of example but not by way of limitation, some of the varied nomenclature used in the scientific literature to describe those components which function as specificity determining components and those which function as signal transducing components of certain cytokine receptors.

TABLE 1

| Cytokine | Specificity determining Component | Signal transducing Component |
| --- | --- | --- |
| Interleukin-1 (IL-1) | Type I IL-1R (ref. 8)<br>Type II IL-1R (ref. 8)<br>IL-1RI (ref. 11)<br>IL-1RII (ref. 11) | IL-1R AcP (refs. 8, 11) |
| Interleukin-2 (IL-2) | α-subunit (ref. 2)<br>α-chain (ref. 3)<br>IL-2Rα (ref. 1) | β-chain (ref. 3)<br>β-subunit (ref. 2)<br>γ-chain (ref. 3)<br>IL-2Rβ (refs. 1, 10)<br>IL-2Rγ (refs. 1, 10) |
| Interleukin-3 (IL-3) | IL-3Rα (ref. 1)<br>α-subunit (ref. 2)<br>α-receptor component (ref. 5) | β$_c$ (ref. 1)<br>β-subunit (ref. 2)<br>β-chain (ref. 3)<br>β-receptor component (ref. 5) |
| Interleukin-4 (IL-4) | IL-4R (ref. 1) | γ -chain (ref. 3)<br>IL-2Rγ (ref. 1) |
| Interleukin-5 (IL-5) | IL-5Rα (ref. 1)<br>α-subunit (ref. 2)<br>α-receptor component (ref. 5) | β$_c$ (ref. 1)<br>β-subunit (ref. 2)<br>β-chain (ref. 3)<br>β-receptor component (ref. 5) |
| Granulocyte macrophage colony stimulating factor (GM-CSF) | α-receptor component (ref. 5)<br>α-subunit (ref. 2)<br>GMRα (refs. 1, 2) | β-receptor component (ref. 5)<br>β-subunit (ref. 2)<br>β-chain (ref. 3)<br>β$_c$ (ref. 1)<br>GMRβ (refs. 1, 2) |
| Leukemia inhibitory factor (LIF) | LIFBP (ref. 1)<br>α-receptor component (ref. 5) | gp130 (refs. 1, 3)<br>β-receptor component (ref. 5) |
| Interleukin-11 (IL-11) | α-chain (ref. 4)<br>NR1 (ref. 4) | gp130 (ref. 4) |
| Interleukin-15 (IL-15) | IL-15Rα (ref. 10) | IL-2Rβ (ref. 10)<br>IL-2Rγ (ref. 10) |
| Interferon-γ (IFNγ) | IFN-γγ (ref. 7)<br>IFN-γR1 (ref. 7) | AF-1 (ref. 7)<br>IFN-γR2 (ref. 7) |
| TGFβ | Type II (refs. 6, 9) | Type I (refs. 6, 9) |

Only a few of the multitude of references are cited in Table 1, and they are set forth as follows:

1. Sato and Miyajima, Current Opinions in Cell Biology 6: 174–179 (1994)—See page 176, lines 9–16;
2. Miyajima, et al., Annual Review of Immunology 10: 295–331 (1992)—See page 295, line 4 to page 296, line 1; page 305, last paragraph;
3. Kondo, et al., Science 262: 1874–1877 (1993)—See page 1874, cols. 1 & 2;

4. Hilton, et al., EMBO Journal 13: 4765–4775 (1994)—See page 4766, col. 1, lines 20–24;
5. Stahl and Yancopoulos, Cell 74: 587–590 (1993)—See page 587, column 2, lines 15–22;
6. Bassing, et al., Journal of Biological Chemistry 269: 14861–14864 (1994)—See page 14861, col. 2, lines 1–9 and 21–28;
7. Kotenko, et al., Journal of Biological Science 270: 20915–20921 (1995)—See page 20915, lines 1–5 of the abstract;
8. Greenfeder, et al., Journal of Biological Chemistry 270: 13757–13765 (1995)—See page 13757, col. 1, line 6 to col. 2, line 3 and col. 2, lines 10–12; page 13764, col. 2, last 3 lines and page 13765, col. 1, lines 1–7;
9. Lebrun and Vale, Molecular Cell Biology 17: 1682–1691 (1997)—See page 1682, Abstract lines 2–6;
10. Kennedy and Park, Journal of Clinical Immunology 16: 134–143 (1996)—See page 134, lines 1–7 of the abstract; page 136, col 2., lines 1–5;
11. Wesche, et al., Journal of Biological Chemistry 272: 7727–7731 (1997) See page 7731, lines 20–26.

Kotenko, et al. recently identified the IL-10R2 (IL-10Rβ) chain which is reported to serve as an accessory chain that is essential for the active IL-10 receptor complex and for initiating IL-10 induced signal transduction events (S. V. Kotenko, et al., The EMBO Journal, 1997, Vol. 16: 5894–5903). Additional cytokines and their receptors are described in Appendix II, page A:9 of *Immunobiology, The Immune System In Health and Disease,* 2nd Edition, by Charles A. Janeway, Jr. and Paul Travers, published by Current Biology Ltd./Garland Publishing Inc., copyright 1996.

In preparing the nucleic acid sequence encoding the fusion polypeptide of the invention, the first, second, and third components of the fusion polypeptide are encoded in a single strand of nucleotides which, when expressed by a host vector system, produces a monomeric species of the fusion polypeptide. The monomers thus expressed then multimerize due to the interactions between the multimerizing components (the third fusion polypeptide components). Producing the fusion polypeptides in this manner avoids the need for purification of heterodimeric mixtures that would result if the first and second components were produced as separate molecules and then multimerized. For example, U.S. Pat. No. 5,470,952 issued Nov. 28, 1995 describes the production of heterodimeric proteins that function as CNTF or IL-6 antagonists. The heterodimers are purified from cell lines cotransfected with the appropriate alpha and beta components. Heterodimers are then separated from homodimers using methods such as passive elution from preparative, nondenaturing polyacrylamide gels or by using high pressure cation exchange chromatography. The need for this purification step is avoided by the methods of the present invention.

In addition, PCT International Application WO 96/11213 published Apr. 18 1996 entitled Dimeric IL-4 Inhibitors states that the applicant has prepared homodimers in which two IL-4 receptors are bound by a polymeric spacer and has prepared heterodimers in which an IL-4 receptor is linked by a polymeric spacer to an IL-2 receptor gamma chain. The polymeric spacer described is polyethylene glycol (PEG). The two receptor components, IL-4R and IL-2Rgamma are separately expressed and purified. Pegylated homodimers and heterodimers are then produced by joining the components together using bi-functional PEG reagents. It is an advantage of the present invention that it avoids the need for such time consuming and costly purification and pegylation steps.

In one embodiment of the invention, the nucleotide sequence encoding the first component is upstream of the nucleotide sequence encoding the second component. In another embodiment of the invention, the nucleotide sequence encoding the first component is downstream of the nucleotide sequence encoding the second component. Further embodiments of the invention may be prepared in which the order of the first, second and third fusion polypeptide components is rearranged. For example, if the nucleotide sequence encoding the first component is designated 1, the nucleotide sequence encoding the second component is designated 2, and the nucleotide sequence of the third component is designated 3, then the order of the components in the isolated nucleic acid of the invention as read from 5' to 3' may be any of the following six combinations: 1,2,3; 1,3,2; 2,1,3; 2,3,1; 3,1,2; or 3,2,1.

In further embodiments of the invention, the cytokine bound by the fusion polypeptide may be a member of the hematopoietin family of cytokines selected from the group consisting of interleukin-2, interleukin-3, interleukin-4, interleukin-5, interleukin-6, interleukin-7, interleukin-9, interleukin-11, interleukin-13, interleukin-15, granulocyte macrophage colony stimulating factor, oncostatin M, and leukemia inhibitory factor.

In additional embodiments of the invention, the cytokine bound by the fusion polypeptide may be a member of the interferon family of cytokines selected from the group consisting of IFN-gamma, IFN-alpha, and IFN-beta.

In additional embodiments of the invention, the cytokine bound by the fusion polypeptide may be a member of the immunoglobulin superfamily of cytokines selected from the group consisting of B7.1 (CD80) and B7.2 (B70).

In still further embodiments of the invention, the cytokine bound by the fusion polypeptide may be a member of the TNF family of cytokines selected from the group consisting of TNF-alpha, TNF-beta, LT-beta, CD40 ligand, Fas ligand, CD 27 ligand, CD 30 ligand, and 4-1BBL.

In additional embodiments of the invention, the cytokine bound by the fusion polypeptide may be a cytokine selected from the group consisting of interleukin-1, interleukin-10, interleukin-12, interleukin-14, interleukin-18, and MIF.

Because specificity determination and signal transduction occurs by a similar mechanism in the TGF-β/BMP family of cytokines (See D. Kingsley, Genes & Development, 1994, 8: 133–146; J. Wrana, Miner Electrolyte Metab, 24: 120–130 (1998); R. Derynck and X. Feng, Biochimica et Biophysica Acta 1333 (1997) F105–F150; and J. Massague and F. Weis-Garcia, "Serine/threonine Kinase Receptors: Mediators of Transforming Growth Factor Beta Family Signals" In Cancer Surveys, Vol. 27: Cell Signalling, 1996, Imperial Cancer Research Fund) the present invention may be used to produce high affinity antagonists for cytokines that are members of the TGF-β/BMP family.

Therefore, in additional embodiments of the invention, the cytokine bound by the fusion polypeptide may be a member of the TGF-β/BMP family selected from the group consisting of TGF-β1, TGF-β2, TGF-β3, BMP-2, BMP-3a, BMP-3b, BMP-4, BMP-5, BMP-6, BMP-7, BMP-8a, BMP-8b, BMP-9, BMP-10, BMP-11, BMP-15, BMP-16, endometrial bleeding associated factor (EBAF), growth differentiation factor-1 (GDF-1), GDF-2, GDF-3, GDF-5, GDF-6, GDF-7, GDF-8, GDF-9, GDF-12, GDF-14, mullerian inhibiting substance (MIS), activin-1, activin-2, activin-3, activin-4, and activin-5.

In alternative embodiments of the invention, the specificity determining component, the signal transducing component, or both, may be substituted for by a single chain Fv. A single chain Fv (scFv) is a truncated Fab having only the V region of a heavy chain linked by a stretch of synthetic peptide to a V region of a light chain. See, for example, U.S. Pat. Nos. 5,565,332; 5,733,743; 5,837,242; 5,858,657; and 5,871,907 assigned to Cambridge Antibody Technology Limited incorporated by reference herein. Thus the present invention contemplates, for example, an isolated nucleic acid molecule encoding a fusion polypeptide capable of binding a cytokine to form a nonfunctional complex comprising a nucleotide sequence encoding a first fusion polypeptide component comprising the amino acid sequence of the cytokine binding portion of the extracellular domain of the specificity determining component of the cytokine's receptor; a nucleotide sequence encoding a second fusion polypeptide component comprising the amino acid sequence of an scFv capable of binding the cytokine at a site different from the site at which the cytokine binding portion of the extracellular domain of the specificity determining component of the cytokine's receptor binds; and a nucleotide sequence encoding a third fusion polypeptide component comprising the amino acid sequence of a multimerizing component. Alternatively, the specificity determining component may be substituted for by a scFv that binds to a site on the cytokine different from the site at which the signal transducing component binds. Thus the invention contemplates an isolated nucleic acid molecule encoding a fusion polypeptide capable of binding a cytokine to form a nonfunctional complex comprising a nucleotide sequence encoding a first fusion polypeptide component comprising the amino acid sequence of a scFv that binds to a site on the cytokine different from the site at which the cytokine binding portion of the extracellular domain of the signal transducing component of the cytokine's receptor binds; a nucleotide sequence encoding a second fusion polypeptide component comprising the amino acid sequence of the cytokine binding portion of the extracellular domain of the signal transducing component of the cytokine's receptor; and a nucleotide sequence encoding a third fusion polypeptide component comprising the amino acid sequence of a multimerizing component.

In another embodiment, the invention contemplates an isolated nucleic acid molecule encoding a fusion polypeptide capable of binding a cytokine to form a nonfunctional complex comprising a nucleotide sequence encoding a first fusion polypeptide component comprising the amino acid sequence of a first scFv that binds to a site on the cytokine; a nucleotide sequence encoding a second fusion polypeptide component comprising the amino acid sequence a second scFv that binds to a site on the cytokine different from the site at which the first scFv binds; and a nucleotide sequence encoding a third fusion polypeptide component comprising the amino acid sequence of a multimerizing component.

In all of the above described embodiments comprising scFv's, the invention also contemplates embodiments in which the nucleotide sequence encoding the first component is upstream of the nucleotide sequence encoding the second component; embodiments in which the nucleotide sequence encoding the first component is downstream of the nucleotide sequence encoding the second component; and further embodiments of the invention in which the order of the first, second and third fusion polypeptide components is rearranged. For example, if the nucleotide sequence encoding the first component is designated 1, the nucleotide sequence encoding the second component is designated 2, and the nucleotide sequence of the third component is designated 3, then the order of the components in the isolated nucleic acid of the invention as read from 5' to 3' may be any of the following six combinations: 1,2,3; 1,3,2; 2,1,3; 2,3,1; 3,1,2; or 3,2,1.

In preferred embodiments of the invention, the multimerizing component comprises an immunoglobulin derived domain. More specifically, the immunoglobulin derived domain may be selected from the group consisting of the Fc domain of IgG, the heavy chain of IgG, and the light chain of IgG. In another embodiment, the multimerizing component may be an Fc domain from which the first five amino acids (including a cysteine) have been removed to produce a multimerizing component referred to as Fc(ΔC1). Alternatively, the multimerizing component may be an Fc domain in which a cysteine within the first five amino acids has been substituted for by another amino acid such as, for example, serine or alanine.

The present invention also provides for fusion polypeptides encoded by the isolated nucleic acid molecules of the invention. Preferably, the fusion polypeptides are in multimeric form, due to the function of the third multimerizing component. In a preferred embodiment, the multimer is a dimer. Suitable multimerizing components are sequences encoding an immunoglobulin heavy chain hinge region (Takahashi et al., 1982, Cell 29:671–679); immunoglobulin gene sequences, and portions thereof. In a preferred embodiment of the invention, immunoglobulin gene sequences, especially one encoding the Fc domain, are used to encode the third multimerizing component.

The present invention also contemplates a vector which comprises the nucleic acid molecule of the invention as described herein.

Also provided is an expression vector comprising a nucleic acid molecule of the invention as described herein, wherein the nucleic acid molecule is operatively linked to an expression control sequence. Also provided is a host-vector system for the production of a fusion polypeptide which comprises the expression vector of the invention which has been introduced into a host cell suitable for expression of the fusion polypeptide. The suitable host cell may be a bacterial cell such as *E. coli,* a yeast cell, such as *Pichia pastoris,* an insect cell, such as *Spodoptera frugiperda,* or a mammalian cell, such as a COS, CHO, 293, BHK or NS0 cell.

The present invention also provides for methods of producing the fusion polypeptides of the invention by growing cells of the host-vector systems described herein, under conditions permitting production of the fusion polypeptide and recovering the fusion polypeptide so produced.

The present invention provides novel antagonists which are based on receptor components that are shared by cytokines such as the CNTF family of cytokines.

The invention described herein contemplates the production of antagonists to any cytokine that utilizes an α specificity determining component which, when combined with the cytokine, binds to a first β signal transducing component to form a nonfunctional intermediate which then binds to a second β signal transducing component causing β-receptor dimerization and consequent signal transduction. According to the invention, the soluble α specificity determining component of the receptor (sRα) and the extracellular domain of the first β signal transducing component of the cytokine receptor (β1) are combined to form heterodimers (sRα:β1) that act as antagonists to the cytokine by binding the cytokine to form a nonfunctional complex.

As described in Example 1, CNTF and IL-6 share the β1 receptor component gp130. The fact that CNTF forms an intermediate with CNTFRα and gp130 can be demonstrated (Example 1) in cells lacking LIFRβ, where the complex of CNTF and CNTFRα binds gp130, and prevents homodimerization of gp130 by IL-6 and IL-6Rα, thereby blocking signal transduction. These studies provide the basis for the development of the IL-6 antagonists described herein, as they show that if, in the presence of a ligand, a nonfunctional intermediate complex, consisting of the ligand, its α receptor component and its β1 receptor component, can be formed, it will effectively block the action of the ligand. Other cytokines may use other β1 receptor components, such as LIFRβ, which may also be used to produce antagonists according to the present invention.

Thus for example, in one embodiment of the invention, effective antagonists of IL-6 or CNTF consist of heterodimers of the extracellular domains of the α specificity determining components of their receptors (sIL-6Rα and sCNTFRα respectively) and the extracellular domain of gp130. The resultant heterodimers, which are referred to hereinafter as sIL-6Rα:β1 and sCNTFRα:β1 respectively, function as high-affinity traps for IL-6 or CNTF, respectively, thus rendering the cytokine inaccessible to form a signal transducing complex with the native membrane-bound forms of their receptors.

Although soluble ligand binding domains from the extracellular portion of receptors have proven to be somewhat effective as traps for their ligands and thus act as antagonists [Bargetzi, et al., Cancer Res. 53:4010–4013 (1993); , et al., Proc. Natl. Acad. Sci. USA 89: 8616–8620 (1992); Mohler, et al., J. Immunol. 151: 1548–1561 (1993); Narazaki, et al., Blood 82: 1120–1126 (1993)], the IL-6 and CNTF receptors are unusual in that the α receptor components constitute ligand binding domains that, in concert with their ligands, function effectively in soluble form as receptor agonists [Davis, et al. Science 259:1736–1739 (1993); Taga, et al., Cell 58: 573–581 (1989)]. The sRα:β1 heterodimers prepared according to the present invention provide effective traps for their ligands, binding these ligands with affinities in the picomolar range (based on binding studies for CNTF to PC12D cells) without creating functional intermediates. The technology described herein may be applied to develop a cytokine trap for any cytokine that utilizes an α-component that confers specificity, as well as a β component which, when bound to the α-specificity component, has a higher affinity for the cytokine than either component alone. Accordingly, antagonists according to the invention include antagonists of interleukins 1 through 5 [IL-1, Greenfeder, et al. J. Biol. Chem. 270:13757–13765 (1995); Guo, et al. J. Biol. Chem. 270:27562–27568 (1995)], IL-2; [Taniguchi, et al. European Patent Nos. 0386289-A and 0386304-A (1990); Takeshita, et al. Science 257:379–382 (1992)]; IL-3; [Kitamura, et al. Cell 66:1165–1174 (1991)], IL-4; [Idzerda, et al. J. Exp. Med. 171:861–873 (1990)], IL-5; [Taverneir, et al. Cell 66:1175–1184 (1991)], IL-11 [(Cherel, et al. Direct Submission to EMBL/GenBank/DDBJ databases; accession No. Z38102)], interleukin 15 [IL-15; Hemar, et al. J. Cell Biol. 1295:55–64 (1995); Taniguchi, et al. European Patent Nos. 0386289-A and 0386304-A (1990); Takeshita, et al. Science 257:379–382 (1992)], granulocyte-macrophage colony stimulating factor [GM-CSF; Hayashida, et al. Proc. Natl. Acad. Sci. U.S.A. 97:9655–9659 (1990)], LIF, gamma interferon [IFNγ; Aguet, et al. Cell 55:273–280 (1988); Soh, et al. Cell 76:793–802 (1994)], and transforming growth factor beta [TGFβ; Inagaki, et al. Proc. Natl. Acad. Sci. USA 90:5359–5363 (1993)].

The α and β receptor extracellular domains may be prepared using methods known to those skilled in the art. The CNTFRα receptor has been cloned, sequenced and expressed [Davis, et al. (1991) Science 253:59–63 which is incorporated by reference in its entirety herein]. The cloning of LIFRβ and gp130 are described in Gearing et al. in EMBO J. 10:2839–2848 (1991), Hibi, et al. Cell 63:1149–1157 (1990) and in published PCT application WO 93/10151 published May 27, 1993, all of which are incorporated by reference in their entirety herein.

The receptor molecules useful for practicing the present invention may be prepared by cloning and expression in a prokaryotic or eukaryotic expression system. The recombinant receptor gene may be expressed and purified utilizing any number of methods. The gene encoding the factor may be subcloned into a bacterial expression vector, such as for example, but not by way of limitation, pCP110.

The recombinant factors may be purified by any technique which allows for the subsequent formation of a stable, biologically active protein. For example, and not by way of limitation, the factors may be recovered from cells either as soluble proteins or as inclusion bodies, from which they may be extracted quantitatively by 8M guanidinium hydrochloride and dialysis. In order to further purify the factors, conventional ion exchange chromatography, hydrophobic interaction chromatography, reverse phase chromatography or gel filtration may be used.

The sRα:β heterodimeric receptors may be engineered using known fusion regions, as described in published PCT application WO 93/10151 published May 27, 1993 entitled "Receptor for Oncostatin M and Leukemia Inhibitory Factor" which describes production of β receptor heterodimers, or they may be prepared by crosslinking of extracellular domains by chemical means. The domains utilized may consist of the entire extracellular domain of the α and β components, or they may consist of mutants or fragments thereof that maintain the ability to form a complex with its ligand and other components in the sRα:β1 complex. For example, as described below in example 4, IL-6 antagonists have been prepared using gp130 that is lacking its three fibronectin-like domains.

In one embodiment of the invention, the extracellular domains are engineered using leucine zippers. The leucine zipper domains of the human transcription factors c-jun and c-fos have been shown to form stable heterodimers [Busch and Sassone-Corsi, Trends Genetics 6: 36–40 (1990); Gentz, et al., Science 243: 1695–1699 (1989)] with a 1:1 stoichiometry. Although jun-jun homodimers have also been shown to form, they are about 1000-fold less stable than jun-fos heterodimers. Fos-fos homodimers have not been detected.

The leucine zipper domain of either c-jun or c-fos are fused in frame at the C-terminus of the soluble or extracellular domains of the above mentioned receptor components by genetically engineering chimeric genes. The fusions may be direct or they may employ a flexible linker domain, such as the hinge region of human IgG, or polypeptide linkers consisting of small amino acids such as glycine, serine, threonine or alanine, at various lengths and combinations. Additionally, the chimeric proteins may be tagged by His-His-His-His-His-His (His6),[SEQ. ID NO. 1] to allow rapid purification by metal-chelate chromatography, and/or by epitopes to which antibodies are available, to allow for detection on western blots, immunoprecipitation, or activity depletion/blocking in bioassays.

In another embodiment, as described below in Example 3. the sRα:β1 heterodimer is prepared using a similar method, but using the Fc-domain of human IgG1 [Aruffo, et al., Cell 67:35–44 (1991)]. In contrast to the latter, formation of heterodimers must be biochemically achieved, as chimeric molecules carrying the Fc-domain will be expressed as disulfide-linked homodimers. Thus, homodimers may be reduced under conditions that favor the disruption of interchain disulfides but do not effect intra-chain disulfides. Then monomers with different extracellular portions are mixed in equimolar amounts and oxidized to form a mixture of homo- and heterodimers. The components of this mixture are separated by chromatographic techniques. Alternatively, the formation of this type of heterodimers may be biased by genetically engineering and expressing molecules that consist of the soluble or extracellular portion of the receptor components followed by the Fc-domain of hIgG, followed by either the c-jun or the c-fos leucine zippers described above [Kostelny, et al., J. Immunol. 148: 1547–1553 (1992)]. Since these leucine zippers form predominately heterodimers, they may be used to drive formation of the heterodimers where desired. As for the chimeric proteins described using leucine zippers, these may also be tagged with metal chelates or an epitope. This tagged domain can be used for rapid purification by metal-chelate chromatography, and/or by antibodies, to allow for detection on western blots, immunoprecipitation, or activity depletion/blocking in bioassays.

In additional embodiments, heterodimers may be prepared using other immunoglobulin derived domains that drive the formation of dimers. Such domains include, for example, the heavy chains of IgG (Cγ1 and Cγ4), as well as the constant regions of kappa (κ) and lambda (λ) light chains of human immunoglobulins. The heterodimerization of Cγ with the light chain occurs between the CH1 domain of Cγ and the constant region of the light chain (CL),and is stabilized by covalent linking of the two domains via a single disulfide bridge. Accordingly, as described in Example 4, constructs may be prepared using these immunoglobulin domains. Alternatively, the immunoglobulin domains include domains that may be derived from T cell receptor components which drive dimerization, In another embodiment of the invention the sRα:β1 heterodimers are prepared by expression as chimeric molecules utilizing flexible linker loops. A DNA construct encoding the chimeric protein is designed such that it expresses two soluble or extracellular domains fused together in tandem ("head to head") by a flexible loop. This loop may be entirely artificial (e.g. polyglycine repeats interrupted by serine or threonine at a certain interval) or "borrowed" from naturally occurring proteins (e.g. the hinge region of hIgG). Molecules may be engineered in which the order of the soluble or extracellular domains fused is switched (e.g. sIL6Rα/loop/sgp130 or sgp130/loop/sIL-6Rα) and/or in which the length and composition of the loop is varied, to allow for selection of molecules with desired characteristics.

Alternatively, the heterodimers made according to the present invention may be purified from cell lines cotransfected with the appropriate α and β components. Heterodimers may be separated from homodimers using methods available to those skilled in the art. For example, limited quantities of heterodimers may be recovered by passive elution from preparative, nondenaturing polyacrylamide gels. Alternatively, heterodimers may be purified using high pressure cation exchange chromatography. Excellent purification has been obtained using a Mono S cation exchange column.

In addition to sRα:β1 heterodimers that act as antagonists by binding free CNTF or IL-6, the present invention also contemplates the use of engineered, mutated versions of IL-6 with novel properties that allow it to bind to IL-6Rα and a single gp130 molecule, but fail to engage the second gp130 to complete β component homodimerization, and thus act as an effective IL-6 antagonist on any IL-6 responsive cell. Our model for the structure of the IL-6 and CNTF receptor complexes indicates that these cytokines have distinct sites for binding the α, β1, and β2 receptor components [Stahl and Yancopoulos, Cell 74: 587–590 (1993)]. Mutations of critical amino acid residues comprising each of these sites gives rise to novel molecules which have the desired antagonistic properties. Ablation of the β1 site would give a molecule which could still bind to the α receptor component but not the β1 component, and thereby comprise an antagonist with nanomolar affinity. Mutations of critical amino acid residues comprising the β2 site of IL-6 (IL-6β2$^-$) would give a molecule that would bind to IL-6Rα and the first gp130 monomer, but fail to engage the second gp130 and thus be functionally inactive. Similarly, mutations of the CNTF β2 site would give a molecule (CNTFβ2$^-$) that would bind CNTFRα and gp130, but fail to engage LIFRβ, thereby antagonizing CNTF action by forming the non-functional β1 intermediate. Based on the binding results described above where CNTF forms the β1 intermediate with high affinity, both CNTFβ2$^-$ and IL-6β2$^-$ would constitute antagonists with affinity in the range of 10 pM.

A variety of means are used to generate and identify mutations of IL-6 or CNTF that have the desired properties. Random mutagenesis by standard methods of the DNA encoding IL-6 or CNTF may be used, followed by analysis of the collection of products to identify mutated cytokines having the desired novel properties as outlined below. Mutagenesis by genetic engineering has been used extensively in order to elucidate the structural organization of functional domains of recombinant proteins. Several different approaches have been described in the literature for carrying out deletion or substitution mutagenesis. The most successful appear to be alanine scanning mutagenesis [Cunningham and Wells (1989), Science 244: 1081–1085] and homolog-scanning mutagenesis [Cunningham, et al., (1989), Science 243:1330–1336].

Targeted mutagenesis of the IL-6 or CNTF nucleic acid sequences using such methods can be used to generate CNTFβ2- or IL-6β2-candidates. The choice of regions appropriate for targeted mutagenesis is done systematically, or determined from studies whereby panels of monoclonal antibodies against each factor are used to map regions of the cytokine that might be exposed after binding of the cytokine to the α receptor component alone, or to the αβ1 heterodimeric soluble receptors described above. Similarly, chemical modification or limited proteolysis of the cytokine alone or in a complex bound to the α receptor component or the αβ1 heterodimeric soluble receptors described above, followed by analysis of the protected and exposed regions could reveal potential β2 binding sites.

Assays for identifying CNTF or IL-6 mutants with the desired properties involve the ability to block with high affinity the action of IL-6 or CNTF on appropriately responsive cell lines [Davis, et al., Science 259: 1736–1739 (1993); Murakami, et al., Proc. Natl. Acad. Sci. USA 88: 11349–11353 (1991)]. Such assays include cell proliferation, survival, or DNA synthesis driven by CNTF or IL-6, or the construction of cell lines where binding of factor induces production of reporters such as CAT or β-galactosidase [Savino, et al., Proc. Natl. Acad. Sci. USA 90: 4067–4071 (1993)].

Alternatively, the properties of various mutants may be assessed with a receptor-based assay. One such assay consists of screening mutants for their ability to bind the sRα:β1 receptor heterodimers described above using epitope-tagged [Davis et al., Science 253: 59–63 (1991)] sRα:β1 reagents. Furthermore, one can probe for the presence or absence of the β2 site by assessing whether an epitope-tagged soluble β2 reagent will bind to the cytokine in the presence of the β1 heterodimer. For example, CNTF only binds to LIFRβ (the β2 component) in the presence of both CNTFRα and gp130 [Davis, et al. Science 260: 1805–1808 (1993); Stahl, et al. J. Biol. Chem. 268: 7628–7631 (1993)]. Thus a soluble LIFRβ reagent would only bind to CNTF in the presence of the soluble sRα:β1 dimer sCNTFRα:β1. For IL-6, the sRα:β1 reagent would be IL-6Rα:β1 and the probe for the β2 site would be epitope-tagged sgp130. Thus β2⁻ mutants of CNTF would be identified as those that bound the sRα:β1 reagent, demonstrating that the α and β1 site of the cytokine were intact, yet failed to bind the β2 reagent.

In addition, the present invention provides for methods of detecting or measuring the activity of potential β2⁻ mutants by measuring the phosphorylation of a β-preceptor component or a signal transduction component selected from the group consisting of Jak1, Jak2 and Tyk2 or any other signal transduction component, such as the CLIPs, that are determined to be phosphorylated in response to a member of the CNTF family of cytokines.

A cell that expresses the signal transduction component(s) described herein may either do so naturally or be genetically engineered to do so. For example, Jak1 and Tyk-2-encoding nucleic acid sequences obtained as described in Velazquez, et al., Cell, Vol. 70:313–322 (1992), may be introduced into a cell by transduction, transfection, microinjection, electroporation, via a transgenic animal, etc., using any known method known in the art.

According to the invention, cells are exposed to a potential antagonist and the tyrosine phosphorylation of either the β-component(s) or the signal transduction component(s) are compared to the tyrosine phosphorylation of the same component(s) in the absence of the potential antagonist.

In another embodiment of the invention, the tyrosine phosphorylation that results from contacting the above cells with the potential antagonist is compared to the tyrosine phosphorylation of the same cells exposed to the parental CNTF family member. In such assays, the cell must either express the extracellular receptor (α-component) or the cells may be exposed to the test agent in the presence of the soluble receptor component. Thus, for example, in an assay system designed to identify agonists or antagonists of CNTF, the cell may express the α-component CNTFRα, the β-components gp130 and LIFRβ and a signal transducing component such as Jak1. The cell is exposed to test agents, and the tyrosine phosphorylation of either the β-components or the signal transducing component is compared to the phosphorylation pattern produced in the presence of CNTF. Alternatively, the tyrosine phosphorylation which results from exposure to a test agent is compared to the phosphorylation which occurs in the absence of the test agent. Alternatively, an assay system, for example, for IL-6 may involve exposing a cell that expresses the β-component gp130 and a signal transducing protein such as Jak1, Jak2 or Tyk2 to a test agent in conjunction with the soluble IL-6 receptor.

In another embodiment of the invention the above approaches are used to develop a method for screening for small molecule antagonists that act at various steps in the process of ligand binding, receptor complex formation, and subsequent signal transduction. Molecules that potentially interfere with ligand-receptor interactions are screened by assessing interference of complex formation between the soluble receptors and ligand as described above. Alternatively, cell-based assays in which IL-6 or CNTF induce response of a reporter gene are screened against libraries of small molecules or natural products to identify potential antagonists. Those molecules showing antagonist activity are rescreened on cell-based assays responding to other factors (such as GM-CSF or factors like Neurotrophin-3 that activate receptor tyrosine kinases) to evaluate their specificity against the CNTF/IL-6/OSM/LIF family of factors. Such cell-based screens are used to identify antagonists that inhibit any of numerous targets in the signal transduction process.

In one such assay system, the specific target for antagonists is the interaction of the Jak/Tyk family of kinases [Firmbach-Kraft, Oncogene 5: 1329–1336 (1990); Wilks, et al., Mol. Cell. Biol. 11:2057–2065 (1991)] with the receptor β subunits. As described above, LIFRβ and gp130 preassociate with members of the Jak/Tyk family of cytoplasmic protein tyrosine kinases, which become activated in response to ligand-induced β component dimerization Stahl, et al. Science 263:92–95 (1993). Thus small molecules that could enter the cell cytoplasm and disrupt the interaction between the β component and the Jak/Tyk kinase could potentially block all subsequent intracellular signaling. Such activity could be screened with an in vitro scheme that assessed the ability of small molecules to block the interaction between the relevant binding domains of purified β component and Jak/Tyk kinase. Alternatively, one could easily screen for molecules that could inhibit a yeast-based assay of β component binding to Jak/Tyk kinases using the two-hybrid interaction system [Chien, et al., Proc. Natl. Acad. Sci. 88: 9578–9582 (1991)]. In such a system, the interaction between two proteins (β component and Jak/Tyk kinase or relevant domains thereof in this example) induces production of a convenient marker such as β-galactosidase. Collections of small molecules are tested for their ability to disrupt the desired interaction without inhibiting the interaction between two control proteins. The advantage of this screen would be the requirement that the test compounds enter the cell before inhibiting the interaction between the β component and the Jak/Tyk kinase.

The CNTF family antagonists described herein either bind to, or compete with the cytokines CNTF and IL-6. Accordingly, they are useful for treating diseases or disorders mediated by CNTF or IL-6. For example, therapeutic uses of IL-6 antagonists would include the following:

1) In osteoporosis, which can be exacerbated by lowering of estrogen levels in post-menopausal women or through ovariectomy, IL-6 appears to be a critical mediator of osteoclastogenesis, leading to bone resorption [Horowitz, Science 260: 626–627 (1993); Jilka, et al., Science 257: 88–91 (1992)]. Importantly, IL-6 only appears to play a major role in the estrogen-depleted state, and apparently is minimally involved in normal bone maintenance. Consistent with this, experimental evidence indicates that function-blocking antibodies to IL-6 can reduce the number of osteoclasts [Jilka, et al. Science 257: 88–91 (1992)]. While estrogen replacement therapy is also used, there appear to be side effects that may include increased risk of endometrial and breast cancer. Thus, IL-6 antagonists as described herein would be more specific to reduce osteoclastogenesis to normal levels.

2) IL-6 appears to be directly involved in multiple myeloma by acting in either an autocrine or paracrine fashion to promote tumor formation [van Oers, et al., Ann Hematol. 66: 219–223 (1993)]. Furthermore, the elevated IL-6 levels create undesirable secondary effects such as bone resorption, hypercalcemia, and cachexia; in limited studies function-blocking antibodies to IL-6 or IL-6Ra have some efficacy [Klein, et al., Blood 78: 1198–1204 (1991); Suzuki, et al., Eur. J. Immunol. 22:1989–1993 (1992)]. Therefore, IL-6 antagonists as described herein would be beneficial for both the secondary effects as well as for inhibiting tumor growth.

3) IL-6 may be a mediator of tumor necrosis factor (TNF) that leads to cachexia associated with AIDS and cancer [Strassmann, et al., J. Clin. Invest. 89: 1681–1684 (1992)], perhaps by reducing lipoprotein lipase activity in adipose tissue [Greenberg, et al., Cancer Research 52: 4113–4116 (1992)]. Accordingly, antagonists described herein would be useful in alleviating or reducing cachexia in such patients.

Effective doses useful for treating these or other CNTF family related diseases or disorders may be determined using methods known to one skilled in the art [see, for example, Fingl, et al., The Pharmacological Basis of Therapeutics, Goodman and Gilman, eds. Macmillan Publishing Co., New York, pp. 1–46 ((1975)]. Pharmaceutical compositions for use according to the invention include the antagonists described above in a pharmacologically acceptable liquid, solid or semi-solid carrier, linked to a carrier or targeting molecule (e.g., antibody, hormone, growth factor, etc.) and/or incorporated into liposomes, microcapsules, and controlled release preparation (including antagonist expressing cells) prior to administration in vivo. For example, the pharmaceutical composition may comprise one or more of the antagonists in an aqueous solution, such as sterile water, saline, phosphate buffer or dextrose solution. Alternatively, the active agents may be comprised in a solid (e.g. wax) or semi-solid (e.g. gelatinous) formulation that may be implanted into a patient in need of such treatment. The administration route may be any mode of administration known in the art, including but not limited to intravenously, intrathecally, subcutaneously, by injection into involved tissue, intraarterially, intranasally, orally, or via an implanted device.

Administration may result in the distribution of the active agent of the invention throughout the body or in a localized area. For example, in some conditions which involve distant regions of the nervous system, intravenous or intrathecal administration of agent may be desirable. In some situations, an implant containing active agent may be placed in or near the lesioned area. Suitable implants include, but are not limited to, gelfoam, wax, or microparticle-based implants.

EXAMPLE 1
CNTF Competes with IL-6 for Binding to GP130

MATERIALS AND METHODS

Materials. A clone of PC12 cells that respond to IL-6 (PC12D) was obtained from DNAX. Rat CNTF was prepared as described [Masiakowski, et al., J. Neurochem. 57:1003–10012 (1991)]. IL-6 and sIL-6Rα were purchased from R & D Systems. Antisera was raised in rabbits against a peptide derived from a region near the C-terminus of gp130 (sequence: CGTEGQVERFETVGME) [SEQ. ID. NO. 2] by the method described (Stahl, et al. J. Biol. Chem. 268:7628–7631 (1993). Anti-phosphotyrosine monoclonal 4G10 was purchased from UBI, and reagents for ECL from Amersham.

Signal Transduction Assays. Plates (10 cm) of PC12D were starved in serum-free medium (RPMI 1640+ glutamine) for 1 hour, then incubated with IL-6 (50 ng/mL)+ sIL-6R (1 mg/mL) in the presence or absence of added rat CNTF at the indicated concentrations for 5 minutes at 37° C. Samples were then subjected to anti-gp130 immunoprecipitation, SDS PAGE, and anti-phosphotyrosine immunoblotting as described (Stahl, et al. J. Biol. Chem. 268:7628–7631 (1993).

RESULTS

Figure 2:
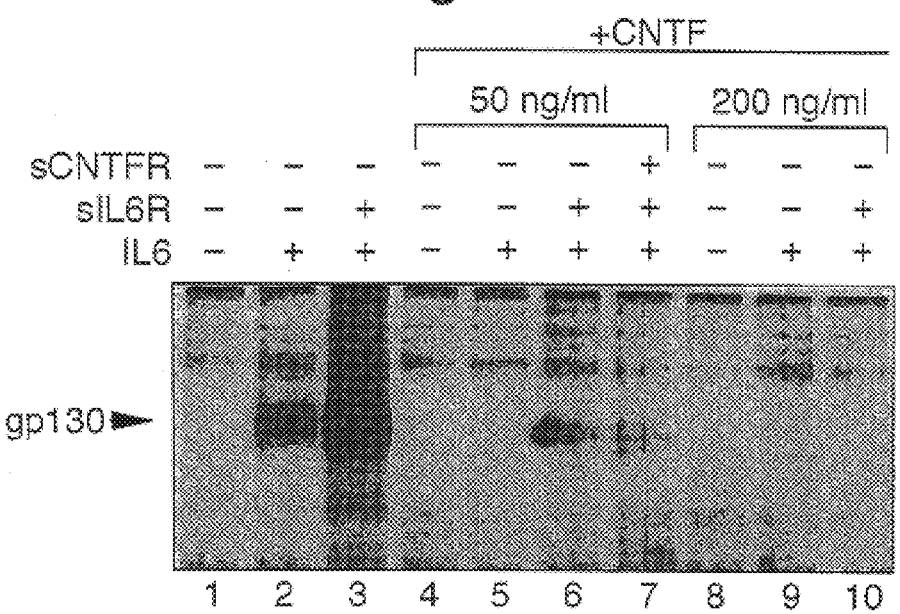
FIG. 2: CNTF inhibits IL-6 responses in a PC12 cell line (called PC12D) that expresses IL6Rα, gp130, CNTFRα, but not LIFRβ. Serum-deprived PC12D cells were incubated +IL-6 (50 ng/mL) in the presence or absence of CNTF as indicated. Some plates also received soluble IL6Rα (1 mg/mL) or soluble CNTFRα (1 mg/mL) as indicated. Cell lysates were subjected to immunoprecipitation with anti-gp130 and immunoblotted with anti-phosphotyrosine. Tyrosine phosphorylation of gp130 is indicative of IL-6 induced activation of the IL-6 receptor system, which is blocked upon coaddition of CNTF.

The ability of CNTF to block IL-6 responses was measured using a PC12 cell line (called PC12D) that expresses IL-6Ra, gp130, and CNTFRα, but not LIFRβ. As one would predict, these cells respond to IL-6, but not to CNTF (FIG. 2) since LIFRβ is a required component for CNTF signal transduction [Davis, et al., Science 260: 59–63 (1993)]. In accordance with results on other cell lines [Ip, et al., Cell 69: 1121–1132 (1992)], PC12D cells give tyrosine phosphorylation of gp130 (as well as a variety of other proteins called CLIPs) in response to 2 nM IL-6 (FIG. 2). Addition of recombinant soluble IL-6Rα (sIL-6Rα) enhances the level of gp130 tyrosine phosphorylation, as has been reported in some other systems [(Taga, et al., Cell 58: 573–581 (1989)]. However, addition of 2 nM CNTF simultaneously with IL-6 severely diminishes the tyrosine phosphorylation of gp130. Although a slight gp130 phosphorylation response remains in the presence of CNTF, IL-6, and sIL-6Rα, it is eliminated if the CNTF concentration is increased fourfold to 8 nM. Thus, in IL-6 responsive cells that contain CNTFRα but no LIFRβ, CNTF is a rather potent antagonist of IL-6 action.

EXAMPLE 2
Binding of CNTF to the CNTFRα:β

MATERIALS AND METHODS

Scatchard Analysis of CNTF Binding. $^{125}$1-CNTF was prepared and purified as described [Stahl et al. JBC 268: 7628–7631 (1993)]. Saturation binding studies were carried out in PC12 cells, using concentrations of $^{125}$1-CNTF ranging from 20 pM to 10 nM. Binding was performed directly on a monolayer of cells. Medium was removed from wells and cells were washed once with assay buffer consisting of phosphate buffered saline (PBS; pH 7.4), 0. mM bacitracin, 1 mM PMSF, 1 mg/ml leupeptin, and 1 mg/ml BSA. Cells were incubated in $^{125}$1-CNTF for 2 hours at room temperature, followed by 2 quick washes with assay buffer. Cells were lysed with PBS containing 1% SDS and counted in a Packard Gamma Counter at 90–95% efficiency. Non-specific binding was defined by the presence of 100-fold excess of unlabelled CNTF. Specific binding ranged from 70% to 95%.

RESULTS

Figure 3:
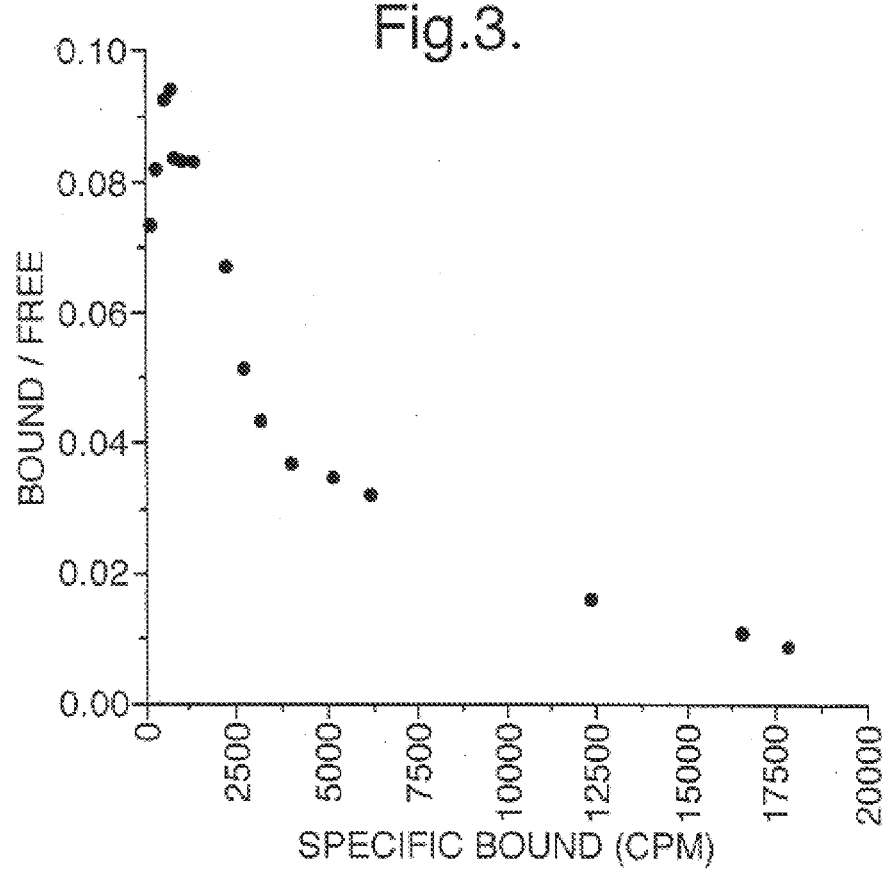
FIG. 3: Scatchard analysis of iodinated CNTF binding on PC12D cells. PC12D cells were incubated with various concentrations of iodinated CNTF in the presence or absence of excess non-radioactive competitor to determine the specific binding. The figure shows a Scatchard plot of the amount of iodinated CNTF specifically bound, and gives data consistent with two binding sites with dissociation constants of 9 pM and 3.4 nM.

The equilibrium constant for binding of CNTF to CNTFRα:β1 was estimated from Scatchard analysis of iodinated CNTF binding on PC12D cells (FIG. 3). The data is consistent with a 2 site fit having dissociation constants of 9 pM and 3.4 nM. The low affinity site corresponds to interaction of CNTF with CNTFRα, which has a Kd near 3 nM [(Panayotatos, et al., J. Biol. Chem. 268: 19000–19003 (1993)]. We interpret the high affinity complex as the intermediate containing CNTF, CNTFRα, and gp130. A Ewing sarcoma cell line (EW-1) which does contain CNTFRα, gp130, and LIFRβ, and therefore gives robust tyrosine phosphorylation in response to CNTF, displays a very similar two site fit with dissociation constants of 1 nM and 10 pM (Wong, et al., unpublished data). Thus it is apparent that CNTF binds with equally high affinity to a complex containing only CNTFRα and gp130, as it does to a complex which additionally contains LIFRβ, thus demonstrating the feasibility of creating the sRα:β antagonists described herein.

EXAMPLE 3
Methods of Producing Cyctokine Ligand Traps

Virus Stock Production

SF21 insect cells obtained from Spodoptera frugiperda were grown at 27C in Gibco SF900 II medium to a density of 1×10$^6$ cells/mL. The individual virus stock for either GP130-Fc-His$_6$ (FIGS. 4A–4B [SEQ ID NO: 7]) or IL6Ra-Fc (FIG. 5 [SEQ ID NO: 8]) was added to the bioreactor to a low multiplicity 0.01–0.1 PFU/cell to begin the infection. The infection process was allowed to continue for 5–7 days allowing maximum virus replication without incurring substantial cell lysis. The cell suspension was aseptically aliquoted into sterile centrifuge bottles and the cells removed by centrifugation. The cell-free supernatant was collected in sterile bottles and stored at 4 C. until further use.

The virus titer was determined by plaque assay as described by O'Reilly, Miller and Luckow. The method is carried out in 60 mm tissue-culture dishes which are seeded with 2×10$^6$ cells. Serial dilutions of the virus stock are added to the attached cells and the mixture incubated with rocking to allow the virus to adsorb to individual cells. An agar overlay is added and plates incubated for 5–7 days at 27 C. Staining of viable cells with neutral red revealed circular plaques resulting which were counted to give the virus titer.

Coinfection of Cells for Protein Production

Uninfected SF21 Cells were grown in a 60 L ABEC bioreactor containing 40 L of SF900 II medium. Temperature was controlled at 27 C. and the dissolved oxygen level was maintained at 50% of saturation by controlling the flowrate of oxygen in the inlet gas stream. When a density of 2×10$^6$ cells/mL was reached, the cells were concentrated within the bioreactor to a volume of 20 L using a low shear steam sterilizable pump and a with tangential flow filtration device with Millipore Prostak 0.65 micron membranes. After concentration fresh sterile growth medium is slowly added to the bioreactor while the filtration system continues to remove the spent growth medium by diafiltration. After two volume exchanges (40 L) have been carried out an additional 20 L of fresh medium was added to the bioreactor to resuspend the cells to the original volume of 40 L. The cell density was determined once again by counting viable cells using a hemacytometer.

The required amount of each virus stock was calculated based on the cell density, virus titer and the desired multiplicity of infection (MOI). Virus stock ratios of 5:1, 5:2, 10:2 and 10:4, IL6Ra-Fc to GP130-Fc-His$_6$ all resulted in production of significant amounts of heterodimer. The ideal virus stock ratio is highly dependent on the ease of purification of the heterodimer from each of the two homodimers. The IL6Ra-Fc homodimer is relatively easy to remove downstream by immobilized metal affinity chromatography. Virus infection ratios have been chosen to minimize the formation of the GP130-Fc-His$_6$ homodimer which is more difficult to clear downstream. The relative amount of GP130-Fc-His$_6$ virus stock chosen for infection has increased with successive batches as the purification method for clearing the resultant homodimer has improved.

The virus stocks were aseptically mixed in a single vessel then transferred to the bioreactor. This results in synchronous infection of the SF21 cells. The infection is allowed to proceed for three to four days, allowing sufficient time for maximal production of the heterodimer protein.

Recovery and Protein A Chromatographic Purification

At the conclusion of the infection phase of the bioreactor process the cells were concentrated in the bioreactor using a 10 ft$^2$ Millipore Prostak filter (0.65 micron) pore size. The cell-free permeate passing through the filter was collected in a clean process vessel. At the conclusion of the filtration operation the pH of permeate stream, containing the protein product, was adjusted to 8.0 with 10N NaOH. The resultant precipitate was removed by forcing the extract through a 0.8 micron depth filter (Sartorious), followed by a 0.2 micron filter. Sufficient 0.5M EDTA stock was added to give a final concentration of 5 mM. The filtered protein solution was loaded onto a 10 cm diameter column containing 100–200 mL of Pharmacia Protein A Sepharose 4 Fast Flow, equilibrated with PBS. Protein A has a very high affinity for the Fc-Fc domain of each of the 3 recombinant protein products, allowing them to bind while other proteins in the cell-free extract flow through the column. After loading the column was washed to baseline with PBS containing an additional 350 mM NaCl. The IgG-Fc tagged proteins were eluted at low pH, either with 0.5M acetic acid or with a decreasing pH gradient of 0.1M citric acid and 0.2M disodium phosphate buffers. Tris base or disodium phosphate was added to the eluted protein to avoid prolonged exposure to low pH conditions.

The pooled protein was diafiltered into PBS or HEPES buffer for subsequent and derivitized with 1 mM iodoacetamide to protect the exposed sulfhydryl group on the free cysteine near the hinge region of each Fc domain. This prevents disulfide mediated aggregation of proteins. A 6 ft2 Millipore spiral wound ultrafiltration membrane with nominal 30 kiloDalton cutoff was used to perform the buffer exchange. The total protein was determined by UV absorbance at 280 nm using the diafiltration buffer as a blank. The relative amounts of heterodimer and two homodimer proteins were determined by SDS PAGE gel electrophoresis using a 6% Tris-Glycine gel (Novex). Gels were Coomasie stained then transferred into destain solution overnight. A Shimadzu scanning densitometer was used to determine the relative intensity of the individual protein bands on the SDS PAGE gel. The peak area ratios are used to compute the fraction of heterodimer and each of the homodimers in the column pool fractions.

Immobilized Metal Affinity Chromatographic Purification

The six histidine residues on the C-terminus of the GP130-Fc-His$_6$ fusion protein provides a n excellent molecular handle for separation of the heterodimeric IL6 antagonist from the two homodimers. The imidazole group on each of the C-terminal histidines of the GP130-Fc-His$_6$ moiety has a strong binding constant with several divalent metals, including copper, nickel, zinc, cobalt, iron and calcium. Since the IL6Ra-Fc homodimer has no C-terminal histidine residues, it clearly has the lowest affinity. The IL6Ra-Fc-GP130-Fc-His$_6$ heterodimer has a single stand set six histidines giving it greater affinity for the metal, while the GP130-Fc-His$_6$ homodimer has two sets of six histidines each giving it the highest affinity of the three IgG tagged proteins to the metal affinity column. Selective elution of the three proteins with increasing amounts of imidazole in the elution buffer therefore elutes the proteins in the following order:

1. IL6Ra-Fc homodimer
2. IL6Ra-Fc-GP130-Fc-His heterodimer
3. GP130-Fc-His homodimer A 26 mm diameter column containing 100 mL of Pharmacia Chelating Sepharose Fast Flow was saturated with a solution of nickel sulfate until a significant green color is observed in the column eluate. The column is then washed with several column volumes of deionized water, then equilibrated with 50 mM HEPES, 40 mM imidazole, pH 8.0. The binding of imidazole to the immobilized nickel results in a green to blue color change. Imidazole was added to the protein load to a final concentration of 40 mM. Addition of imidazole to the protein load reduces the binding of IL6Ra-Fc homodimer, increasing the surface area available for the remaining two species. After loading, the column was washed with several column volumes of 50 mM HEPES, 80 mM imidazole, pH 8.0 until a steady baseline was reestablished. The heterodimer was selectively eluted with 50 mM HEPES, 150 mM imidazole, pH 8.0 over several column volumes. The protein fractions were pooled and diafiltered into PBS as described in the section above.

EXAMPLE 4

Alternative Methods of Constructing Ligand Traps

BACKGROUND

As described above, receptor activation by CNTF, and analogously by IL-6 and IL-11, follows an ordered sequence of binding events (FIG. 6). The cytokine initially binds to its cognate Rα with low affinity (Kd=3 to 10 nM); this is a required step—cells which do not express the cognate Rα do not respond to the cognate cytokine. The cytokine•Rα complex associates with the first signal transducing component, gp130, to form a high affinity complex (Kd in the order of 10 pM for the CNTF•CNTFRα•gp130 complex). This complex does not transduce signal, as it is the dimerization of the signal transducing components that brings about signaling (Stahl and Yancopoulos, J. Neurobiology 25: 1454–1466 (1994); Stahl et al., Science 267:1349–1353 (1995); Davis et al., Science 260:1805–1808 (1993); Stahl et al., Science 263:92–95 (1994); Murakami, et al. Science 260:1808–1810 (1993). At least in the case of IL-6, the cytokine•Rα•signal transducer heterotrimeric complex subsequently associates with another like complex, to form a hexameric complex (FIG. 6) (Ward et al., J. Biol. Chem. 269:23286–23289 (1994). The resulting dimerization of the signal transducers—gp130 in the case of IL-6 (Murakami et al., Science 260:1808–1810 (1993) and IL-11, gp130 and LIFR in the case of CNTF (Davis et al., Science 260:1805–1808 (1993)—brings about signal transduction.

The initial heterodimeric molecules made comprised a soluble Rα-component linked to the extracellular domain of gp130. These molecules were shown to mimic the high affinity cytokine•Rα•gp130 complex and behave as a high affinity antagonist of their cognate cytokine (FIG. 7). To make these molecules, the extracellular domain of gp130 was paired with the extracellular domain of the a-receptor components for IL-6 and CNTF, IL-6Rα and CNTFRα respectively. To link the Rα with the extracellular domain of gp130, the soluble Rα-components and gp130 were fused to the Fc portion of human IgG1 to produce Rα-Fc and gp130-Fc respectively. The Fc domain was chosen primarily but not solely because it naturally forms disulfide-linked dimers. Heterodimeric molecules comprising Rα-Fc•gp130-Fc were expressed, purified and shown to behave as highly potent antagonists of their cognate ligand. Furthermore, these molecules were found to be highly specific for their cognate cytokine since it is the choice of the α-receptor component which specifies which cytokine is bound and trapped (there is no measurable binding of the cytokine to gp130 in the absence of the appropriate Rα).

Here we describe an extension of this technology which allows the engineering of different heteromeric soluble receptor ligand traps which by virtue of their design may have additional beneficial characteristics such as stability, Fc-receptor-mediated clearance, or reduced effector functions (such as complement fixation). Furthermore, the technology described should prove suitable for the engineering of any heteromeric protein in mammalian or other suitable protein expression systems, including but not limited to heteromeric molecules which employ receptors, ligands, and catalytic components such as enzymes or catalytic antibodies.

MATERIALS AND METHODS

Genetic Engineering of heteromeric immunoglobulin heavy/light chain soluble receptor-based ligand traps for IL-6.

Figure 8:
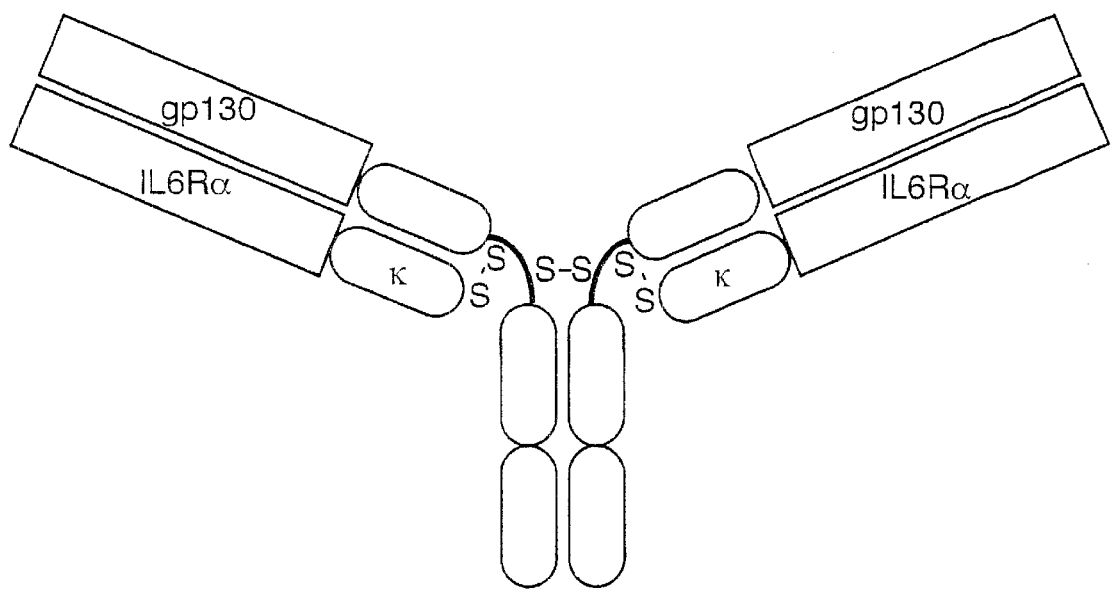
FIG. 8. Heteromeric immunoglobulin Heavy/Light Chain Receptor Fusions. An example of a heavy/light chain receptor fusion molecule is schematically depicted. The extracellular domain of gp130 is fused to Cγ, whereas the extracellular domain of IL-6Rα is fused to the constant region of the kappa chain (κ). The inter-chain disulfide bridges are also depicted (S-S).

The IL-6 traps described here were engineered using human gp130, human IL-6 α-receptor (IL-6Rα), the constant region of the heavy chains (Cγ) of human IgG1 (Cγ1) (Lewis et al., Journal of Immunology 151:2829–2838 (1993) or IgG4 (Cγ4) with or without a join-region (J), and the constant regions of kappa (κ) and lambda (λ) (Cheung, et al., Journal of Virology 66:6714–6720 (1992) light chains of human immunoglobulin (Ig), also with or without a different j-peptide (j). This design takes advantage of the natural ability of the Cγ domain to heterodimerize with κ or λ light chains. The heterodimerization of Cγ with the light chain occurs between the CH1 domain of Cγ and the constant region of the light chain ($C_L$), and is stabilized by covalent linking of the two domains via a single disulfide bridge. We reasoned that, like the Fc domain of human IgG1, the combination of Cγ with $C_L$ could be used to produce disulfide linked heteromeric proteins comprised of the extracellular domain of gp130 on one chain and the extracellular domain of IL-6Rα on the other chain. Like their Fc-based counterparts, such proteins were postulated to be high affinity ligand traps for IL-6 and as a result to inhibit the interaction of IL-6 with the native receptor on IL-6-responsive cells, thus functioning as IL-6 antagonists. Furthermore, constructs employing the full length Cγ region would, much like antibodies, form homodimers of the Cγ chain, giving rise to antibody-like molecules comprising of two "light chains" and two "heavy chains" (FIG. 8). The potential advantage of this design is that it may more closely mimic the IL-6•IL-6Rα•gp130 complex and may display a higher affinity for the ligand than comparable single heterodimers. An additional design is incorporated by using truncated versions of Cγ, comprised only of the $C_H1$ domain. These will form heterodimeric molecules with receptor-κ fusion proteins, and will thus resemble the Fab fragment of antibodies.

All the soluble receptor-Ig chimeric genes may be engineered in plasmid vectors including, but not limited to, vectors suitable for mammalian expression (Cos monkey kidney cells, Chinese Hamster Ovary cells [CHO], and ras-transformed fibroblasts [MG-ras]) and include a Kozak sequence (CGC CGC CAC CAT GGT G [SEQ ID NO: 3]) at the beginning of each chimeric gene for efficient translation. Engineering was performed using standard genetic engineering methodology. Each construct was verified by DNA sequencing, mammalian expression followed by western blotting with suitable antibodies, biophysical assays that determine ligand binding and dissociation, and by growth inhibition assays (XG-1, as described later). Since the domains utilized to engineer these chimeric proteins are flanked by appropriate restriction sites, it is possible to use these domains to engineer other chimeric proteins, including chimeras employing the extracellular domains of the receptors for factors such as IL-1, IL-2, IL-3, IL-4, IL-5, GM-CSF, LIF, IL-11, IL-15, IFNγ, TGFβ, and others. The amino acid coordinates for each component utilized in making the IL-6 traps are listed below (Note: numbering starts with the initiating methionine as #1; long sequences are listed using the single letter code for the twenty amino acids):

(a) Constructs Employing Human gp130
(i) gp130-Cγ1 was engineered by fusing in frame the extracellular domain of gp130 (amino acids 1 to 619) to a Ser-Gly bridge, followed by the 330 amino acids which comprise Cγ1 and a termination codon (FIGS. 9A and 9B [SEQ ID NO: 9]).

(ii) gp130-J-Cγ1 was engineered in the same manner as gp130-Cγ1 except that a J-peptide (amino acid sequence: GQGTLVTVSS [SEQ ID NO: 4]) was inserted between the Ser-Gly bridge and the sequence of Cγ1 (see FIGS. 9A and 9B [SEQ ID NO: 9]).

(iii) gp130Δ3fibro-Cγ1 was engineered by fusing in frame the extracellular domain of gp130 without its three fibronectin-like domains (FIG. 10 [SEQ ID NO: 10]). The remaining part of this chimeric protein is identical to gp130-Cγ1.

(iv) gp130-J-$C_H1$ was engineered in a manner identical for that described for gp130-Cγ1, except that in place of the Cγ1 region only the $C_H1$ part of Cγ1 has been used (FIG. 11 [SEQ ID NO: 11]). The C-terminal domain of this construct includes the part of the hinge that contains the cysteine residue responsible for heterodimerization of the heavy chain of IgG with a light chain. The part of the hinge that contains the two cysteines involved in Cγ1 homodimerization has been deleted along with the $C_H2$ and $C_H3$ domains.

(v) gp130-Cγ4 was engineered in a manner identical to that described for gp130-Cγ1, except that Cγ4 was used in place of Cγ1 (FIG. 12 [SEQ ID NO: 12]). In addition, an RsrII DNA restriction site was engineered at the hinge region of the Cγ4 domain by introducing two silent base mutations. The RsrII site allows for other desired genetic engineering manipulations, such as the construction of the $C_H1$ equivalent of gp130-Cγ4.

(vi) gp130-κ was engineered in a manner identical to that described for gp130-Cγ1, except that the constant region of the κ light chain of human Ig was used in place of Cγ1 (FIG. 13 [SEQ ID NO: 13]).

(vi) gp130-J-κ was engineered in a manner identical to that described for gp130-J-κ, except that a j-peptide (amino acid sequence: TFGQGTKVEIK [SEQ ID NO: 5]) was inserted between the Ser-Gly bridge and the κ-region.

(viii) gp130-λ was engineered in a manner identical to that described for gp130-Cγ1, except that the constant region of the λ light chain (Cheung, et. al., Journal of Virology 66:6714–6720 (1992) of human Ig was used in place of Cγ1 (FIG. 14 [SEQ ID NO: 14]).

Constructs Employing Human IL-6a (i) IL6R-Cγ1 was engineered by fusing in frame amino acids 1 to 358 of IL-6Rα (Yamasaki et al., Science 241:825–828 (1988), which comprise the extracellular domain of IL-6Rα (FIG. 15 [SEQ ID NO: 15]), to an Ala-Gly bridge, followed by the 330 amino adds which comprise Cγ1 and a termination codon.

(ii) IL6R-κ was engineered as described for IL6R-Cγ1, except that the κ-domain (FIG. 13 [SEQ ID NO: 13]) utilized for gp130-κ was used in place of Cγ1.

(iii) IL6R-j-κ was engineered as described for IL6R-κ except that the j-peptide described for gp130j-κ was placed between the Ala-Gly bridge and the κ-domain.

(iv) Three additional constructs, IL6R313-Cγ1, IL6R313-κ, and IL6R313-j-κ, were engineered as using a truncated form of IL-6Ra comprised of amino acids 1 to 313 (FIG. 16 [SEQ ID NO: 16]). Each of these constructs were made by fusing in frame IL6R313 with a Thr-Gly bridge followed by the Cγ1, κ-, and j-κ-domains described above. These constructs were engineered in order to complement the gp130Δ3fibro-derived constructs.

Expression and purification of ligand traps

To produce covalently linked heterodimers of soluble gp130 and soluble IL-6Rα, gp130-Ig chimeric proteins were co-expressed with appropriate IL-6Rα-Ig chimeric proteins in complementing pairs. Co-expression was achieved by co-transfecting the corresponding expression vectors into suitable mammalian cell lines, either stably or transiently. The resulting disulfide-linked heterodimers were purified from conditioned media by several different methods, including but not limited to affinity chromatography on immobilized Protein A or Protein G, ligand-based affinity chromatography, ion exchange, and gel filtration.

Figure 17:
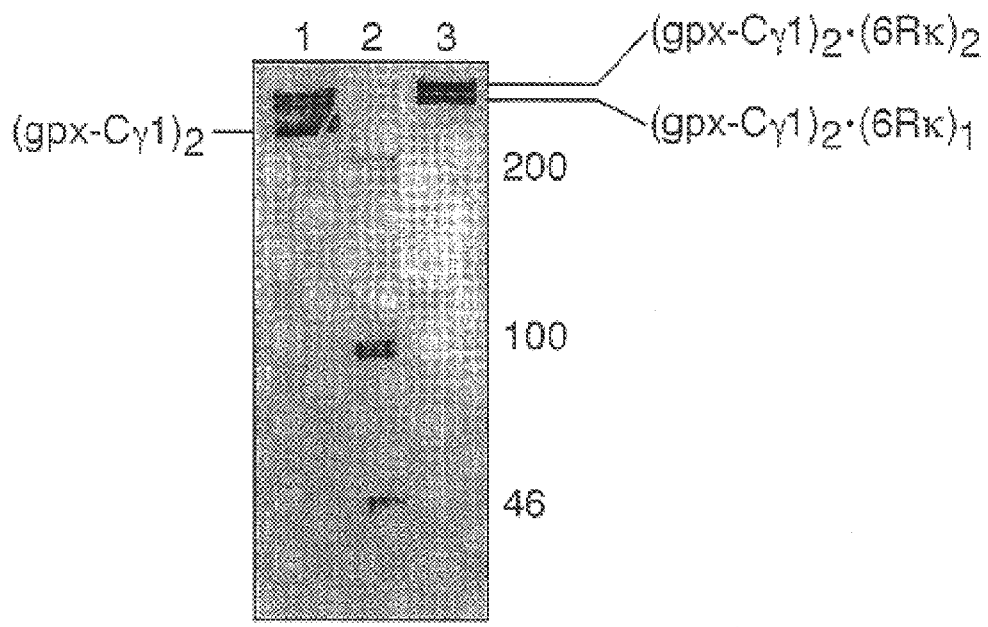
FIG. 17: Purification of gp130-Cγ1•IL-6Rα-κ. 4% to 12% SDS-PAGE gradient gel run under non-reducing conditions. Proteins were visualized by staining with silver. Lane 1: approximately 100 ng of material purified over Protein A Sepharose (Pharmacia). Lane 2: Molecular size standards (Amersham). Lane 3: The Protein A-purified material shown here after further purification over an IL-6 affinity chromatography step. The positions of the gp130-Cγ1 dimer [(gp130-Cγ1)$_2$], the gp130-Cγ1 dimer associated with one IL-6Rα-κ [(gp130-Cγ1)$_2$•(IL-6Rα-κ)$_1$], and the gp130-Cγ1 dimer associated with two IL-6Rα-κ [(gp130-Cγ1)$_2$•(IL-6Rα-κ)$_2$] are shown, as well as the sizes for the molecular size standards in kilodaltons (200, 100, and 46).

An example of the type of methods used for purification of a heavy/light receptor fusion protein is as follows: gp130-Cγ1•IL-6Rα-κ was expressed in COS cells by co-trans fecting two different vectors, encoding gp130-Cγ1 and IL-6Rα-κ respectively. Serum-free conditioned media (400 ml) were collected two days post-transfection and Cγ1-bearing proteins were purified by affinity chromatography over a 1 ml Protein A Sepharose (Pharmacia). The material generated in this step was further purified by a second affinity chromatography step over a 1 ml NHS-activated Sepharose (Pharmacia) which was derivatized with recombinant human IL-6, in order to remove gp130-Cγ1 dimer from gp130-Cγ1.IL-6Rα-κ complexes (the gp130-Cγ1 dimer does not bind IL-6). Proteins generated by this method were more than 90% pure, as evidenced by SDS-PAGE followed by silver-staining (FIG. 17). Similar protocols have been employed successfully towards the purification of other heavy/light receptor heterodimers.

RESULTS

Figure 18:
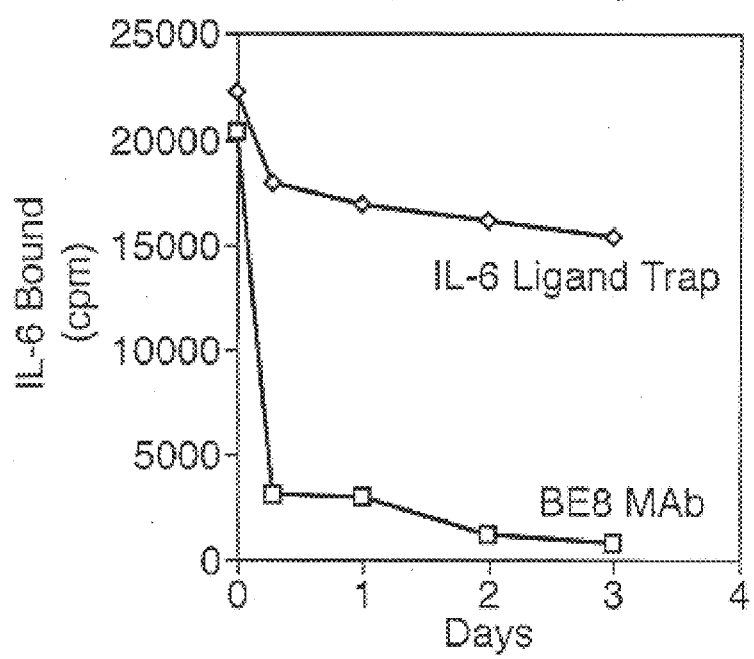
FIG. 18. IL-6 dissociates slowly from the ligand trap. The dissociation rate of IL-6 from a heavy/light chain receptor-based ligand trap (gp130-Cγ1.IL-6Rα-κ) was compared to that obtained with the neutralizing monoclonal antibody B-E8 (BE8 MAb).

Biological activity of immunoglobulin heavy/light chain receptor fusion antagonists The purified ligand traps were tested for their ability to bind IL-6 in a variety of different assays. For example, the dissociation rate of IL-6 bound to the ligand trap was measured in parallel with the dissociation rate of IL-6 from the anti-IL-6 monoclonal neutralizing antibody B-E8 [Brochier, et al., Int. J. Immunopharmacology 17:41–48 (1995), and references within]. An example of this type of experiment is shown in FIG. 18. In this experiment 20 pM $^{125}$I-IL-6 (1000 Ci/mmol; Amersham) was preincubated with 500 pM of either gp130-Cγ1•IL-6Rα-κ or mAb B-E8 for 20 hours. At this point a 1000-fold excess (20 nM) of "cold" IL-6 was added. Periodically, aliquots of the reaction were removed, the ligand trap or B-E8 were precipitated with Protein G-Sepharose, and the number of cpm of $^{125}$I-IL-6 that remained bound was determined. Clearly, the dissociation rate of human $^{125}$I-IL6 from the ligand trap was very slow—after three days, approximately 75% of the initial counts were still bound to the ligand trap. In contrast, less than 5% of the counts remained associated with the antibody after three days. This result demonstrates that the dissociation rate of the ligand from these ligand traps is very slow.

Figure 19A:
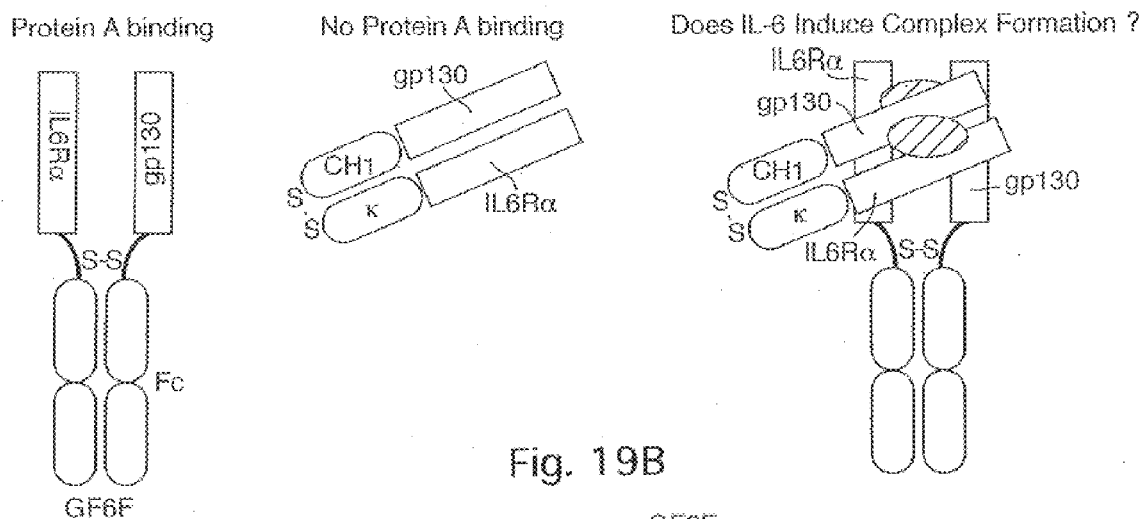
FIGS. 19A–B. IL-6 can induce multimerization of the ligand trap.
Figure 19B:
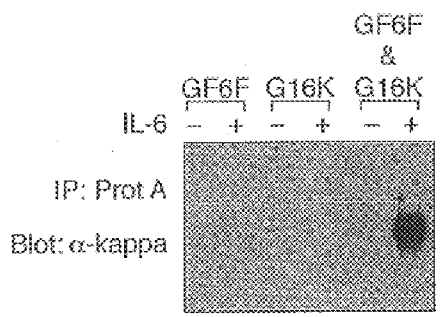

In a different set of experiments the ability of the ligand traps to multimerize in the presence of ligand was tested. An example of this is shown on FIGS. 19A and 19B. IL-6-induced association of gp130-Fc•IL-6Rα-Fc with gp130-$C_H1$•IL-6Rα-κ was determined by testing whether gp130-$C_H1$•IL-6Rα-κ, which does not by itself bind protein A, could be precipitated by protein A-Sepharose Sepharose in the presence of gp130-Fc•IL-6Rα-Fc in an IL-6-depended manner (FIGS. 9A and 9B [SEQ ID NO: 9]). Precipitation of gp130-$C_H1$•IL-6Rα-κ by Protein A-Sepharose was determined by western blotting with an anti-kappa specific HRP conjugate, which does not detect gp130-Fc•IL-6Rα-Fc. gp130-$C_H1$•IL-6Rα-κ could be precipitated by Protein A-Sepharose only when both gp130-Fc•IL-6Rα-Fc and IL-6 were present. This result conclusively indicates that IL-6 can induce ligand trap multimerization, and further indicate that the ligand trap can mimic the hexameric cytokine•Rα•signal transducer complex (FIG. 1). Ligand-induced multimerization may play a significant role in the clearance of cytokine•ligand trap complexes in vivo.

The biological activity of the different ligand traps may be further tested in assays which measure ligand-depended cell proliferation. Several cell proliferation assays exist for IL-6 and they employ cell lines such as B9, CESS, or XG1. An example of this type of assay using the XG-1 cell line is presented below: XG1 is a cell line derived from a human multiple myeloma (Zhang, et al., Blood 83:3654–3663 (1994). XG-1 depends on exogenously supplied human IL-6 for survival and proliferation. The $EC_{50}$ of IL-6 for the XG-1 line is approximately 50 pmoles/ml. The ability of several different IL-6 traps to block IL-6-depended proliferation of XG-1 cells was tested by incubating increasing amounts of purified ligand traps with 50 pg/ml IL-6 in XG-1 cultures. The ligand traps which were tested had been expressed and purified by methods similar to those described above. All of the ligand traps tested were found to inhibit IL-6-dependent proliferation of XG-1 in a dose dependent manner (FIG. 20). Of the five different traps tested gp130-Cγ1•IL-6Rα-κ was the most active and essentially display the same neutralizing activity towards IL-6 as the antibody B-E8. As little as a 10-fold molar excess of either gp130-Cγ1•IL-6Rα-κ or B-E8 completely blocked the activity of IL- 6 (a reading of A570–650=0.3 AU corresponds to no proliferation of the XG-1 cells). At a 100-fold molar excess all of the ligand traps tested completely blocked the activity of IL-6. This observed inhibition is highly selective as neither a gp130-Fc•CNTFRα-Fc ligand trap which blocks CNTF activity, nor gp130-Fc homodimer exhibit any blocking activity towards IL-6 even when used at a 1000-fold molar excess over IL-6 (data not shown). This data demonstrates that the heteromeric immunoglobulin heavy/light chain receptor-based ligand traps function as selective high affinity antagonists of their cognate ligand.

EXAMPLE 5

Cloning of Fusion Polypeptide Components

The extracellular domains of the human cytokine receptors were obtained by standard PCR techniques using tissue cDNAs (CLONTECH), cloned into the expression vector, pMT21 (Genetics Institute, Inc.), and the sequences were sequenced by standard techniques using an ABI 373A DNA sequencer and Taq Dideoxy Terminator Cycle Sequencing Kit (Applied Biosystems, Inc., Foster City, Calif.). For the IL-4Ra, nucleotides 241 through 868 (corresponding to the amino acids 24–231) from the Genbank sequence, X52425, were cloned. For the IL-2Rg, nucleotides 15 through 776 (corresponding to amino acids 1–233) from the Genbank sequence, D11086, were cloned. For the IL-6Ra, nucleotides 52 through 1044 (corresponding to the amino acids 1–331) from the Genbank sequence, X52425, were cloned. For gp130, nucleotides 322 through 2112 (corresponding to the amino acids 30–619) from the Genbank sequence, M57230, were cloned. For the IL-1RAcP, nucleotides 1 through 1074 (corresponding to the amino acids 1–358) from the Genbank sequence, AB006357, were cloned. For the IL-1RI, nudeotides 55 through 999 (corresponding to the amino acids 19–333) from the Genbank sequence, X16896, were cloned.

EXAMPLE 6

Production of Fusion Polypeptides
(CYTOKINE TRAPS)

The nucleotide sequences encoding the cytokine traps were constructed from the individual cloned DNAs (described supra) by standard cloning and PCR techniques. In each case, the sequences were constructed in frame such that the sequence encoding the first fusion polypeptide component was fused to the sequence encoding the second fusion polypeptide component followed by an Fc domain (hinge, CH2 and CH3 region of human IgG1) as the multimerizing component. In some cases extra nucleotides were inserted in frame between sequences encoding the first and second fusion polypeptide components to add a linker region between the two components (See FIGS. 21A–21D [SEQ ID NO: 17]—trap 424; FIGS. 24A–24F [SEQ ID NO: 23]—trap 412; and FIGS. 26A–26E [SEQ ID NO: 27]—trap 569).

For the IL-4 traps, 424 (FIGS. 21A–21D [SEQ ID NO: 17]), 603 (FIGS. 22A–22D [SEQ ID NO: 19]) and 622 (FIGS. 23A–23D [SEQ ID NO: 21]), the IL-2Rγ component is 5', followed by the IL4Rα component and then the Fc component. For the IL-6 traps, 412 (FIGS. 24A–24F [SEQ ID NO: 23]) and 616 (FIGS. 25A–25F [SEQ ID NO: 25]), the IL-6Rα component is 5' followed by the gp130 component and then the Fc domain. For the IL-1 trap 569 (FIGS. 26A–26E [SEQ ID NO: 27]), the IL-1RAcP component is 5' followed by the IL-1RI component and then the Fc domain. The final constructs were cloned into the mammalian expression vector pCDNA3.1 (STRATAGENE).

In the 569 sequence (FIGS. 26A–26E [SEQ ID NO: 27]), nucleotides 1–1074 encode the IL1RAcP component, nucleotides 1075–1098 encode a linker region, nucleotides 1099–2043 encode the IL1RI component and nucleotides 2044–2730 encode the Fc domain.

In the 412 sequence (FIGS. 24A–24F [SEQ ID NO: 23]), nucleotides 1–993 encode the IL6Rα component, nucleotides 994–1023 encode a linker region, nucleotides 1024–2814 encode the gp130 component and nucleotides 2815–3504 encode the Fc domain.

In the 616 sequence (FIGS. 25A–25F [SEQ ID NO: 25]), nucleotides 1–993 encode the IL6Rα component, nucleotides 994–2784 encode the gp130 component and nucleotides 2785–3474 encode the Fc domain.

In the 424 (FIGS. 21A–21D [SEQ ID NO: 17]) and 622 (FIGS. 23A–23D [SEQ ID NO: 21]) sequences, nucleotides 1–762 encode the IL2Rγ component, nucleotides 763–771 encode a linker region, nucleotides 772–1395 encode the IL4Rα component and nucleotides 1396–2082 encode the Fc domain.

Finally, in the 603 sequence (FIGS. 22A–22D [SEQ ID NO: 19]), nucleotides 1–762 encode the IL2Rγ component, nucleotides 763–1386 encode the IL4Rα component and nucleotides 1387–2073 encode the Fc domain.

DNA constructs were either transiently transfected into COS cells or stably, transfected into CHO cells by standard techniques well known to one of skill in the art. Supernatants were collected and purified by protein A affinity chromatography and size exclusion chromatography by standard techniques. (See for example Harlow and Lane, Antibodies—A Laboratory Manual, Cold Spring Harbor Laboratory, 1988).

EXAMPLE 7

IL-4 Bioassay Protocol Using TF-1 (ATCC) Cells
Reagents and Equipment Needed
MTT Dye Solution
  MTT(3-[4,5-Dimethylthiazole-2-yl]) (Sigma catalog# M2128)
  Working concentration: Dissolve 5 mg of anhydrous MTT in 200 ml PBS without $Ca^{+2}$, $Mg^{+2}$.
  Sterile filter and store aliquoted at −20° C.

Solubilization Solution

For 1000 ml, combine 100 g SDS, 950 ml dH$_2$0, 50 ml Dimethyl Formamide, and 850 µl concentrated HCl.

Filter sterilize with a 0.45 µm filter unit.

Store at room temperature

TF-1 Cell Growth Medium

RPMI 1640, 10% FBS, Pen/Strep, 2 mM L-glutamine

Other 0.4% Trypan Blue Stain, sterile tubes for dilutions, sterile 96 well cell culture plates (Falcon#3072), hemacytometer, centrifuge, ELISA plate reader, multichannel pipet for 15, 25, 50 and 100 µl volume, sterile reagent reservoirs, sterile pipet tips, gloves.

Assay Protocol

A. Preparation of Assay Plates

1. Prepare sterile 96 well tissue culture plates to contain 50 µl of growth medium per well with various concentrations of IL-4 and 10 nM IL-4 antagonist. This can be done by preparing a working dilution of IL-4 that is 4 times the highest concentration to be assayed. In separate tubes, do a two-fold serial dilution of the IL-4. Add 25 µl of each dilution to one row across the plate (i.e. row A gets highest concentration, row G gets lowest concentration). Add 25 µl of growth medium without IL-4 to row H. Prepare the antagonists to be tested by making a stock that is 4 times the final concentration. Add 25 µl to a triplicate set of IL-4 containing wells (columns 1,2,3, A through H). Be sure to include antagonist in row H.

2. As a positive control, leave one set with no antagonist. These wells will contain IL-4 and media only.

3. Incubate the plate for 1–2 hours at 37° C. in a humidified 5% CO$_2$ incubator before preparing cells to be used for assay.

B. Preparation of Cells

4. Wash cells twice by centrifugation in assay medium free of growth factor.

5. Determine cell number and trypan blue viability and suspend cells to a final concentration of 8×10$^5$/ml in assay medium.

6. Dispense 50 µl of the cell suspension (40,000 cells) into all wells of the plates. Total volume should now be 100 µl/well.

7. Incubate the plate at 37° C. for 68 hours in a humidified 5% CO$_2$ incubator.

C. Color Development

8. After incubating for 68 hours, add 15 µl of the MTT dye solution to each well.

9. Incubate the plate at 37° C. for 4 hours in a humidified 5% CO$_2$ incubator.

10. After 4 hours, add 100 µl of the solubilization solution to each well. Allow the plate to stand overnight in a sealed container to completely solubilize the formazan crystals.

11. Record the absorbance at 570/650 nm.

Results

Figure 27:
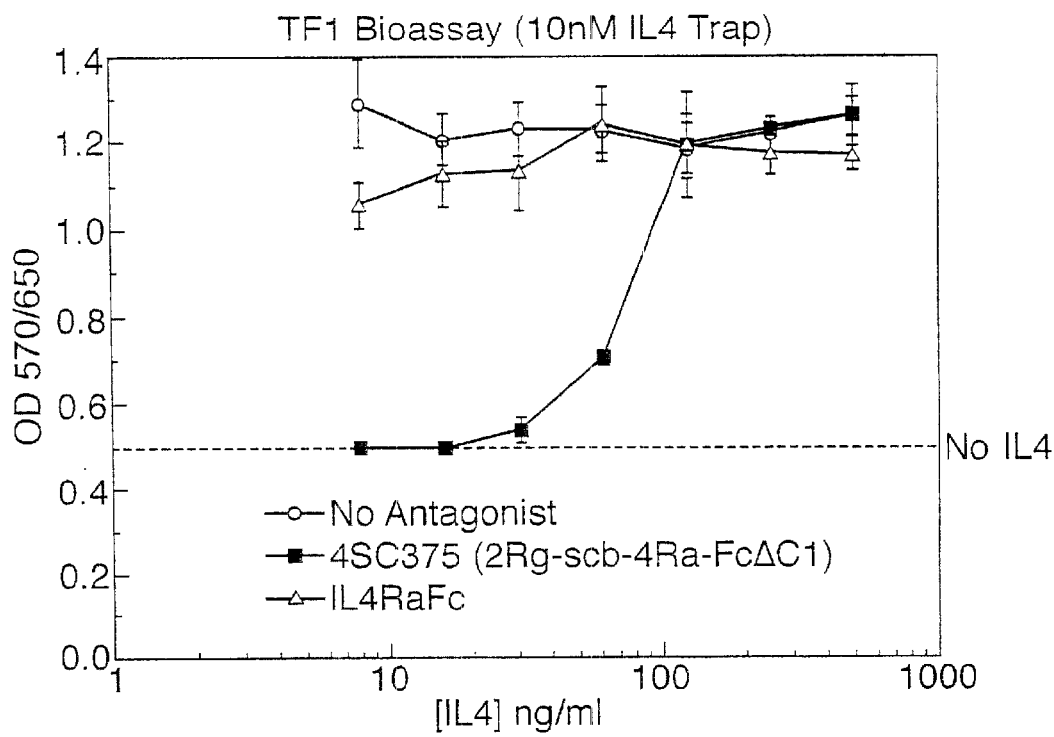
FIG. 27—shows that an IL-4 trap designated 4SC375, which is a fusion polypeptide of IL-2Rγ-scb-IL4Rα-FcΔC1, is several orders of magnitude better as an IL-4 antagonist than IL4RαFcΔC1 alone in the TF1 cell bioassay.

FIG. 27 shows that an IL-4 trap designated 4SC375, which is a fusion polypeptide of IL-2Rγ-scb-IL4Rα-FcΔC1, is several orders of magnitude better as an IL-4 antagonist than IL4RαFcΔC1 alone in the TF1 cell bioassay.

Figure 28:
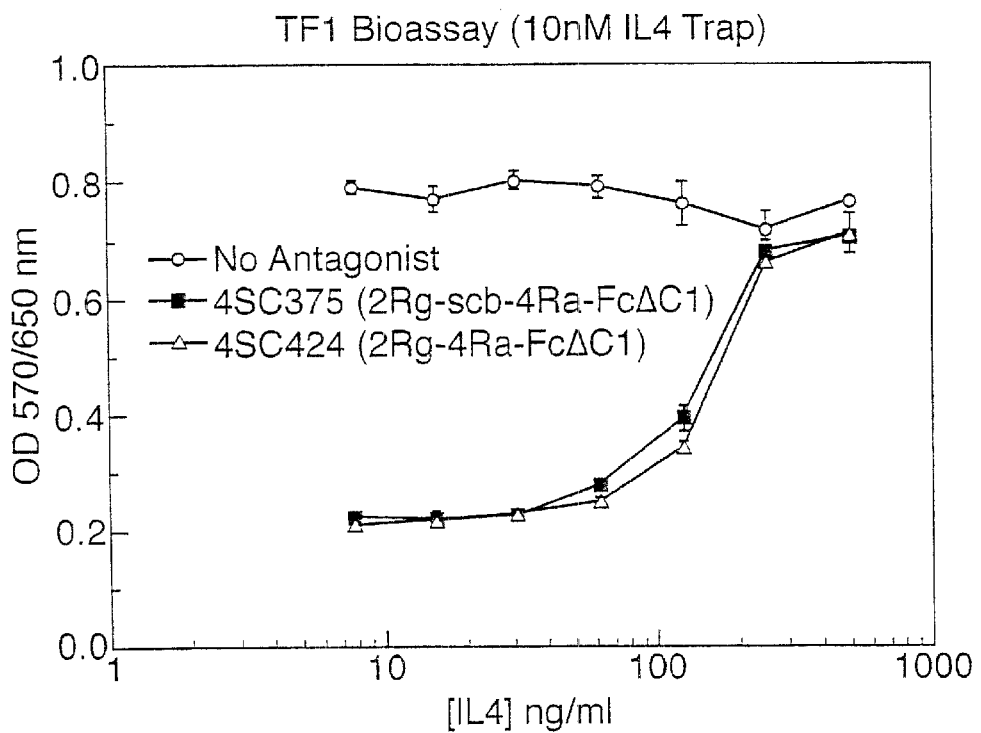
FIG. 28—shows that an IL-4 trap designated 4SC375 displays antagonistic activity in the TF1 cell bioassay equivalent to an IL-4 trap designated 4SC424 (described in FIGS. 21A–21D) which is a fusion polypeptide of IL-2Rγ-IL4Rα-FcΔC1 having the IL-2Rγ component flush with the IL-4Rα component.

FIG. 28 shows that the IL-4 trap designated 4SC375 shows antagonistic activity in the TF1 cell bioassay equivalent to an IL-4 trap designated 4SC424 which is a fusion polypeptide of IL-2Rγ-IL4Rα-FcΔC1 having the IL-2Rγ component flush with the IL-4Rα component.

EXAMPLE 8

IL-6 Bioassay Protocol Using XG1 Cells

Reagents and Equipment Needed

MTT Dye Solution

MTT(3-[4,5-Dimethylthiazole-2-yl]) (Sigma catalog# M2128)

Working concentration: Dissolve 5 mg of anhydrous MTT in 200 ml PBS without Ca+2, Mg+2.

Sterile filter and store aliquoted at −20° C.

Solubilization Solution

For 1000 ml, combine100 g SDS, 950 ml dH$_2$0, 50 ml Dimethyl Formamide, and 850 µl concentarted HCl.

Filter sterilize with at 0.45 µm filter unit.

Store at room temperature

Assay Medium

RPMI 1640, 10% FBS, Pen/Strep, 2 mM L-glutamine, 50 µM mercapto-ethanol.

Other 0.4% Trypan Blue Stain, sterile tubes for dilutions, sterile 96 well cell culture plates (Falcon#3072), hemacytometer, centrifuge, ELISA plate reader, multichannel pipet for 15, 25, 50 and 100 µl volume, sterile reagent reservoirs, sterile pipet tips, gloves.

Assay Protocol

A. Preparation of Assay Plates

1. Prepare sterile 96 well tissue culture plates to contain 50 µl of growth medium per well with various concentrations of IL-6 and 10 nM IL-6 antagonist. This can be done by preparing a working dilution of IL-6 that is 4 times the highest concentration to be assayed. In separate tubes, do a two-fold serial dilution of the IL-6. Add 25 µl of each dilution to one row across the plate (i.e. row A gets highest concentration, row G gets lowest concentration). Add 25 µl of growth medium without IL-6 to row H. Prepare the antagonists to be tested by making a stock that is 4 times the final concentration. Add 25 µl to a triplicate set of IL-6 containing wells (columns 1,2,3, A through H). Be sure to include antagonist in row H. A typical IL-6 titration starts at 200 ng/ml down to 3.1 ng/ml.

2. As a positive control, leave one set with no antagonist. These wells contain IL-6 and media in place of antagonist.

3. Incubate the plate 1–2 hours at 37° C. in a humidified 5% CO$_2$ incubator before preparing cells to be used for assay.

B. Preparation of Cells

4. Wash cells twice by centrifugation (5 min at 1000 RPM) in assay medium free of growth factor.

5. Determine cell number and trypan blue viability and suspend cells to a final concentration of 8×10$^5$/ml in assay medium.

6. Dispense 50 µl of the cell suspension (40000 cells) into all wells of the plates. Total volume should now be 100 µl/well.

7. Incubate the plate at 37° C. for 68 hours in a humidified 5% CO$_2$ incubator.

C. Color Development

8. At 68 hours add 15 µl of the dye solution to each well.

9. Incubate the plate at 37° C. for 4 hours in a humidified 5% CO$_2$ incubator.

10. After 4 hours, add 100 µl of the solubilization solution to each well. Allow the plate to stand overnight in a sealed container to completely solubilize the formazan crystals.

11. Record the absorbance at 570/650 nm.

Results

Figure 29:
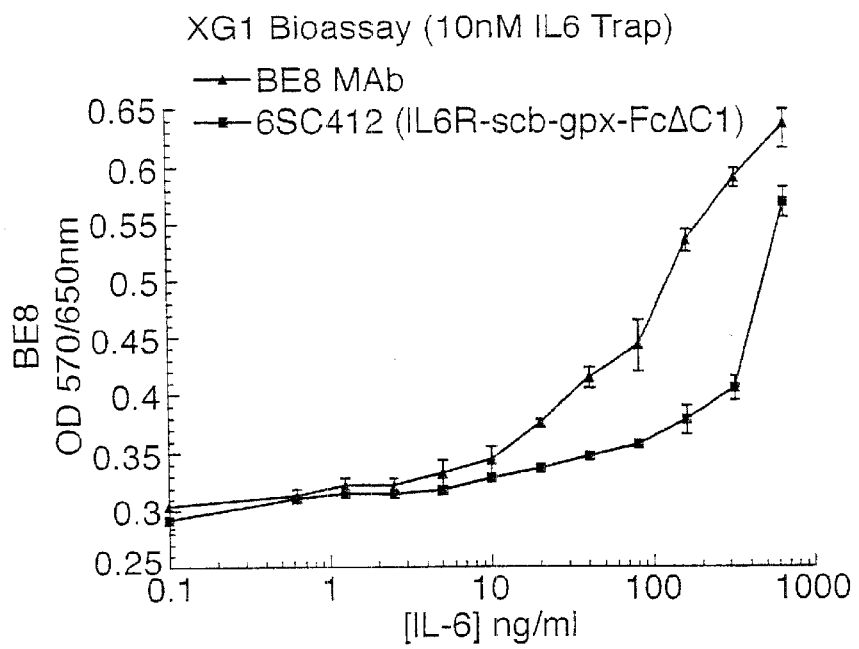
FIG. 29—shows that the IL6 trap (6SC412 IL6R-scb-gpx-FcΔC1) described in FIGS. 24A–24F is a better antagonist of IL-6 in the XG1 bioassay than the neutralizing monoclonal antibody to human IL-6 -BE8.

FIG. 29 shows that the IL6 trap (6SC412 IL6R-scb-gpx-FcΔC1) described in FIGS. 24A–24F (SEQ ID NOS: 23 and 24) is a better antagonist of IL-6 in the XG1 bioassay than the neutralizing monoclonal antibody to human IL-6 - BE8.

EXAMPLE 9

MRC5 Bioassay for IL1 Traps

MRC5 human lung fibroblast cells respond to IL-1 by secreting IL-6 and thus were utilized to assay the ability of IL-1 traps to block the IL-1-dependent production of IL-6. IL1 Trap 1SC569 (FIGS. 26A–26E [SEQ ID NOS: 27 and 28]) was tested against IL-1-RI.Fc which is the extracellular domain of the IL-1 Type I receptor fused to an Fc domain. MRC5 cells are suspended at 1×10$^5$ cells per ml in medium and 0.1 ml of cells are plated (10,000 cells per well) into the wells of a 96 well tissue culture plate. Plates are incubated for 24 hours at 37° C. in a humidified 5% CO$_2$ incubator.

IL-1 trap and recombinant human IL-1 at varying doses are pre-incubated in a 96 well tissue culture dish and incubated for 2 hours at 37° C. 0.1 ml of this mixture is then added to the 96 well plate containing the MRC5 cells such that the final concentration of IL-1 Trap is 10 nM and the final concentrations of the IL-1 ranges from 2.4 pM to 5 nM. Control wells contain trap alone or nothing.

Plates are then incubated at 37° C. for 24 hours in a humidified 5% CO$_2$ incubator. Supernatant is collected and assayed for levels of IL-6 using R&D Systems Quantikine Immunoassay Kit according to the manufacturer's instructions.

Results

Figure 30:
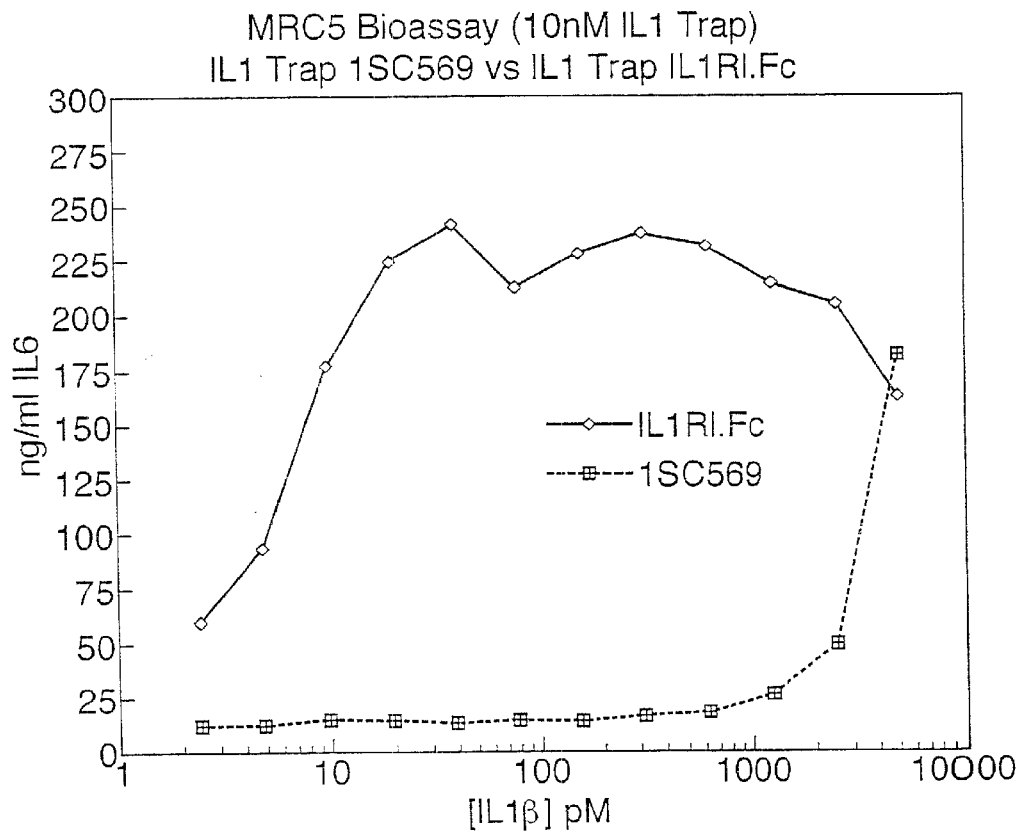
FIG. 30—shows that the trap 1SC569 (described in FIGS. 26–26E) is able to antagonize the effects of IL-1 and block the IL-6 production from MRC 5 cells upon treatment with IL-1.

FIG. 30 shows that the trap 569 (FIGS. 26A–26E [SEQ ID NOS: 27 and 28]) is able to antagonize the effects of IL-1 and block the IL-6 production from MRC 5 cells upon treatment with IL-1. At a concentration of 10 nM, the trap 569 is able to block the production of IL-6 up to an IL-1 concentration of 3 nM. In contrast, the IL-1RI.Fc is a much poorer antagonist of IL-1. It is only able to block the effects of IL-1 up to about 10–20 pM. Thus, the trap 569 is approximately 100× better at blocking IL-1 than IL1RI.Fc.

EXAMPLE 10

Construction of IL-13/IL-4 Single Chain Traps

1. PCR cloning of human IL-13Rα1 from human spleen cDNA.

The extracellular domain of human IL-13Rα1 (corresponding to nucleotides #34-1062 from Genbank Accession # Y09328) was amplified by standard PCR techniques. The PCR product was then ligated into an expression vector (pCDNA3.1 Stratagene) containing human Fc construct to create a fusion protein consisting of the extracellular domain of human IL-13Rα1 fused in frame with the hinge, CH2 and CH3 region of human IgG1. The human IL-13Rα1 sequence was verified. The DNA encoding IL-13Rα1.Fc was transfected into COS cells and protein expression was verified by Western Blot analysis of the cell media.

2. Construction of IL-13/IL-4 Traps a. IL-4Rα.IL-13Rα1.Fc

The IL-13Rα1 extracellular domain (not including the predicted signal peptide, therefore nt #100-1062; amino acid #23-343) was amplified by standard PCR techniques and ligated into an expression vector, pMT21, to create an in frame fusion downstream of the extracellular domain of human IL-4Rα (nucleotides 176 through 868 (corresponding to the amino acids 1–231) from the Genbank sequence X52425) and upstream of the human Fc. The IL-4Rα contains a nucleotide change at nt# 794 (T to A) to change the amino acid at #207 to a Ser from a Cys. A two amino acid linker with the amino acid sequence SG was constructed in frame between the IL-4Rα and the IL-13Rα1. The human IL-13Rα1 sequence was verified. The construct encoding this single chain trap was transfected into COS cells and protein expression was verified by Western Blot analysis of the cell media. The nudeotide and amino acid sequence of the IL-4Rα.IL-13Rα1.Fc single chain trap is set forth in FIGS. 31A–31G.

b. IL-13Rα1.IL-4Rα.Fc

The IL-13Rα1 extracellular domain (including the signal peptide, therefore nts #34-1062; amino acid #1-343) was amplified by standard PCR techniques and ligated into an expression vector, pJFE14, to create an in-frame fusion upstream of the human IL-4Ra (nucleotides 236 through 868 (corresponding to the amino acids 21–231) from the Genbank sequence X52425) and human Fc. A ten amino acid linker with the amino acid sequence GAPSGGGGRP (SEQ ID NO: 6) was constructed in frame between the IL-4Rα and the IL-13Rα1. The human IL-13Rα1 sequence was verified. The construct encoding this single chain trap was transfected into COS cells and protein expression was verified by Western Blot analysis of the cell media. The nucleotide and amino acid sequence of the IL-13Rα1.IL-4Rα.Fc single chain trap is set forth in FIGS. 32A–32G (SEQ ID NOS: 31 and 32).

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

We claim:

1. An isolated nucleic acid molecule encoding a fusion polypeptide capable of binding a cytokine to form a nonfunctional complex comprising:
   a) a nucleotide sequence encoding a first fusion polypeptide component comprising the amino acid sequence of the cytokine binding portion of the extracellular domain of the specificity determining component of a receptor for the cytokine;
   b) a nucleotide sequence encoding a second fusion polypeptide component comprising the amino acid sequence of the cytokine binding portion of the extracellular domain of the signal transducing component of a receptor for the cytokine; and c) a nucleotide sequence encoding a third fusion polypeptide component comprising the amino acid sequence of a multimerizing component, wherein the receptor of a) can be the same or different from the receptor of b).

2. The nucleic acid molecule of claim 1, wherein the nucleotide sequence encoding the first component is upstream of the nucleotide sequence encoding the second component.

3. The nucleic acid molecule of claim 1, wherein the nucleotide sequence encoding the first component is downstream of the nucleotide sequence encoding the second component.

4. The isolated nucleic acid molecule of claim 1, wherein the cytokine receptor is the receptor for a member of the hematopoietin family of cytokines selected from the group consisting of interleukin-2, interleukin-3, interleukin-4, interleukin-5, interleukin-6, interleukin-7, interleukin-9, interleukin-11, interleukin-13, interleukin-15, granulocyte macrophage colony stimulating factor, oncostatin M, and leukemia inhibitory factor.

5. The isolated nucleic acid molecule of claim 1, wherein the cytokine receptor is the receptor for a member of the interferon family of cytokines selected from the group consisting of IFN-gamma, IFN-alpha, and IFN-beta.

6. The isolated nucleic acid molecule of claim 1, wherein the cytokine receptor is the receptor for a member of the immunoglobulin superfamily of cytokines selected from the group consisting of B7.1 (CD80) and B7.2 (B70).

7. The isolated nucleic acid molecule of claim 1, wherein the cytokine receptor is the receptor for a member of the TNF family of cytokines selected from the group consisting of TNF-alpha, TNF-beta, LT-beta, CD40 ligand, Fas ligand, CD 27 ligand, CD 30 ligand, and 4-1BBL.

8. The isolated nucleic acid molecule of claim 1, wherein the cytokine receptor is the receptor for a member of the TGF-β/BMP family selected from the group consisting of TGF-β1, TGF-β2, TGF-β3, BMP-2, BMP-3a, BMP-3b, BMP-4, BMP-5, BMP-6, BMP-7, BMP-8a, BMP-8b, BMP-9, BMP-10, BMP-11, BMP-15, BMP-16, endometrial bleeding associated factor (EBAF), growth differentiation factor-1 (GDF-1), GDF-2, GDF-3, GDF-5, GDF-6, GDF-7, GDF-8, GDF-9, GDF-12, GDF-14, mullerian inhibiting substance (MIS), activin-1, activin-2, activin-3, activin-4, and activin-5.

9. The isolated nucleic acid molecule of claim 1, wherein the cytokine receptor is the receptor for a cytokine selected from the group consisting of interleukin-1, interleukin-10, interleukin-12, interleukin-14 and MIF.

10. The isolated nucleic acid molecule of claim 1, wherein the multimerizing component comprises an immunoglobulin derived domain.

11. The isolated nucleic acid molecule of claim 10, wherein the immunoglobulin derived domain is selected from the group consisting of the Fc domain of IgG, the heavy chain of IgG, and the light chain of IgG.

12. A fusion polypeptide encoded by the isolated nucleic acid molecule of claim 1.

13. A composition capable of binding a cytokine to form a nonfunctional complex comprising a multimer of the fusion polypeptide of claim 12.

14. The composition of claim 13, wherein the multimer is a dimer.

15. A vector which comprises the nucleic acid molecule of claim 1.

16. An expression vector comprising a nucleic acid molecule of claim 1, wherein the nucleic acid molecule is operatively linked to an expression control sequence.

17. A host-vector system for the production of a fusion polypeptide which comprises the expression vector of claim 16, in a suitable host cell.

18. The host-vector system of claim 17, wherein the suitable host cell is a bacterial cell, yeast cell, insect cell, or mammalian cell.

19. The host-vector system of claim 17, wherein the suitable host cell is *E. coli.*

20. The host-vector system of claim 17, wherein the suitable host cell is a COS cell.

21. The host-vector system of claim 17, wherein the suitable host cell is a CHO cell.

22. The host-vector system of claim 17, wherein the suitable host cell is a 293 cell.

23. The host-vector system of claim 17, wherein the suitable host cell is a BHK cell.

24. The host-vector system of claim 17, wherein the suitable host cell is a NS0 cell.

25. A method of producing a fusion polypeptide which comprises growing cells of the host-vector system of claim 17, under conditions permitting production of the fusion polypeptide and recovering the fusion polypeptide so produced.

* * * * *